(12) United States Patent
Li

(10) Patent No.: US 9,890,386 B2
(45) Date of Patent: Feb. 13, 2018

(54) SOYBEAN TRANSCRIPTION TERMINATORS AND USE IN EXPRESSION OF TRANSGENIC GENES IN PLANTS

(71) Applicant: E I DU PONT DE NEMOURS AND COMPANY, Wilmington, DE (US)

(72) Inventor: Zhongsen Li, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 53 days.

(21) Appl. No.: 15/001,429

(22) Filed: Jan. 20, 2016

(65) Prior Publication Data

US 2016/0222396 A1    Aug. 4, 2016

Related U.S. Application Data

(62) Division of application No. 14/255,267, filed on Apr. 17, 2014, now Pat. No. 9,273,311, which is a division of application No. 13/561,150, filed on Jul. 30, 2012, now Pat. No. 8,741,634, which is a division of application No. 13/288,992, filed on Nov. 4, 2011, now Pat. No. 8,263,399, which is a division of application No. 12/486,793, filed on Jun. 18, 2009, now Pat. No. 8,080,413.

(60) Provisional application No. 61/073,389, filed on Jun. 18, 2008.

(51) Int. Cl.
*C12N 15/82*  (2006.01)
*C12N 15/11*  (2006.01)

(52) U.S. Cl.
CPC ........ *C12N 15/8216* (2013.01); *C12N 15/11* (2013.01); *C12N 15/8245* (2013.01); *C12N 15/8247* (2013.01); *C12N 15/8251* (2013.01); *C12N 15/8261* (2013.01); *C12N 15/8273* (2013.01); *C12N 15/8274* (2013.01); *C12N 15/8279* (2013.01); *C12N 15/8286* (2013.01)

(58) Field of Classification Search
None
See application file for complete search history.

(56) References Cited

U.S. PATENT DOCUMENTS

| | | | |
|---|---|---|---|
| 5,932,479 A * | 8/1999 | Daniell | C12N 15/8214 435/320.1 |
| 6,737,563 B2 | 5/2004 | Yu et al. | |
| 7,345,217 B2 | 3/2008 | Zhang et al. | |
| 7,511,190 B2 | 3/2009 | Creelman et al. | |
| 2004/0031072 A1 | 2/2004 | La Rosa et al. | |
| 2006/0015283 A1 | 1/2006 | Boerstler et al. | |
| 2006/0107345 A1 | 5/2006 | Alexandrov et al. | |
| 2007/0067865 A1 | 3/2007 | Kovalic et al. | |
| 2007/0214517 A1 | 9/2007 | Alexandrov et al. | |
| 2007/0283459 A1 | 12/2007 | Byrum et al. | |
| 2008/0276334 A1 | 11/2008 | Abad et al. | |
| 2009/0093620 A1 | 4/2009 | Kovalic et al. | |

FOREIGN PATENT DOCUMENTS

| | | |
|---|---|---|
| WO | 2008/034648 A1 | 3/2008 |
| WO | 2009/037329 A2 | 3/2009 |

OTHER PUBLICATIONS

Anne Ulimari et al., Myb26: a MYB-like protein of pea flowers with affinity for promoters of phenylpropanoid genes, The Plant Journal, 1997, pp. 1273-1284, vol. 12(6).
K. Diane Jofuku et al., Kunitz Trypsin Inhibitor Genes Are Differentially Expressed during the soybean Life Cycle and in Transformed Tobacco Plants, The Plant Cell, 1989, pp. 1079-1093, vol. 1.
Norbert Uehlein et al., Arbuscular mycorrhizal symbiosis and plant aquaporin expression, Phytochemistry, 2007, pp. 122-129, vol. 68.
Fernando Aguilar et al., Two genes encoding the soybean translation elongation factor eEF-1α are transcribed in seedling leaves, Plant Molecular Biology, 1991, pp. 351-360, vol. 17.
Francisco J. Munoz et al., Increased expression of two cDNAs encoding metallothionein-like proteins during growth of Cicer arietinum epicotyls, Physiologia Plantarum, 1998, pp. 273-279, vol. 104.
National Center for Biotechnology Information General Identification No. 110931697, Aug. 5, 2006, Accession No. DQ822907, Y. Liao et al., Soybean MYB genes response to abiotic stresses.
National Center for Biotechnology Information General Identification No. 210142208, Nov. 19, 2008, Accession No. AK246127, T. Umezawa et al., Sequencing and Analysis of Approximately 40,000 Soybean cDNA clones.
National Center for Biotechnology Information General Identification No. 210142828, Nov. 19, 2008, Accession No. AK285610, T. Umezawa et al., Sequencing and Analysis of Approximately 40,000 Soybean cDNA clones.
National Center for Biotechnology Information General Identification No. 210142502, Nov. 19, 2008, Accession No. AK285380, T. Umezawa et al., Sequencing and Analysis of Approximately 40,000 Soybean cDNA clones.
Aiqiu Xing et al., Revealing frequent alternative polyadenylation and widespreatd low-level transcription read-through of novel plant transcription terminators, Plant Biotechnology Journal, 2010, pp. 772-782; vol. 8.

\* cited by examiner

*Primary Examiner* — Brent Page
(74) *Attorney, Agent, or Firm* — E.I. Dupont De Nemours & Co.

(57) ABSTRACT

Five novel plant transcription terminators MYB2, KTI1, PIP1, EF1A2, and MTH1 are isolated from soybean and their functions in the regulation of RNA transcription and processing in plants are described.

12 Claims, 19 Drawing Sheets

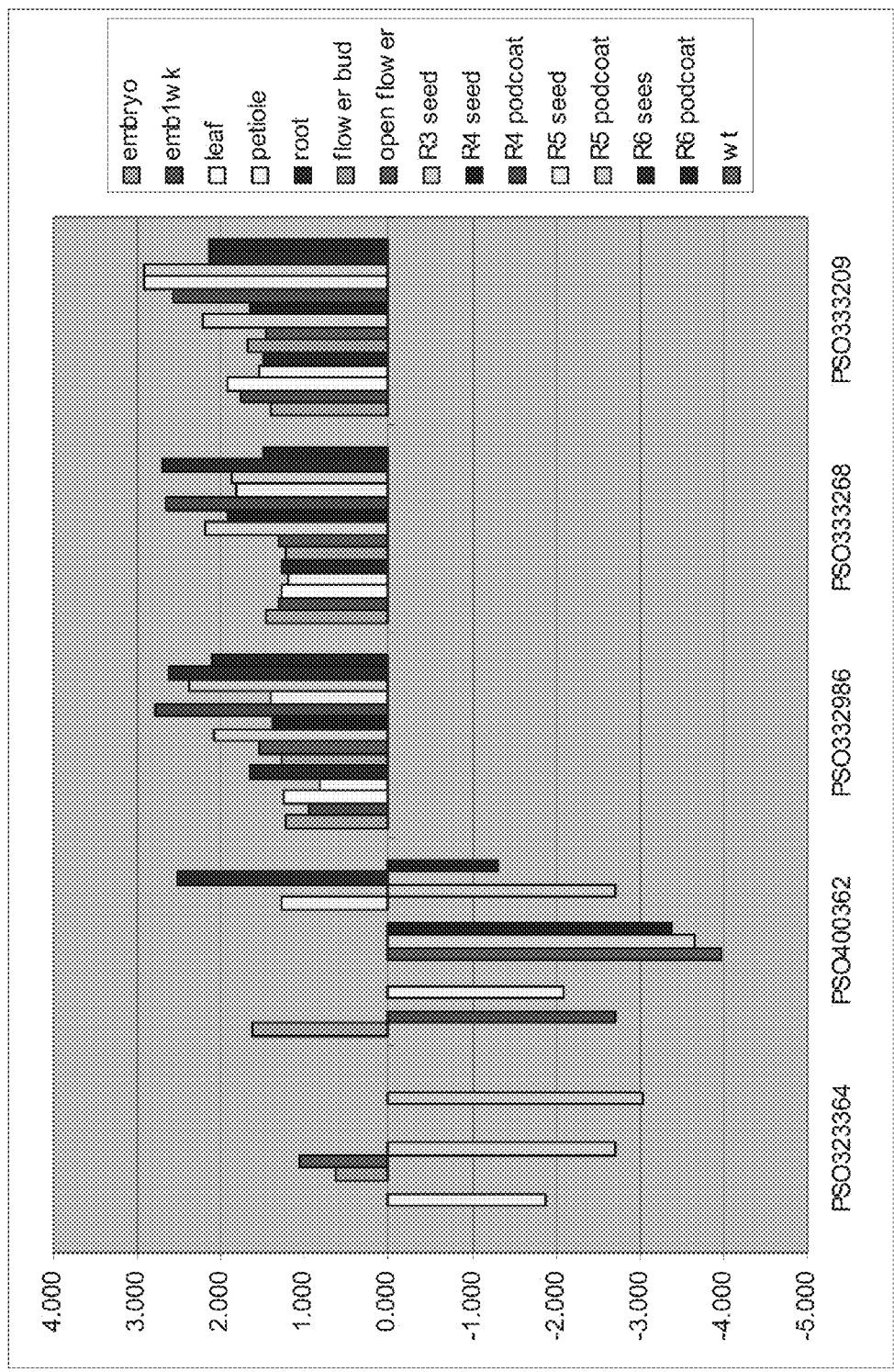

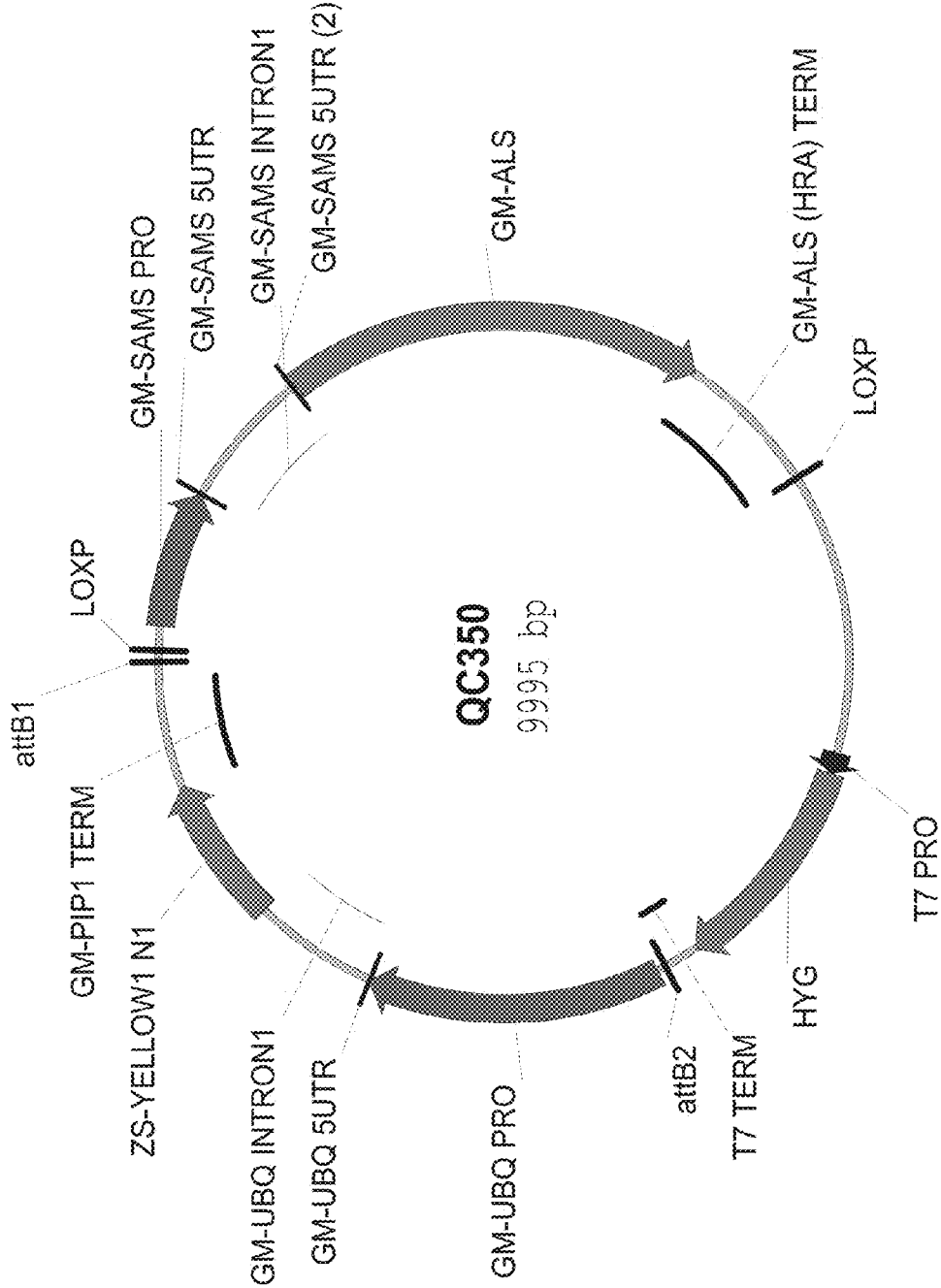

QC339: MYB2 540 bp; QC340: KTI1 554 bp; QC350: PIP1 518 bp;
QC351: EF1A2 445 bp; QC352: MTH1 462 bp;

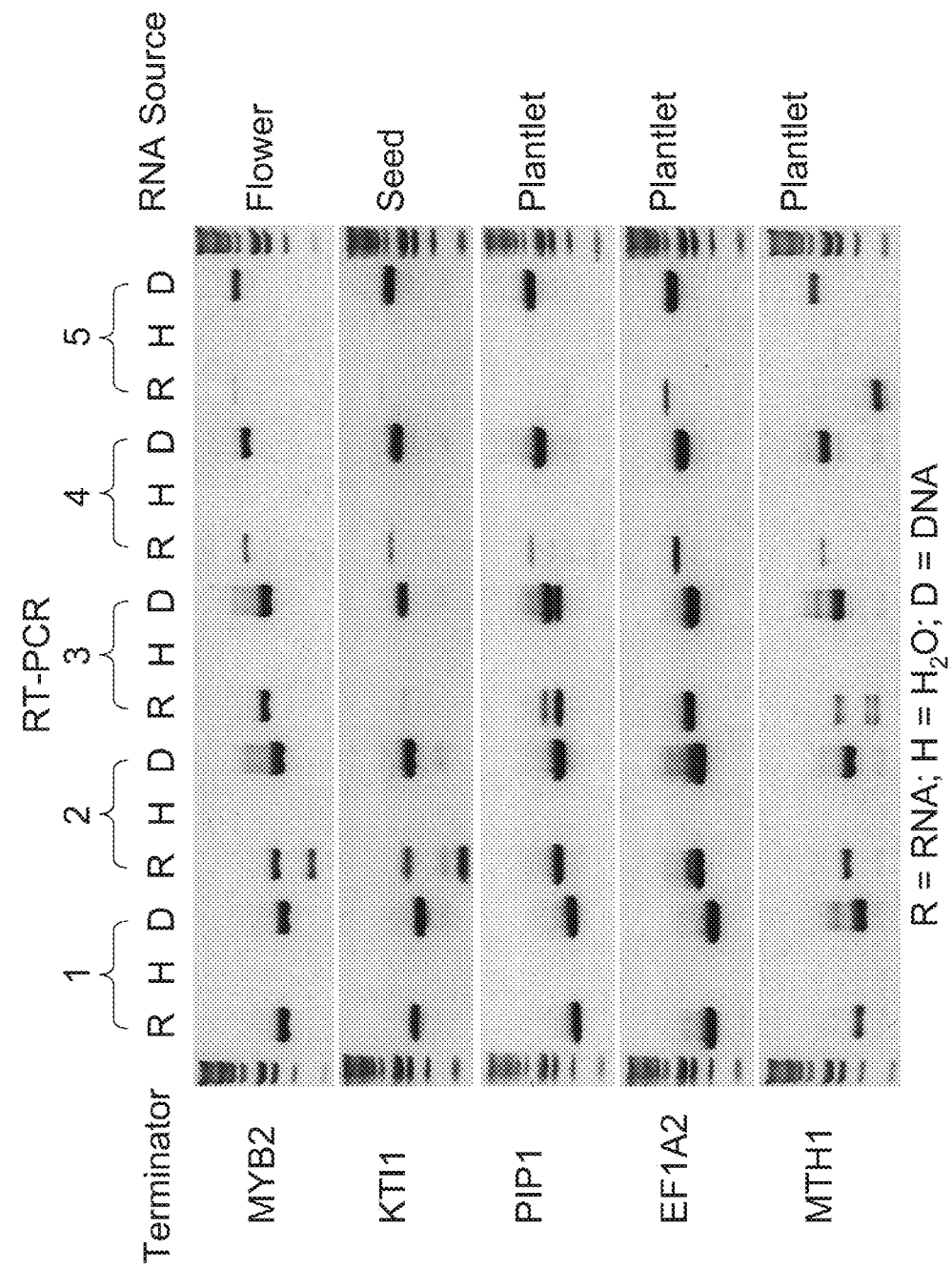

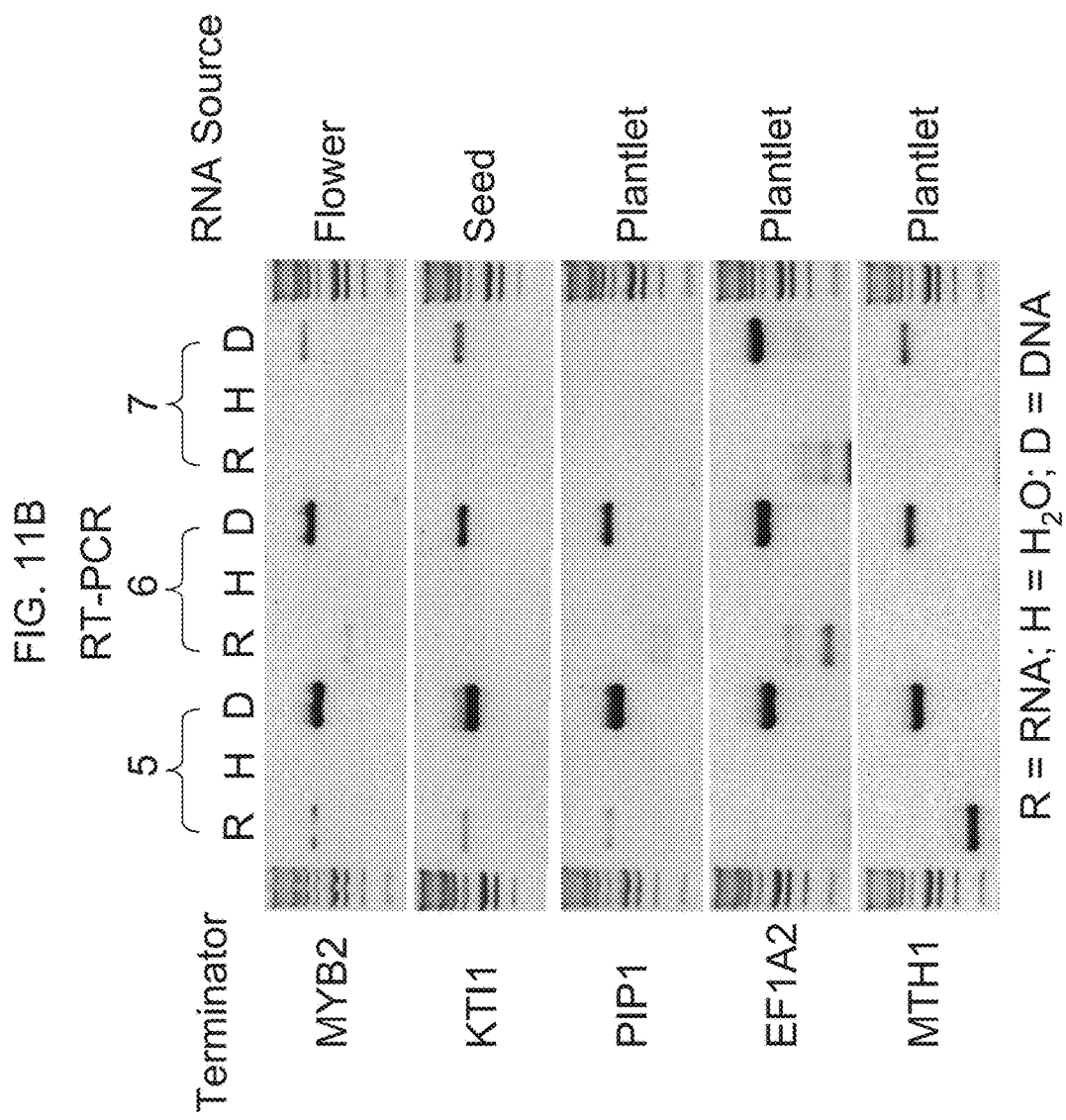

SEQUENCE LISTING

```
<160> NUMBER OF SEQ ID NOS: 128

<210> SEQ ID NO 1
<211> LENGTH: 537
<212> TYPE: DNA
<213> ORGANISM: glycine max

<400> SEQUENCE: 1
gagctctgaa cgggaattaa acctataaac ataaatataa ataatatata taaacctaag    60
tgtctaagtt ccataaatta agctgtagtc tctggcttaa aacatgttag gtttgtttat   120
acaagtagtt ggatgtttgg agtacttcgg tcttttgcgt accatcaata tttaagaact   180
aagttagtta tgttccgtaa cttatgggct cttaattaaa ctatatctgc acaaaattat   240
atatatatca aatgtgatgg tatgtggact ataaaaagat atggttgaga accacaaact   300
ttgaaacttc gaataatata ttgccagtga cagtcttgtt gatttgttat agcaagtcct   360
attttcttaa tcattgcttt gttttaacgt acctagattt cataactttt gtctttgtct   420
caagctgaac ctaatgatga tagtaatatt aacttattgt ataggggtat ttcataggat   480
aaaaaatgat gtgcaattac gtgtagacca aatattactt gatgacagat ggaattc      537

<210> SEQ ID NO 2
<211> LENGTH: 551
<212> TYPE: DNA
<213> ORGANISM: glycine max

<400> SEQUENCE: 2
gagctctgaa gcagtaccac actggcccaa aaaaaaaatt catgtgctta atttctagct    60
gtgagagaca attaagtgta tgaccaataa aatggttttg ttgtaggacc aagtctgaga   120
gacgccaagc accacatgaa taaataacc aaagcttggt ttgtattgta gccttctcta    180
atgctattgg tctggttaca tcatctttaa ttcccctta tatatgcata tgtttattat    240
ttattgattt atccttgaaa gagtacaatt taacttttaa ttttttattt tatctttaat   300
ttaatcaaaa gatttagttg tcagaaagaa agaacgaagg gtgagataat gatgatagat   360
```

```
catccatggg ccgccgttaa tagccttttt cagtctctaa gtcaaagtta accctacaga    420
atccatgtct aagtctaaca accataaggt caaagcctcc gtcaattttc agatgcgatt    480
tcagtttatt cctcattgta ataaacccta ttttcagagt aacttgagga tcacgaactt    540
cctccgaatt c                                                         551
```

<210> SEQ ID NO 3
<211> LENGTH: 515
<212> TYPE: DNA
<213> ORGANISM: glycine max

<400> SEQUENCE: 3

```
gagctctgat tcaatcaaac ggttcatgct taatcaagtt gggaacaaca acaacaacaa     60
aaatcaagcc aatgtttgtg ggttttggtt tcatttcatt aagatgatct gtttatctct    120
tttcttcttt ttaaaattta aagtcttcgt attttgtatg taaagatgta aaattatgat    180
tattaggtgg tgcatgtgtc gcgtcatggg ccaatgttat cctctgcttt taagttggaa    240
gaggcccaac tcatgtgtga tgtacggctg tgattgtgta atttaatttg caaaatcaaa    300
aataacacca gagtcatata tatgcatctc tttattttct ctggccccca ccatgtcttc    360
tatgtaatat ttgttgccct cttcccccaa gtatatgaca aggttgggtt tcttttttatc    420
cacgcctgtg cccgttatca cttgctatgg ataattgaaa tccggtgaga gtgagaagtg    480
gggttggctt ggtgggtggg tgggtggatg aattc                               515
```

<210> SEQ ID NO 4
<211> LENGTH: 442
<212> TYPE: DNA
<213> ORGANISM: glycine max

<400> SEQUENCE: 4

```
gagctctgat tgcatttggg caattttgct agcacatgtg atcatcaacg tggtttcaaa     60
aaaacttgtt cctttacagt agtttatctt tgcagagtct taggtgtttg ttttaccagt    120
tatattttga agtgtccgcc gatttcatgt agccgtagcc ttcaaaactg ggttcttgat    180
cggcggtaac attttcgttg ctgtttgttt ttgatgagta ctgttttttg ttttgatggt    240
aaaagtctga gattttcaaa ttcacaagca gccatagggt tttagtccat ttcctttgct    300
gctgaggagg gatgtcttaa atttgcattt aatttataag gaagttttgt taactgttttt    360
ttatggttta ttattccctt tgaatttgaa gccatgtgag tgtgtgaggt gtgcgcctga    420
tctgggattt ttatttgaat tc                                             442
```

<210> SEQ ID NO 5
<211> LENGTH: 459
<212> TYPE: DNA
<213> ORGANISM: glycine max

<400> SEQUENCE: 5

```
gagctctgag gtgttggaga gctaaagctt caagcagaga tggcccttag aaataatgat     60
aaaaactata tgtagtttca aaacttcaaa attatgtagt atgtattatg ttgcactctg    120
gtgtttgtg tctaaacaaa cacccttaga ataaagtggt catttcttgc ccttgagcaa    180
gttcaagtgt tttggacttg tgatgggtgt gttaaggtca tggttgcctt ttatatatat    240
atatatataa atgtttggta attggtcgct tctgtataaa gttcggctag ttaatctgaa    300
ttatgaatct ctgcttataa tattaaacta gtactattgc tggaataaag tgtcagtttt    360
ttctgtttgt tttctttgcc ataatatgcg attttcctct ttgtctttca caattgaagt    420
```

```
cgagggtgcg aaacttcggc atggtggcaa agtgaattc                            459
```

<210> SEQ ID NO 6
<211> LENGTH: 1061
<212> TYPE: DNA
<213> ORGANISM: glycine max

<400> SEQUENCE: 6

```
acgtaaaaat ctctcgttgt ccctaataaa aaagtttcat tacacttatc aaatgacttg     60
gccttgcctc tatttaaacc ctccaaccca tcattaagat ctcaatatct ctcttccttt    120
ctctttattc tctcacacaa aataatggac aagaagcttg gcaacacgtc tcatgatcct    180
gaagtgagaa aggggccatg acaatggaa gaagacttaa tcttgatcac ctatattgcc     240
aatcacgggg aaggggtttg gaactctttg gccaaggctg ctggacttaa acgtaccgga    300
aagagttgcc ggctccggtg gctaaactac ctccgtcctg atgttagaag agggaatatt    360
acacccgagg aacagctttt gatcatgaa cttcatgcaa agtggggaaa caggtggtcc     420
aaaattgcca agcatctacc cggaaggact gataatgaga ttaagaacta ctggaggaca    480
aggatccaga agcacctcaa gcaagcttcc agcagcttcc agcaacagag tagtaattct    540
gagataattt atcatcccca gcttgcact agccaagtgt ccaccatggc gcagcccata     600
gaaacctatt ctccacccag ttatcaagga atgttagatc cattttcaat tcagttccca    660
acaaatcctc atcattctag ttgttgtacc aatgacgacg acaacaacaa ctattggagc    720
atggaggata tctggtcaat gcaattagcc aattactgaa cgggaattaa acctataaac    780
ataaatataa ataatatata taaacctaag tgtctaagtt ccataaatta agctgtagtc    840
tctggcttaa aacatgttag gtttgtttat acaagtagtt ggatgtttgg agtacttcgg    900
tcttttgcgt accatcaata tttaagaact aagttagtta tgttccgtaa cttatgggct    960
cttaattaaa ctatatctgc acaaaattat atatatatca aatgtgatgg tatgtggact   1020
ataaaaagat atggttgaga accacaaact ttgaaacttc g                       1061
```

<210> SEQ ID NO 7
<211> LENGTH: 882
<212> TYPE: DNA
<213> ORGANISM: glycine max

<400> SEQUENCE: 7

```
gaaaagccat ttccatagca gcctaagaaa atgaagagca ctagcttgtt cgctatcttt     60
ctactttgcg ccttcacctc atacctacct tccgccaccg cccaggacgt gctcgacgtg    120
gatggcgatc cgattcggaa cggtttcata tactacgttt tgccggcaat aagaggaaac    180
ggtggcggaa tagaacgagc cgcactcggg aaagacactt gccctatcac tgtagtgcaa    240
tctcccaatc caaactctaa ggggttagaa attaagtttg aatctgcata ccccgcctat    300
tacataaacg aaaccctaat tttgcaaata aagttcagtt acccacagca gtgtgaaaga    360
aagaatcctt ggtgggccat ttctaaggat atatctgaag gaccacctgc tattaaactc    420
tctgggttcc atggtactga actcggttgg tttaaaattc agaaagcttc caaatcctgt    480
gactctaatg actacaagct tgtgttctgc agtatgatg agacctggtg tttggatgtc    540
ggcatttacg tcgatcgtca aggaaacagg cgtttggtgc ttgctgttac tggtgaaccg    600
tttttggttc actttcacaa aattagttct tcaactgcat gaagcagtac cacactggcc    660
caaaaaaaaa aatcatgtgc ttaatttcta gctgtgagag acaattaagt gtatgaccaa    720
```

```
taaaatggtt ttgttgtagg accaagtctg agagacgcca agcaccacat gaataaaata    780
accaaagctt ggtttgtatt gtagccttct ctaatgctat tggtctggtt acatcatctt    840
taattcccct ttatatatgc atatgtttat tatttattga tt                       882
```

<210> SEQ ID NO 8
<211> LENGTH: 1247
<212> TYPE: DNA
<213> ORGANISM: glycine max

<400> SEQUENCE: 8

```
ctcactcact cactcactca ctcactcact cgcaagcaaa aagaaagaat cccaggcgag     60
gagaaagatg gagggaagg agcaggatgt gtcgttggga gcgaacaagt tccccgagag    120
acagccaatt gggacggcgg cgcagagcca agacgacggc aaggactacc aggagccggc    180
gccggcgccg ctggttgacc cgacggagtt tacgtcatgg tcgttttaca gagcagggat    240
agcagagttt gtggccactt ttctgttttct ctacatcact gtcttaaccg ttatgggagt    300
cgccggggct aagtctaagt gtagtaccgt tgggattcaa ggaatcgctt gggccttcgg    360
tggcatgatc ttcgccctcg tttactgcac cgctggcatc tcaggggac acataaaccc    420 ggcggtgaca tttgggctgt ttttggcgag aagttgtcg ttgcccaggg cgattttcta    480
catcgtgatg caatgcttgg gtgctatttg tggcgctggc gtggtgaagg gtttcgaggg    540
gaaaacaaaa tacggtgcgt tgaatggtgg tgccaacttt gttgcccctg ttacaccaa     600 gggtgatggt cttggtgctg agattgttgg cactttcatc cttgtttaca ccgttttctc    660
cgccaccgat gccaaacgta gcgccagaga ctcccacgtc cccatttgg caccttgcc     720 aattgggttc gctgtgttct tggttcactt ggcaaccatc cccatcaccg gaactggtat    780
caaccctgct cgtagtcttg gtgctgctat catcttcaac aaggaccttg ttgggatga     840 acactggatc ttctgggtgg gaccattcat cggtgcagct cttgcagcac tctaccacca    900
ggtcgtaatc agggccattc ccttcaagtc caagtgatc aatcaaacgg ttcatgctta    960
atcaagttgg gaacaacaac aacaacaaaa atcaagccaa tgtttgtggg ttttggtttc   1020
atttcattaa gatgatctgt ttatctcttt tcttctttt aaaattttaaa gtctttgtat   1080 tttgtatgta aagatgtaaa attatgatta ttaggtggtg catgtgtcgc gtcatgggcc   1140
aatgttatcc tctgcttta agttggaaga ggcccaactc atgtgtgatg tacggctgtg   1200
attgtgtaat ttaatttgca aaatcaaaaa taacaccaga gtcatat                 1247
```

<210> SEQ ID NO 9
<211> LENGTH: 1772
<212> TYPE: DNA
<213> ORGANISM: glycine max

<400> SEQUENCE: 9

```
cctcgctcta tttctcagtc tctgtgtttg cggctgagga ttccgaacga gtgaccttct     60
tcgtttctcg caaagtttaa gtaatcatgg gtaaggaaaa ggttcacatc aacattgtcg    120
tcattggaca tgtcgactct gggaagtcaa ctaccactgg tcacttgatc tacaagcttg    180
gaggtattga caagcgtgtg attgagaggt tcgagaagga ggctgccgag atgaacaaga    240
ggtcattcaa gtatgcctgg gtgctcgaca agctcaaagc tgagcgtgaa agaggaatta    300
ccattgatat tgctttgtgg aagtttgaaa ccaccaagta ctactgcacg gtcattgatg    360
ctcctggaca tcgtgacttt atcaagaaca tgattactgg tacctcccag gccgactgtg    420
ctgtccttat tattgactcc accactggtg gttttgaagc tggtattct aaggatggac    480
```

```
agacccgtga gcatgctctt cttgctttca ccctaggtgt gaagcagatg atctgttgct    540
gtaacaagat ggatgccact accccccaagt actctaaggc taggtatgat gaaatcgtga    600
aggaagtctc ttcttacttg aagaaggttg gttacaaccc agacaagatt ccctttgttc    660
ccatctctgg ttttgagggt gacaacatga ttgagaggtc caccaacctt gactggtaca    720
agggaccaac tctccttgag gctcttgacc aaatcaatga gcccaagagg ccctccgaca    780
agcctctaag gcttccattg caggatgtct acaagattgg tggtattggt actgtgccag    840
tgggacgtgt agagactggg gttgtgaagc ctggtatggt ggtgacttt ggtcccactg    900 ggctgacaac tgaggttaag tctgttgaga tgcaccatga ggctctcaca gaggctcttc    960
caggtgacaa tgttggattt aatgtgaaga atgttgcagt caaggatctc aagcgtggtt    1020
ttgttgcatc caactccaag gacgaccctg ccaaggaagc tgccaacttc acatcccaag    1080
tcattatcat gaaccatcct ggccagattg gtaatggata cgcaccagtc cttgactgcc    1140
acacttctca cattgctgtg aagttttctg aaatcttgac caagattgac aggcgatctg    1200
gtaaggagct tgagaaggag cccaaatttt tgaagaatgg tgatgctggt atggttaaga    1260
tggttccaac caagcccatg gtggttgaaa ctttctctga gtatcctccc cttggtcgtt    1320
ttgctgtgag ggacatgcgt cagaccgtag ctgttggagt catcaagagt gttgagaaga    1380
aagaccccac cggagccaag gtcacaaagg ctgccgccaa gaagaagtga ttgcattttg    1440
gcaattttgc tagcacatgt gatcatcaac gtggtttcaa aaaaacttgt tcctttacag    1500
tagtttatct ttgcagagtc ttaggtgttt gttttaccag ttatattttg aagtgtccgc    1560
cgatttcatg tagccgtagc cttcaaaact gggttcttga tcggcggtaa cattttcgtt    1620
gctgtttgtt tttgatgagt actgtttttt gttttgatgg taaaagtctg agattttcaa    1680
attcacaagc agccataggg ttttagtcca tttcctttgc tgctgaggag ggatgtctta    1740
aatttgcatt taatttataa ggaagttttg tt                                   1772
```

<210> SEQ ID NO 10
<211> LENGTH: 574
<212> TYPE: DNA
<213> ORGANISM: glycine max

<400> SEQUENCE: 10

```
gattgttgtg actcgttctt cttcgtcgtt atcttcttct tttgttgttt gtgtgtttgt    60
tttttctctc acctgaaaat gtcttgctgc ggtggtaact gtggttgcgg aagcgcctgc    120
aagtgcggca acggctgcgg aggctgcaag atgtacccag acttgagcta caccgagtca    180
accaccaccg agaccttggt catgggagtg gcaccagtta aggctcaatt cgagagtgct    240
gaaatggggt ttcccgctga gaacgatggc tgcaaatgtg gagctaactg cacctgcaac    300
ccctgcactt gcaagtgagg tgttggagag ctaaagcttc aagcagaaat ggcccttaga    360
aataatgata aaaactatat gtagtttcaa aacttcaaaa ttatgtagta tgtattatgt    420
tgcactctgg tgttttgtgt ctaaacaaac acccttagaa taaagtggtc atttcttgcc    480
cttgagcaag ttcaagtgtt ttggacttgt gatgggtgtg ttaaggtcat ggttgccttt    540
tttttatata tatatatata tataaatgtt tggt                                  574
```

<210> SEQ ID NO 11
<211> LENGTH: 204
<212> TYPE: PRT
<213> ORGANISM: glycine max

<400> SEQUENCE: 11

Met Asp Lys Lys Leu Gly Asn Thr Ser His Asp Pro Glu Val Arg Lys
1               5                   10                  15

Gly Pro Trp Thr Met Glu Glu Asp Leu Ile Leu Ile Thr Tyr Ile Ala
            20                  25                  30

Asn His Gly Glu Gly Val Trp Asn Ser Leu Ala Lys Ala Ala Gly Leu
        35                  40                  45

Lys Arg Thr Gly Lys Ser Cys Arg Leu Arg Trp Leu Asn Tyr Leu Arg
50                  55                  60

Pro Asp Val Arg Arg Gly Asn Ile Thr Pro Glu Glu Gln Leu Leu Ile
65                  70                  75                  80

Met Glu Leu His Ala Lys Trp Gly Asn Arg Trp Ser Lys Ile Ala Lys
                85                  90                  95

His Leu Pro Gly Arg Thr Asp Asn Glu Ile Lys Asn Tyr Trp Arg Thr
            100                 105                 110

Arg Ile Gln Lys His Leu Lys Gln Ala Ser Ser Phe Gln Gln Gln
        115                 120                 125

Ser Ser Asn Ser Glu Ile Ile Tyr His Pro Gln Ala Cys Thr Ser Gln
130                 135                 140

Val Ser Thr Met Ala Gln Pro Ile Glu Thr Tyr Ser Pro Pro Ser Tyr
145                 150                 155                 160

Gln Gly Met Leu Asp Pro Phe Ser Ile Gln Phe Pro Thr Asn Pro His
                165                 170                 175

His Ser Ser Cys Cys Thr Asn Asp Asp Asn Asn Asn Tyr Trp Ser
            180                 185                 190

Met Glu Asp Ile Trp Ser Met Gln Leu Ala Asn Tyr
        195                 200

<210> SEQ ID NO 12
<211> LENGTH: 203
<212> TYPE: PRT
<213> ORGANISM: glycine max

<400> SEQUENCE: 12

Met Lys Ser Thr Ser Leu Phe Ala Ile Phe Leu Leu Cys Ala Phe Thr
1               5                   10                  15

Ser Tyr Leu Pro Ser Ala Thr Ala Gln Asp Val Leu Asp Val Asp Gly
            20                  25                  30

Asp Pro Ile Arg Asn Gly Phe Ile Tyr Tyr Val Leu Pro Ala Ile Arg
        35                  40                  45

Gly Asn Gly Gly Gly Ile Glu Arg Ala Ala Leu Gly Lys Asp Thr Cys
50                  55                  60

Pro Ile Thr Val Val Gln Ser Pro Asn Pro Asn Ser Lys Gly Leu Glu
65                  70                  75                  80

Ile Lys Phe Glu Ser Ala Tyr Pro Ala Tyr Tyr Ile Asn Glu Thr Leu
                85                  90                  95

Ile Leu Gln Ile Lys Phe Ser Tyr Pro Gln Gln Cys Glu Arg Lys Asn
            100                 105                 110

Pro Trp Trp Ala Ile Ser Lys Asp Ile Ser Glu Gly Pro Pro Ala Ile
        115                 120                 125

Lys Leu Ser Gly Phe His Gly Thr Glu Leu Gly Trp Phe Lys Ile Gln
130                 135                 140

Lys Ala Ser Lys Ser Cys Asp Ser Asn Asp Tyr Lys Leu Val Phe Cys
145                 150                 155                 160

```
Gln Tyr Asp Glu Thr Trp Cys Leu Asp Val Gly Ile Tyr Val Asp Arg
                165                 170                 175

Gln Gly Asn Arg Arg Leu Val Leu Ala Val Thr Gly Glu Pro Phe Leu
            180                 185                 190

Val His Phe His Lys Ile Ser Ser Ser Thr Ala
        195                 200

<210> SEQ ID NO 13
<211> LENGTH: 289
<212> TYPE: PRT
<213> ORGANISM: glycine max

<400> SEQUENCE: 13

Met Glu Gly Lys Glu Gln Asp Val Ser Leu Gly Ala Asn Lys Phe Pro
1               5                   10                  15

Glu Arg Gln Pro Ile Gly Thr Ala Ala Gln Ser Gln Asp Gly Lys
            20                  25                  30

Asp Tyr Gln Glu Pro Ala Pro Ala Pro Leu Val Asp Pro Thr Glu Phe
        35                  40                  45

Thr Ser Trp Ser Phe Tyr Arg Ala Gly Ile Ala Glu Phe Val Ala Thr
    50                  55                  60

Phe Leu Phe Leu Tyr Ile Thr Val Leu Thr Val Met Gly Val Ala Gly
65                  70                  75                  80

Ala Lys Ser Lys Cys Ser Thr Val Gly Ile Gln Gly Ile Ala Trp Ala
                85                  90                  95

Phe Gly Gly Met Ile Phe Ala Leu Val Tyr Cys Thr Ala Gly Ile Ser
            100                 105                 110

Gly Gly His Ile Asn Pro Ala Val Thr Phe Gly Leu Phe Leu Ala Arg
        115                 120                 125

Lys Leu Ser Leu Pro Arg Ala Ile Phe Tyr Ile Val Met Gln Cys Leu
    130                 135                 140

Gly Ala Ile Cys Gly Ala Gly Val Val Lys Gly Phe Glu Gly Lys Thr
145                 150                 155                 160

Lys Tyr Gly Ala Leu Asn Gly Gly Ala Asn Phe Val Ala Pro Gly Tyr
                165                 170                 175

Thr Lys Gly Asp Gly Leu Gly Ala Glu Ile Val Gly Thr Phe Ile Leu
            180                 185                 190

Val Tyr Thr Val Phe Ser Ala Thr Asp Ala Lys Arg Ser Ala Arg Asp
        195                 200                 205

Ser His Val Pro Ile Leu Ala Pro Leu Pro Ile Gly Phe Ala Val Phe
    210                 215                 220

Leu Val His Leu Ala Thr Ile Pro Ile Thr Gly Thr Gly Ile Asn Pro
225                 230                 235                 240

Ala Arg Ser Leu Gly Ala Ala Ile Ile Phe Asn Lys Asp Leu Gly Trp
                245                 250                 255

Asp Glu His Trp Ile Phe Trp Val Gly Pro Phe Ile Gly Ala Ala Leu
            260                 265                 270

Ala Ala Leu Tyr His Gln Val Val Ile Arg Ala Ile Pro Phe Lys Ser
        275                 280                 285

Lys

<210> SEQ ID NO 14
<211> LENGTH: 447
<212> TYPE: PRT
<213> ORGANISM: glycine max
```

```
<400> SEQUENCE: 14

Met Gly Lys Glu Lys Val His Ile Asn Ile Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Val Ile Glu Arg Phe Glu Lys Glu Ala Ala Glu
        35                  40                  45

Met Asn Lys Arg Ser Phe Lys Tyr Ala Trp Val Leu Asp Lys Leu Lys
50                  55                  60

Ala Glu Arg Glu Arg Gly Ile Thr Ile Asp Ile Ala Leu Trp Lys Phe
65                  70                  75                  80

Glu Thr Thr Lys Tyr Tyr Cys Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Ile Asp Ser Thr Thr Gly Gly Phe Glu Ala Gly Ile Ser
        115                 120                 125

Lys Asp Gly Gln Thr Arg Glu His Ala Leu Leu Ala Phe Thr Leu Gly
130                 135                 140

Val Lys Gln Met Ile Cys Cys Cys Asn Lys Met Asp Ala Thr Thr Pro
145                 150                 155                 160

Lys Tyr Ser Lys Ala Arg Tyr Asp Glu Ile Val Lys Glu Val Ser Ser
                165                 170                 175

Tyr Leu Lys Lys Val Gly Tyr Asn Pro Asp Lys Ile Pro Phe Val Pro
            180                 185                 190

Ile Ser Gly Phe Glu Gly Asp Asn Met Ile Glu Arg Ser Thr Asn Leu
        195                 200                 205

Asp Trp Tyr Lys Gly Pro Thr Leu Leu Glu Ala Leu Asp Gln Ile Asn
210                 215                 220

Glu Pro Lys Arg Pro Ser Asp Lys Pro Leu Arg Leu Pro Leu Gln Asp
225                 230                 235                 240

Val Tyr Lys Ile Gly Gly Ile Gly Thr Val Pro Val Gly Arg Val Glu
                245                 250                 255

Thr Gly Val Val Lys Pro Gly Met Val Val Thr Phe Gly Pro Thr Gly
            260                 265                 270

Leu Thr Thr Glu Val Lys Ser Val Glu Met His His Glu Ala Leu Thr
        275                 280                 285

Glu Ala Leu Pro Gly Asp Asn Val Gly Phe Asn Val Lys Asn Val Ala
290                 295                 300

Val Lys Asp Leu Lys Arg Gly Phe Val Ala Ser Asn Ser Lys Asp Asp
305                 310                 315                 320

Pro Ala Lys Glu Ala Ala Asn Phe Thr Ser Gln Val Ile Ile Met Asn
                325                 330                 335

His Pro Gly Gln Ile Gly Asn Gly Tyr Ala Pro Val Leu Asp Cys His
            340                 345                 350

Thr Ser His Ile Ala Val Lys Phe Ser Glu Ile Leu Thr Lys Ile Asp
        355                 360                 365

Arg Arg Ser Gly Lys Glu Leu Glu Lys Glu Pro Lys Phe Leu Lys Asn
370                 375                 380

Gly Asp Ala Gly Met Val Lys Met Val Pro Thr Lys Pro Met Val Val
385                 390                 395                 400

Glu Thr Phe Ser Glu Tyr Pro Pro Leu Gly Arg Phe Ala Val Arg Asp
                405                 410                 415
```

```
Met Arg Gln Thr Val Ala Val Gly Val Ile Lys Ser Val Glu Lys Lys
            420                 425                 430

Asp Pro Thr Gly Ala Lys Val Thr Lys Ala Ala Ala Lys Lys Lys
            435                 440                 445
```

<210> SEQ ID NO 15
<211> LENGTH: 79
<212> TYPE: PRT
<213> ORGANISM: glycine max

<400> SEQUENCE: 15

```
Met Ser Cys Cys Gly Gly Asn Cys Gly Cys Gly Ser Ala Cys Lys Cys
1               5                   10                  15

Gly Asn Gly Cys Gly Gly Cys Lys Met Tyr Pro Asp Leu Ser Tyr Thr
            20                  25                  30

Glu Ser Thr Thr Thr Glu Thr Leu Val Met Gly Val Ala Pro Val Lys
        35                  40                  45

Ala Gln Phe Glu Ser Ala Glu Met Gly Val Pro Ala Glu Asn Asp Gly
    50                  55                  60

Cys Lys Cys Gly Ala Asn Cys Thr Cys Asn Pro Cys Thr Cys Lys
65                  70                  75
```

<210> SEQ ID NO 16
<211> LENGTH: 17
<212> TYPE: DNA
<213> ORGANISM: glycine max

<400> SEQUENCE: 16
gatccatttt caattca                                                          17

<210> SEQ ID NO 17
<211> LENGTH: 17
<212> TYPE: DNA
<213> ORGANISM: glycine max

<400> SEQUENCE: 17
gatcgtcaag gaaacag                                                          17

<210> SEQ ID NO 18
<211> LENGTH: 17
<212> TYPE: DNA
<213> ORGANISM: glycine max

<400> SEQUENCE: 18
gatctgttta tctcttt                                                          17

<210> SEQ ID NO 19
<211> LENGTH: 17
<212> TYPE: DNA
<213> ORGANISM: glycine max

<400> SEQUENCE: 19
gatcggcggt aacattt                                                          17

<210> SEQ ID NO 20
<211> LENGTH: 24
<212> TYPE: DNA
<213> ORGANISM: artificial
<220> FEATURE:
<223> OTHER INFORMATION: sense primer for qRT-PCR endogenous control
      ATPS

<400> SEQUENCE: 20
catgattggg agaaaccttta agct        24

<210> SEQ ID NO 21
<211> LENGTH: 20
<212> TYPE: DNA
<213> ORGANISM: artificial
<220> FEATURE:
<223> OTHER INFORMATION: antisense primer for qRT-PCR endogenous control
      ATPS

<400> SEQUENCE: 21
agattgggcc agaggatcct        20

<210> SEQ ID NO 22
<211> LENGTH: 21
<212> TYPE: DNA
<213> ORGANISM: artificial
<220> FEATURE:
<223> OTHER INFORMATION: sense primer for qRT-PCR analysis of PSO323364
      gene

<400> SEQUENCE: 22
caaggctgct ggacttaaac g        21

<210> SEQ ID NO 23
<211> LENGTH: 24
<212> TYPE: DNA
<213> ORGANISM: artificial
<220> FEATURE:
<223> OTHER INFORMATION: antisense primer for qRT-PCR analysis of
      PSO323364 gene

<400> SEQUENCE: 23
acatcaggac ggaggtagtt tagc        24

<210> SEQ ID NO 24
<211> LENGTH: 20
<212> TYPE: DNA
<213> ORGANISM: artificial
<220> FEATURE:
<223> OTHER INFORMATION: sense primer for qRT-PCR analysis of PSO400362
      gene

<400> SEQUENCE: 24
ggtgtttgga tgtcggcatt        20

<210> SEQ ID NO 25
<211> LENGTH: 21
<212> TYPE: DNA
<213> ORGANISM: artificial
<220> FEATURE:
<223> OTHER INFORMATION: antisense primer for qRT-PCR analysis of
      PSO400362 gene

<400> SEQUENCE: 25
caccagtaac agcaagcacc a        21

<210> SEQ ID NO 26
<211> LENGTH: 18
<212> TYPE: DNA
<213> ORGANISM: artificial
<220> FEATURE:
<223> OTHER INFORMATION: sense primer for qRT-PCR analysis of PSE332986
      gene

<400> SEQUENCE: 26

```
tggtgcatgt gtcgcgtc                                                   18

<210> SEQ ID NO 27
<211> LENGTH: 20
<212> TYPE: DNA
<213> ORGANISM: artificial
<220> FEATURE:
<223> OTHER INFORMATION: antisense primer for qRT-PCR analysis of
      PSO332986 gene

<400> SEQUENCE: 27
catcacacat gagttgggcc                                                 20

<210> SEQ ID NO 28
<211> LENGTH: 19
<212> TYPE: DNA
<213> ORGANISM: artificial
<220> FEATURE:
<223> OTHER INFORMATION: sense primer for qRT-PCR analysis of PSO333268
      gene

<400> SEQUENCE: 28
agtgtccgcc gatttcatg                                                  19

<210> SEQ ID NO 29
<211> LENGTH: 20
<212> TYPE: DNA
<213> ORGANISM: artificial
<220> FEATURE:
<223> OTHER INFORMATION: antisense primer for qRT-PCR analysis of
      PSO333268 gene

<400> SEQUENCE: 29
aacgaaaatg ttaccgccga                                                 20

<210> SEQ ID NO 30
<211> LENGTH: 20
<212> TYPE: DNA
<213> ORGANISM: artificial
<220> FEATURE:
<223> OTHER INFORMATION: sense primer for qRT-PCR analysis of PSO333209
      gene

<400> SEQUENCE: 30
tcatgggagt ggcaccagtt                                                 20

<210> SEQ ID NO 31
<211> LENGTH: 19
<212> TYPE: DNA
<213> ORGANISM: artificial
<220> FEATURE:
<223> OTHER INFORMATION: antisense primer for qRT-PCR analysis of
      PSO333209 gene

<400> SEQUENCE: 31
tcgttctcag cgggaacac                                                  19

<210> SEQ ID NO 32
<211> LENGTH: 5232
<212> TYPE: DNA
<213> ORGANISM: artificial
<220> FEATURE:
<223> OTHER INFORMATION: DNA construct QC315

<400> SEQUENCE: 32
catggcccac agcaagcacg gcctgaagga ggagatgacc atgaagtacc acatggaggg    60
```

```
ctgcgtgaac ggccacaagt tcgtgatcac cggcgagggc atcggctacc ccttcaaggg    120
caagcagacc atcaacctgt gcgtgatcga gggcggcccc ctgcccttca gcaggacat    180 cctgagcgcc ggcttcaagt acggcgaccg gatcttcacc gagtacccc aggacatcgt    240 ggactacttc aagaacagct gccccgccgg ctacacctgg ggccgagct tcctgttcga    300 ggacggcgcc gtgtgcatct gtaacgtgga catcaccgtg agcgtgaagg agaactgcat    360
ctaccacaag agcatcttca cggcgtgaa cttccccgcc gacggccccg tgatgaagaa    420
gatgaccacc aactgggagg ccagctgcga agatcatg cccgtgccta gcagggcat    480 cctgaagggc gacgtgagca tgtacctgct gctgaaggac ggcggccggt accggtgcca    540
gttcgacacc gtgtacaagg ccaagagcgt gcccagcaag atgcccgagt ggcacttcat    600
ccagcacaag ctgctgcggg aggaccggag cgacgccaag aaccagaagt ggcagctgac    660
cgagcacgcc atcgccttcc ccagcgccct ggcctgagag ctcgaatttc cccgatcgtt    720
caaacatttg gcaataaagt ttcttaagat tgaatcctgt tgccggtctt gcgatgatta    780
tcatataatt tctgttgaat tacgttaagc atgtaataat taacatgtaa tgcatgacgt    840
tatttatgag atgggttttt atgattagag tcccgcaatt atacatttaa tacgcgatag    900
aaaacaaaat atagcgcgca aactaggata aattatcgcg cgcggtgtca tctatgttac    960
tagatcggga attctagtgg ccggcccagc tgatatccat cacactggcg gccgcactcg   1020
actgaattgg ttccggcgcc agcctgcttt tttgtacaaa gttggcatta taaaaagca   1080 ttgcttatca atttgttgca acgaacaggt cactatcagt caaaataaaa tcattatttg   1140
gggcccgagc ttaagtaact aactaacagg aagagtttgt agaaacgcaa aaaggccatc   1200
cgtcaggatg gccttctgct tagtttgatg cctggcagtt tatggcgggc gtcctgcccg   1260
ccaccctccg ggccgttgct tcacaacgtt caaatccgct cccggcggat ttgtcctact   1320
caggagagcg ttcaccgaca acaacagat aaaacgaaag gcccagtctt ccgactgagc   1380
ctttcgtttt atttgatgcc tggcagttcc ctactctcgc ttagtagtta gacgtccccg   1440
agatccatgc tagcggtaat acggttatcc acagaatcag gggataacgc aggaaagaac   1500
atgtgagcaa aaggccagca aaaggccagg aaccgtaaaa aggccgcgtt gctggcgttt   1560
ttccataggc tccgcccccc tgacgagcat cacaaaaatc gacgctcaag tcagaggtgg   1620
cgaaacccga caggactata agataccag gcgtttcccc ctggaagctc cctcgtgcgc   1680
tctcctgttc cgacccctgcc gcttaccgga tacctgtccg cctttctccc ttcgggaagc   1740
gtggcgcttt ctcatagctc acgctgtagg tatctcagtt cggtgtaggt cgttcgctcc   1800
aagctgggct gtgtgcacga accccccgtt cagcccgacc gctgcgcctt atccggtaac   1860
tatcgtcttg agtccaaccc ggtaagacac gacttatcgc cactggcagc agccactggt   1920
aacaggatta gcagagcgag gtatgtaggc ggtgctacag agttcttgaa gtggtggcct   1980
aactacggct acactagaag aacagtattt ggtatctgcg ctctgctgaa gccagttacc   2040
ttcggaaaaa gagttggtag ctcttgatcc ggcaaacaaa ccaccgctgg tagcggtggt   2100
ttttttgttt gcaagcagca gattacgcgc agaaaaaaag gatctcaaga agatcctttg   2160
atcttttcta cggggtctga cgctcagtgg aacgggccc aatctgaata atgttacaac   2220
caattaacca attctgatta gaaaaactca tcgagcatca aatgaaactg caatttattc   2280
atatcaggat tatcaatacc atattttga aaaagccgtt tctgtaatga aggagaaaac   2340
tcaccgaggc agttccatag gatggcaaga tcctggtatc ggtctgcgat tccgactcgt   2400
```

```
ccaacatcaa tacaacctat taatttcccc tcgtcaaaaa taaggttatc aagtgagaaa      2460
tcaccatgag tgacgactga atccggtgag aatggcaaaa gtttatgcat ttctttccag      2520
acttgttcaa caggccagcc attacgctcg tcatcaaaat cactcgcatc aaccaaaccg      2580
ttattcattc gtgattgcgc ctgagcgaga cgaaatacgc gatcgctgtt aaaaggacaa      2640
ttacaaacag gaatcgaatg caaccggcgc aggaacactg ccagcgcatc aacaatattt      2700
tcacctgaat caggatattc ttctaatacc tggaatgctg tttttccggg gatcgcagtg      2760
gtgagtaacc atgcatcatc aggagtacgg ataaaatgct tgatggtcgg aagaggcata      2820
aattccgtca gccagtttag tctgaccatc tcatctgtaa catcattggc aacgctacct      2880
ttgccatgtt tcagaaacaa ctctggcgca tcgggcttcc catacaagcg atagattgtc      2940
gcacctgatt gcccgacatt atcgcgagcc catttatacc catataaatc agcatccatg      3000
ttggaattta atcgcggcct cgacgtttcc cgttgaatat ggctcataac accccttgta      3060
ttactgttta tgtaagcaga cagttttatt gttcatgatg atatattttt atcttgtgca      3120
atgtaacatc agagattttg agacacgggc cagagctgca gctggatggc aaataatgat      3180
tttattttga ctgatagtga cctgttcgtt gcaacaaatt gataagcaat gctttcttat      3240
aatgccaact ttgtacaaga aagctgggtc tagatatctc gacccgggtg attgcggtta      3300
catcatgtac ggaaaaataa ttctaatcct tgatttaaat ttgaacttga ctatttattt      3360
attctttatt tcattttgta aatcatttta tgtatctcct ggcaagcaat tttatccacc      3420
ttgcaccaac accttcgggt tccataatca aaccaccttä acttcacacc atgctgtaac      3480
tcacaccgcc cagcatctcc aatgtgaaag aagctaaaat ttaataaaca atcatacgaa      3540
gcagtgacaa ataccagatg gtattaatg cttcgataaa attaattgga aagtataaaa      3600
tggtagaaaa taataaatta taattaattt aagtaagata aaaaataatt aaaaactaaa      3660
atgttaaaat tttaaaaaaa ttattttaaa taatatttaa aaacattaaa aatcattta      3720 aaaaatttat ttatagaaca attaaataaa tatttcagct aataaaaaac aaaagcttac      3780
ctagccttag aagacaactt gtccaacaat tagatgatac ccattgccct tacgttttct      3840
ttaacatcaa ttattgtttt tgtcaacaag ctatctttta gttttatttt attggtaaaa      3900
aatatgtcgc cttcaagttg catcatttaa cacatctcgt cattagaaaa ataaaactct      3960
tccctaaacg attagtagaa aaaatcattc gataataaat aagaaagaaa aattagaaaa      4020
aaataacttc atttttaaaaa aatcattaag gctatatttt ttaaatgact aattttatat      4080
agactgtaac taaaagtata caattttatta tgctatgtat cttaaagaat tacttataaa      4140
aatctacgga agaatatctt acaaagtgaa aaacaaatga gaaagaattt agtgggatga      4200
ttatgatttt atttgaaaat tgaaaaaata attattaaag actttagtgg agtaagaaag      4260
ctttcctatt agtctttct tatccataaa aaaaaaaaa aaaatctagc gtgacagctt      4320
ttccatagat tttaataatg taaaatactg gtagcagccg accgttcagg taatggacac      4380
tgtggtccta acttgcaacg ggtgcgggcc caatttaata cgccgtggt aacggataaa      4440 gccaagcgtg aagcggtgaa ggtacatctc tgactccgtc aagattacga aaccgtcaac      4500
tacgaaggac tccccgaaat atcatctgtg tcataaacac caagtcacac catacatggg      4560
cacgcgtcac aatatgattg gagaacggtt ccaccgcata tgctataaaa tgcccccaca      4620
cccctcgacc ctaatcgcac ttcaattgca atcaaattag ttcattctct ttgcgcagtt      4680
ccctacctct ccttcaagg ttcgtagatt tcttccgttt ttttttcttc ttctttattg      4740
tttgttctac atcagcatga tgttgatttg attgtgtttt ctatcgtttc atcgattata      4800
```

```
aattttcata atcagaagat tcagctttta ttaatgcaag aacgtcctta attgatgatt    4860
ttataaccgt aaattaggtc taattagagt tttttttcata aagattttca gatccgttta    4920
caacaagcct taattgttga ttctgtagtc gtagattaag gttttttttca tgaactactt    4980 cagatccgtt aaacaacagc cttatttgtt gatacttcag tcgttttca agaaattgtt    5040 cagatccgtt gataaaagcc ttattcgttg attctgtatg gtatttcaag agatattgct    5100
caggtccttt agcaactacc ttatttgttg attctgtggc catagattag gattttttt    5160 cacgaaattg cttcttgaaa ttacgtgatg gattttgatt ctgatttatc ttgtgattgt    5220
tgactctaca gc                                                         5232

<210> SEQ ID NO 33
<211> LENGTH: 5492
<212> TYPE: DNA
<213> ORGANISM: artificial
<220> FEATURE:
<223> OTHER INFORMATION: DNA construct QC327

<400> SEQUENCE: 33
ctgaacggga attaaaccta taaacataaa tataaataat atatataaac ctaagtgtct      60
aagttccata aattaagctg tagtctctgg cttaaaacat gttaggtttg tttatacaag     120
tagttggatg tttggagtac ttcggtcttt tgcgtaccat caatatttaa gaactaagtt     180
agttatgttc cgtaacttat gggctcttaa ttaaactata tctgcacaaa attatatata     240
tatcaaatgt gatggtatgt ggactataaa aagatatggt tgagaaccac aaactttgaa     300
acttcgaata atatattgcc agtgacagtc ttgttgattt gttatagcaa gtcctatttt     360
cttaatcatt gctttgtttt aacgtaccta gatttcataa cttttgtctt tgtctcaagc     420
tgaacctaat gatgatagta atattaactt attgtatagg gtatttcat aggataaaaa     480 atgatgtgca attacgtgta gaccaaatat tacttgatga cagatggaat tctagtggcc     540
ggcccagctg atatccatca cactggcggc cgcactcgac tgaattggtt ccggcgccag     600
cctgcttttt tgtacaaagt tggcattata aaaaagcatt gcttatcaat ttgttgcaac     660
gaacaggtca ctatcagtca aaataaaatc attatttggg gcccgagctt aagtaactaa     720
ctaacaggaa gagtttgtag aaacgcaaaa aggccatccg tcaggatggc cttctgctta     780
gtttgatgcc tggcagtta tggcgggcgt cctgcccgcc accctccggg ccgttgcttc     840
acaacgttca aatccgctcc cggcggattt gtcctactca ggagagcgtt caccgacaaa     900
caacagataa aacgaaaggc ccagtcttcc gactgagcct ttcgttttat ttgatgcctg     960
gcagttccct actctcgctt agtagttaga cgtccccgag atccatgcta gcggtaatac    1020
ggttatccac agaatcaggg gataacgcag gaaagaacat gtgagcaaaa ggccagcaaa    1080
aggccaggaa ccgtaaaaag gccgcgttgc tggcgttttt ccataggctc cgccccctg    1140 acgagcatca caaaaatcga cgctcaagtc agaggtggcg aaacccgaca ggactataaa    1200
gataccaggc gtttccccct ggaagctccc tcgtgcgctc tcctgttccg accctgccgc    1260
ttaccggata cctgtccgcc tttctccctt cgggaagcgt ggcgctttct catagctcac    1320
gctgtaggta tctcagttcg gtgtaggtcg ttcgctccaa gctgggctgt gtgcacgaac    1380
cccccgttca gcccgaccgc tgcgccttat ccggtaacta tcgtcttgag tccaacccgg    1440
taagacacga cttatcgcca ctggcagcag ccactggtaa caggattagc agagcgaggt    1500
atgtaggcgg tgctacagag ttcttgaagt ggtggcctaa ctacggctac actagaagaa    1560
```

```
cagtatttgg tatctgcgct ctgctgaagc cagttacctt cggaaaaaga gttggtagct    1620
cttgatccgg caaacaaacc accgctggta gcggtggttt ttttgtttgc aagcagcaga    1680
ttacgcgcag aaaaaaagga tctcaagaag atcctttgat ctttttctacg gggtctgacg    1740 ctcagtggaa cggggcccaa tctgaataat gttacaacca attaccaat tctgattaga     1800 aaaactcatc gagcatcaaa tgaaactgca atttattcat atcaggatta tcaataccat    1860 attttgaaa aagccgtttc tgtaatgaag gagaaaactc accgaggcag ttccatagga     1920
tggcaagatc ctggtatcgg tctgcgattc cgactcgtcc aacatcaata caacctatta    1980
atttcccctc gtcaaaaata aggttatcaa gtgagaaatc accatgagtg acgactgaat    2040
ccggtgagaa tggcaaaagt ttatgcattt cttttccagac ttgttcaaca ggccagccat    2100
tacgctcgtc atcaaaatca ctcgcatcaa ccaaaccgtt attcattcgt gattgcgcct    2160
gagcgagacg aaatacgcga tcgctgttaa aaggacaatt acaaacagga atcgaatgca    2220
accggcgcag gaacactgcc agcgcatcaa caatattttc acctgaatca ggatattctt    2280
ctaatacctg gaatgctgtt tttccgggga tcgcagtggt gagtaaccat gcatcatcag    2340
gagtacggat aaaatgcttg atggtcggaa gaggcataaa ttccgtcagc cagtttagtc    2400
tgaccatctc atctgtaaca tcattggcaa cgctacctttt gccatgtttc agaaacaact    2460
ctggcgcatc gggcttccca tacaagcgat agattgtcgc acctgattgc ccgacattat    2520
cgcgagccca tttatacccca tataaatcag catccatgtt ggaatttaat cgcggcctcg    2580
acgtttcccg ttgaatatgg ctcataacac cccttgtatt actgtttatg taagcagaca    2640
gttttattgt tcatgatgat atatttttat cttgtgcaat gtaacatcag agattttgag    2700
acacgggcca gagctgcagc tggatggcaa ataatgattt tattttgact gatagtgacc    2760
tgttcgttgc aacaaattga taagcaatgc tttcttataa tgccaacttt gtacaagaaa    2820
gctgggtcta gatatctcga cccgggtgat tgcggttaca tcatgtacgg aaaaataatt    2880
ctaatccttg atttaaattt gaacttgact atttatttat tctttatttc attttgtaaa    2940
tcattttatg tatctcctgg caagcaattt tatccaccttt gcaccaacac cttcgggttc    3000
cataatcaaa ccaccttaac ttcacaccat gctgtaactc acaccgccca gcatctccaa    3060
tgtgaaagaa gctaaaattt aataaacaat catacgaagc agtgacaaaa taccagatgg    3120
tattaatgct tcgataaaat taattggaaa gtataaaatg gtagaaaata ataaattata    3180
attaatttaa gtaagataaa aaataattaa aaactaaaat gttaaaattt taaaaaaatt    3240 atttaaata atatttaaaa acattaaaaa tcattttaaa aaatttattt atagaacaat    3300
taaataaata tttcagctaa taaaaaacaa aagcttacct agccttagaa gacaacttgt    3360
ccaacaatta gatgataccc attgcccta cgttttcttt aacatcaatt attgttttg     3420 tcaacaagct atcttttagt tttattttat tggtaaaaaa tatgtcgcct tcaagttgca    3480
tcatttaaca catctcgtca ttagaaaaat aaaactcttc cctaaacgat tagtagaaaa    3540
aatcattcga taataaataa gaaagaaaaa ttagaaaaaa ataacttcat tttaaaaaaa    3600
tcattaaggc tatatttttt aaatgactaa ttttatatag actgtaacta aaagtataca    3660
atttattatg ctatgtatct taagaattca cttataaaaa tctacggaag aatatcttac    3720
aaagtgaaaa acaaatgaga aagaatttag tgggatgatt atgattttat ttgaaaattg    3780
aaaaaataat tattaaagac tttagtggag taagaaagct ttcctattag tcttttctta    3840
tccataaaaa aaaaaaaaa aatctagcgt gacagctttt ccatagattt taataatgta    3900
aaatactggt agcagccgac cgttcaggta atggacactg tggtcctaac ttgcaacggg    3960
```

```
tgcgggccca atttaataac gccgtggtaa cggataaagc caagcgtgaa gcggtgaagg   4020
tacatctctg actccgtcaa gattacgaaa ccgtcaacta cgaaggactc cccgaaatat   4080
catctgtgtc ataaacacca agtcacacca tacatgggca cgcgtcacaa tatgattgga   4140
gaacggttcc accgcatatg ctataaaatg ccccacacc cctcgaccct aatcgcactt    4200
caattgcaat caaattagtt cattctcttt gcgcagttcc ctacctctcc tttcaaggtt   4260
cgtagatttc ttccgttttt ttttcttctt ctttattgtt tgttctacat cagcatgatg   4320
ttgatttgat tgtgttttct atcgtttcat cgattataaa ttttcataat cagaagattc   4380
agcttttatt aatgcaagaa cgtccttaat tgatgatttt ataaccgtaa attaggtcta   4440
attagagttt ttttcataaa gattttcaga tccgtttaca acaagcctta attgttgatt   4500
ctgtagtcgt agattaaggt tttttcatg aactacttca gatccgttaa acaacagcct    4560
tatttgttga tacttcagtc gttttttcaag aaattgttca gatccgttga taaaagcctt   4620
attcgttgat tctgtatggt atttcaagag atattgctca ggtcctttag caactacctt   4680
atttgttgat tctgtggcca tagattagga ttttttttca cgaaattgct tcttgaaatt   4740
acgtgatgga ttttgattct gatttatctt gtgattgttg actctacagc catggcccac   4800
agcaagcacg gcctgaagga ggagatgacc atgaagtacc acatggaggg ctgcgtgaac   4860
ggccacaagt tcgtgatcac cggcgagggc atcggctacc ccttcaaggg caagcagacc   4920
atcaacctgt gcgtgatcga gggcggcccc ctgcccttca gcgaggacat cctgagcgcc   4980
ggcttcaagt acggcgaccg gatcttcacc gagtaccccc aggacatcgt ggactacttc   5040
aagaacagct gccccgccgg ctacacctgg ggccggagct tcctgttcga ggacggcgcc   5100
gtgtgcatct gtaacgtgga catcaccgtg agcgtgaagg agaactgcat ctaccacaag   5160
agcatcttca acggcgtgaa cttccccgcc gacggccccg tgatgaagaa gatgaccacc   5220
aactgggagg ccagctgcga aagatcatg cccgtgccta gcagggcat cctgaagggc     5280 gacgtgagca tgtacctgct gctgaaggac ggcggccggt accggtgcca gttcgacacc   5340
gtgtacaagg ccaagagcgt gcccagcaag atgcccgagt ggcacttcat ccagcacaag   5400
ctgctgcggg aggaccggag cgacgccaag aaccagaagt ggcagctgac cgagcacgcc   5460
atcgccttcc ccagcgccct ggcctgagag ct                                  5492
```

<210> SEQ ID NO 34
<211> LENGTH: 8409
<212> TYPE: DNA
<213> ORGANISM: artificial
<220> FEATURE:
<223> OTHER INFORMATION: DNA construct QC324i

<400> SEQUENCE: 34

```
atcaaccact ttgtacaaga aagctgaacg agaaacgtaa aatgatataa atatcaatat     60
attaaattag attttgcata aaaaacagac tacataatac tgtaaaacac aacatatcca    120
gtcactatgg tcgacctgca gactggctgt gtataaggga gcctgacatt tatattcccc    180
agaacatcag gttaatggcg ttttgatgt cattttcgcg gtggctgaga tcagccactt     240
cttccccgat aacggagacc ggcacactgg ccatatcggg ggtcatcatg cgccagcttt    300
catccccgat atgcaccacc gggtaaagtt cacgggagac tttatctgac agcagacgtg    360
cactggccag ggggatcacc atccgtcgcc cgggcgtgtc aataatatca ctctgtacat    420
ccacaaacag acgataacgg ctctctcttt tataggtgta aaccttaaac tgcatttcac    480
```

| | |
|---|---|
| cagcccctgt tctcgtcagc aaaagagccg ttcatttcaa taaaccgggc gacctcagcc | 540 |
| atcccttcct gattttccgc tttccagcgt tcggcacgca gacgacgggc ttcattctgc | 600 |
| atggttgtgc ttaccagacc ggagatattg acatcatata tgccttgagc aactgatagc | 660 |
| tgtcgctgtc aactgtcact gtaatacgct gcttcatagc atacctcttt ttgacatact | 720 |
| tcgggtatac atatcagtat atattcttat accgcaaaaa tcagcgcgca aatacgcata | 780 |
| ctgttatctg gcttttagta agccggatcc agatctttac gccccgccct gccactcatc | 840 |
| gcagtactgt tgtaattcat taagcattct gccgacatgg aagccatcac aaacggcatg | 900 |
| atgaacctga atcgccagcg gcatcagcac cttgtcgcct tgcgtataat atttgcccat | 960 |
| ggtgaaaacg ggggcgaaga agttgtccat attggccacg tttaaatcaa aactggtgaa | 1020 |
| actcacccag ggattggctg agacgaaaaa catattctca ataaacccct tagggaaata | 1080 |
| ggccaggttt tcaccgtaac acgccacatc ttgcgaatat atgtgtagaa actgccggaa | 1140 |
| atcgtcgtgg tattcactcc agagcgatga aaacgtttca gtttgctcat ggaaaacggt | 1200 |
| gtaacaaggg tgaacactat cccatatcac cagctcaccg tctttcattg ccatacggaa | 1260 |
| ttccggatga gcattcatca ggcgggcaag aatgtgaata aaggccggat aaaacttgtg | 1320 |
| cttattttc tttacggtct ttaaaaaggc cgtaatatcc agctgaacgg tctggttata | 1380 |
| ggtacattga gcaactgact gaaatgcctc aaaatgttct ttacgatgcc attgggatat | 1440 |
| atcaacggtg gtatatccag tgatttttt ctccatttta gcttccttag ctcctgaaaa | 1500 |
| tctcgacgga tcctaactca aaatccacac attatacgag ccggaagcat aaagtgtaaa | 1560 |
| gcctggggtg cctaatgcgg ccgccaatat gactggatat gttgtgtttt acagtattat | 1620 |
| gtagtctgtt ttttatgcaa aatctaattt aatatattga tatttatatc attttacgtt | 1680 |
| tctcgttcag cttttttgta caaacttgtt gatgggtta acatatcata acttcgtata | 1740 |
| atgtatgcta tacgaagtta taggcctgga tcttcgaggt cgagcggccg cagatttagg | 1800 |
| tgacactata gaatatgcat cactagtaag ctttgctcta gatcaaactc acatccaaac | 1860 |
| ataacatgga tatcttcctt accaatcata ctaattattt tgggttaaat attaatcatt | 1920 |
| attttttaaga tattaattaa gaaattaaaa gatttttta aaaaatgtat aaaattatat | 1980 |
| tattcatgat ttttcataca tttgattttg ataataaata tatttttttt aatttcttaa | 2040 |
| aaaatgttgc aagacactta ttagacatag tcttgttctg tttacaaaag cattcatcat | 2100 |
| ttaatacatt aaaaaatatt taatactaac agtagaatct tcttgtgagt ggtgtgggag | 2160 |
| taggcaacct ggcattgaaa cgagagaaag agagtcagaa ccagaagaca aataaaaagt | 2220 |
| atgcaacaaa caaatcaaaa tcaaagggca aaggctgggg ttggctcaat tggttgctac | 2280 |
| attcaatttt caactcagtc aacggttgag attcactctg acttccccaa tctaagccgc | 2340 |
| ggatgcaaac ggttgaatct aacccacaat ccaatctcgt tacttagggg cttttccgtc | 2400 |
| attaactcac ccctgccacc cggtttccct ataaattgga actcaatgct cccctctaaa | 2460 |
| ctcgtatcgc ttcagagttg agaccaagac acactcgttc atatatctct ctgctcttct | 2520 |
| cttctcttct acctctcaag gtactttct tctccctcta ccaaatccta gattccgtgg | 2580 |
| ttcaatttcg gatcttgcac ttctggtttg ctttgccttg ctttttcctc aactgggtcc | 2640 |
| atctaggatc catgtgaaac tctactcttt ctttaatatc tgcggaatac gcgtttgact | 2700 |
| ttcagatcta gtcgaaatca tttcataatt gcctttcttt cttttagctt atgagaaata | 2760 |
| aaatcacttt ttttttattt caaaataaac cttgggcctt gtgctgactg agatggggtt | 2820 |
| tggtgattac agaattttag cgaattttgt aattgtactt gtttgtctgt agtttgtttt | 2880 |

```
tgttttcttg tttctcatac attccttagg cttcaatttt attcgagtat aggtcacaat    2940
aggaattcaa actttgagca ggggaattaa tcccttcctt caaatccagt ttgtttgtat    3000
atatgtttaa aaaatgaaac ttttgcttta aattctatta taactttttt tatggctgaa    3060
atttttgcat gtgtctttgc tctctgttgt aaatttactg tttaggtact aactctaggc    3120
ttgttgtgca gttttgaag tataaccatg ccacacaaca caatggcggc caccgcttcc    3180
agaaccaccc gattctcttc ttcctcttca cacccccacct tccccaaacg cattactaga    3240
tccaccctcc ctctctctca tcaaaccctc accaaaccca accacgctct caaaatcaaa    3300
tgttccatct ccaaaccccc cacggcggcg cccttcacca aggaagcgcc gaccacggag    3360
cccttcgtgt cacggttcgc ctccggcgaa cctcgcaagg gcgcggacat ccttgtggag    3420
gcgctggaga ggcagggcgt gacgacggtg ttcgcgtacc ccggcggtgc gtcgatggag    3480
atccaccagg cgctcacgcg ctccgccgcc atccgcaacg tgctcccgcg ccacgagcag    3540
ggcggcgtct tcgccgccga aggctacgcg cgttcctccg gcctcccggg cgtctgcatt    3600
gccacctccg gccccggcgc caccaacctc gtgagcggcc tcgccgacgc tttaatggac    3660
agcgtcccag tcgtcgccat caccggccag gtcgcccgcc ggatgatcgg caccgacgcc    3720
ttccaagaaa ccccgatcgt ggaggtgagc agatccatca cgaagcacaa ctacctcatc    3780
ctcgacgtcg acgacatccc ccgcgtcgtc gccgaggctt tcttcgtcgc cacctccggc    3840
cgccccggtc cggtcctcat cgacattccc aaagacgttc agcagcaact cgccgtgcct    3900
aattgggacg agcccgttaa cctccccggt tacctcgcca ggctgcccag gccccccgcc    3960
gaggcccaat tggaacacat tgtcagactc atcatggagg cccaaaagcc cgttctctac    4020
gtcggcggtg gcagtttgaa ttccagtgct gaattgaggc gctttgttga actcactggt    4080
attcccgttg ctagcacttt aatgggtctt ggaacttttc ctattggtga tgaatattcc    4140
cttcagatgc tgggtatgca tggtactgtt tatgctaact atgctgttga caatagtgat    4200
ttgttgcttg cctttggggt aaggtttgat gaccgtgtta ctgggaagct tgaggctttt    4260
gctagtaggg ctaagattgt tcacattgat attgattctg ccgagattgg gaagaacaag    4320
caggcgcacg tgtcggtttg cgcggatttg aagttggcct tgaagggaat taatatgatt    4380
ttggaggaga aaggagtgga gggtaagttt gatcttggag gttggagaga agagattaat    4440
gtgcagaaac acaagtttcc attgggttac aagacattcc aggacgcgat ttctccgcag    4500
catgctatcg aggttcttga tgagttgact aatggagatg ctattgttag tactggggtt    4560
gggcagcatc aaatgtgggc tgcgcagttt tacaagtaca agagaccgag gcagtggttg    4620
acctcagggg gtcttggagc catgggtttt ggattgcctg cggctattgg tgctgctgtt    4680
gctaaccctg gggctgttgt ggttgacatt gatgggatg gtagtttcat catgaatgtt    4740
caggagttgg ccactataag agtggagaat ctcccagtta agatattgtt gttgaacaat    4800
cagcatttgg gtatggtggt tcagttggag gataggttct acaagtccaa tagagctcac    4860
acctatcttg gagatccgtc tagcgagagc gagatattcc caaacatgct caagtttgct    4920
gatgcttgtg ggataccggc agcgcgagtg acgaagaagg aagagcttag agcggcaatt    4980
cagagaatgt tggacacccc tggccectac cttcttgatg tcattgtgcc ccatcaggag    5040
catgtgttgc cgatgattcc cagtaatgga tccttcaagg atgtgataac tgagggtgat    5100
ggtagaacga ggtactgatt gcctagacca aatgttcctt gatgcttgtt ttgtacaata    5160
tatataagat aatgctgtcc tagttgcagg atttggcctg tggtgagcat catagtctgt    5220
```

```
agtagttttg gtagcaagac attttatttt ccttttattt aacttactac atgcagtagc    5280
atctatctat ctctgtagtc tgatatctcc tgttgtctgt attgtgccgt tggatttttt    5340
gctgtagtga gactgaaaat gatgtgctag taataatatt tctgttagaa atctaagtag    5400
agaatctgtt gaagaagtca aaagctaatg gaatcaggtt acatattcaa tgttttttctt   5460 ttttttagcgg ttggtagacg tgtagattca acttctcttg gagctcacct aggcaatcag   5520
taaaatgcat attcctttt taacttgcca tttatttact tttagtggaa attgtgacca     5580
atttgttcat gtagaacgga tttggaccat tgcgtccaca aaacgtctct tttgctcgat    5640
cttcacaaag cgataccgaa atccagagat agttttcaaa agtcagaaat ggcaaagtta    5700
taaatagtaa aacagaatag atgctgtaat cgacttcaat aacaagtggc atcacgtttc    5760
tagttctaga cccatcagat cgaattaaca tatcataact tcgtataatg tatgctatac    5820
gaagttatag gcctggatcc actagttcta gagcggccgc tcgagggggg gcccggtacc    5880
ggcgcgccgt tctatagtgt cacctaaatc gtatgtgtat gatacataag gttatgtatt    5940
aattgtagcc gcgttctaac gacaatatgt ccatatggtg cactctcagt acaatctgct    6000
ctgatgccgc atagttaagc cagccccgac acccgccaac acccgctgac gcgccctgac    6060
gggcttgtct gctcccggca tccgcttaca gacaagctgt gaccgtctcc gggagctgca    6120
tgtgtcagag gttttcaccg tcatcaccga aacgcgcgag acgaaagggc ctcgtgatac    6180
gcctattttt ataggttaat gtcatgacca aaatccctta acgtgagttt tcgttccact    6240
gagcgtcaga ccccgtagaa aagatcaaag gatcttcttg agatcctttt tttctgcgcg    6300
taatctgctg cttgcaaaca aaaaaaccac cgctaccagc ggtggtttgt ttgccggatc    6360
aagagctacc aactcttttt ccgaaggtaa ctggcttcag cagagcgcag ataccaaata    6420
ctgtccttct agtgtagccg tagttaggcc accacttcaa gaactctgta gcaccgccta    6480
catacctcgc tctgctaatc ctgttaccag tggctgctgc cagtggcgat aagtcgtgtc    6540
ttaccgggtt ggactcaaga cgatagttac cggataaggc gcagcggtcg ggctgaacgg    6600
ggggttcgtg cacacagccc agcttggagc gaacgaccta caccgaactg agatacctac    6660
agcgtgagca ttgagaaagc gccacgcttc ccgaagggag aaaggcggac aggtatccgg    6720
taagcggcag ggtcggaaca ggagagcgca cgagggagct tccaggggga aacgcctggt    6780
atctttatag tcctgtcggg tttcgccacc tctgacttga gcgtcgattt ttgtgatgct    6840
cgtcaggggg gcggagccta tggaaaaacg ccagcaacgc ggcctttta cggttcctgg    6900 cctttttgctg gccttttgct cacatgttct ttcctgcgtt atcccctgat tctgtggata   6960
accgtattac cgcctttgag tgagctgata ccgctcgccg cagccgaacg accgagcgca    7020
gcgagtcagt gagcgaggaa gcggaagagc gcccaatacg caaaccgcct ctccccgcgc    7080
gttggccgat tcattaatgc aggttgatca gatctcgatc ccgcgaaatt aatacgactc    7140
actataggga gaccacaacg gtttccctct agaaataatt ttgttaact ttaagaagga    7200 gatatacccca tggaaaagcc tgaactcacc gcgacgtctg tcgagaagtt tctgatcgaa    7260
aagttcgaca gcgtctccga cctgatgcag ctctcggagg gcgaagaatc tcgtgctttc    7320
agcttcgatg taggagggcg tggatatgtc ctgcgggtaa atagctgcgc cgatggtttc    7380
tacaaagatc gttatgttta tcggcacttt gcatcggccg cgctcccgat tccggaagtg    7440
cttgacattg gggaattcag cgagagcctg acctattgca tctcccgccg tgcacagggt    7500
gtcacgttgc aagacctgcc tgaaaccgaa ctgcccgctg ttctgcagcc ggtcgcggag    7560
gctatggatg cgatcgctgc ggccgatctt agccagacga gcgggttcgg cccattcgga    7620
```

```
ccgcaaggaa tcggtcaata cactacatgg cgtgatttca tatgcgcgat tgctgatccc    7680
catgtgtatc actggcaaac tgtgatggac gacaccgtca gtgcgtccgt cgcgcaggct    7740
ctcgatgagc tgatgctttg ggccgaggac tgccccgaag tccggcacct cgtgcacgcg    7800
gatttcggct ccaacaatgt cctgacggac aatggccgca taacagcggt cattgactgg    7860
agcgaggcga tgttcgggga ttcccaatac gaggtcgcca acatcttctt ctggaggccg    7920
tggttggctt gtatggagca gcagacgcgc tacttcgagc ggaggcatcc ggagcttgca    7980
ggatcgccgc ggctccgggc gtatatgctc cgcattggtc ttgaccaact ctatcagagc    8040
ttggttgacg gcaatttcga tgatgcagct tgggcgcagg tcgatgcgca cgcaatcgtc    8100
cgatccggag ccgggactgt cgggcgtaca caaatcgccc gcagaagcgc ggccgtctgg    8160
accgatggct gtgtagaagt actcgccgat agtggaaacc gacgcccag cactcgtccg    8220 agggcaaagg aatagtgagg tacagcttgg atcgatccgg ctgctaacaa agcccgaaag    8280
gaagctgagt tggctgctgc caccgctgag caataactag cataacccct tggggcctct    8340
aaacgggtct tgaggggttt tttgctgaaa ggaggaacta tatccggatg atcgggcgcg    8400
ccggtaccc                                                            8409

<210> SEQ ID NO 35
<211> LENGTH: 10017
<212> TYPE: DNA
<213> ORGANISM: artificial
<220> FEATURE:
<223> OTHER INFORMATION: DNA construct QC339

<400> SEQUENCE: 35
tttgtacaaa cttgttgatg gggttaacat atcataactt cgtataatgt atgctatacg      60
aagttatagg cctggatctt cgaggtcgag cggccgcaga tttaggtgac actatagaat     120
atgcatcact agtaagcttt gctctagatc aaactcacat ccaaacataa catggatatc     180
ttccttacca atcatactaa ttattttggg ttaaatatta atcattattt ttaagatatt     240
aattaagaaa ttaaaagatt ttttaaaaaa atgtataaaa ttatattatt catgattttt     300
catacatttg attttgataa taaatatatt ttttttaatt tcttaaaaaa tgttgcaaga     360
cacttattag acatagtctt gttctgttta caaaagcatt catcatttaa tacattaaaa     420
aatatttaat actaacagta gaatcttctt gtgagtggtg tgggagtagg caacctggca     480
ttgaaacgag agaaagagag tcagaaccag aagacaaata aaagtatgc aacaaacaaa     540 tcaaaatcaa agggcaaagg ctggggttgg ctcaattggt tgctacattc aattttcaac     600
tcagtcaacg gttgagattc actctgactt ccccaatcta agccgcggat gcaaacggtt     660
gaatctaacc cacaatccaa tctcgttact taggggcttt tccgtcatta actcaccct     720 gccacccggt ttccctataa attggaactc aatgctcccc tctaaactcg tatcgcttca     780
gagttgagac caagacacac tcgttcatat atctctctgc tcttctcttc tcttctacct     840
ctcaaggtac tttcttctc cctctaccaa atcctagatt ccgtggttca atttcggatc     900
ttgcacttct ggttttgctt tgccttgcttt ttcctcaact gggtccatct aggatccatg     960
tgaaactcta ctctttcttt aatatctgcg gaatacgcgt tgactttca gatctagtcg    1020 aaatcatttc ataattgcct ttcttcttt tagcttatga gaaataaaat cacttttttt    1080
ttatttcaaa ataaaccttg ggccttgtgc tgactgagat ggggtttggt gattacagaa    1140
ttttagcgaa ttttgtaatt gtacttgttt gtctgtagtt ttgttttgtt ttcttgtttc    1200
```

```
tcatacattc cttaggcttc aattttattc gagtataggt cacaatagga attcaaactt    1260
tgagcagggg aattaatccc ttccttcaaa tccagtttgt ttgtatatat gtttaaaaaa    1320
tgaaactttt gctttaaatt ctattataac ttttttatg gctgaaattt ttgcatgtgt     1380
ctttgctctc tgttgtaaat ttactgttta ggtactaact ctaggcttgt tgtgcagttt    1440
ttgaagtata accatgccac acaacacaat ggcggccacc gcttccagaa ccacccgatt    1500
ctcttcttcc tcttcacacc ccaccttccc caaacgcatt actagatcca ccctccctct    1560
ctctcatcaa accctcacca aacccaacca cgctctcaaa atcaaatgtt ccatctccaa    1620
accccccacg gcggcgccct tcaccaagga agcgccgacc acggagccct tcgtgtcacg    1680
gttcgcctcc ggcgaacctc gcaagggcgc ggacatcctt gtggaggcgc tggagaggca    1740
gggcgtgacg acggtgttcg cgtaccccgg cggtgcgtcg atggagatcc accaggcgct    1800
cacgcgctcc gccgccatcc gcaacgtgct cccgcgccac gagcagggcg gcgtcttcgc    1860
cgccgaaggc tacgcgcgtt cctccggcct ccccggcgtc tgcattgcca cctccggccc    1920
cggcgccacc aacctcgtga gcggcctcgc cgacgcttta atggacagcg tcccagtcgt    1980
cgccatcacc ggccaggtcg cccgccggat gatcggcacc gacgccttcc aagaaacccc    2040
gatcgtggag gtgagcagat ccatcacgaa gcacaactac ctcatcctcg acgtcgacga    2100 catccccgc gtcgtcgccg aggctttctt cgtcgccacc tccggccgcc ccggtccggt     2160
cctcatcgac attcccaaag acgttcagca gcaactcgcc gtgcctaatt gggacgagcc    2220
cgttaacctc cccggttacc tcgccaggct gcccaggccc ccgccgagg cccaattgga      2280 acacattgtc agactcatca tggaggccca aaagcccgtt ctctacgtcg gcggtggcag    2340
tttgaattcc agtgctgaat tgaggcgctt tgttgaactc actggtattc ccgttgctag    2400
cactttaatg ggtcttggaa cttttcctat tggtgatgaa tattcccttc agatgctggg    2460
tatgcatggt actgtttatg ctaactatgc tgttgacaat agtgatttgt tgcttgcctt    2520 tgggtaagt tttgatgacc gtgttactgg gaagcttgag gcttttgcta gtagggctaa     2580
gattgttcac attgatattg attctgccga gattgggaag aacaagcagg cgcacgtgtc    2640
ggtttgcgcg gatttgaagt tggccttgaa gggaattaat atgattttgg aggagaaagg    2700
agtggagggt aagtttgatc ttggaggttg gagagaagag attaatgtgc agaaacacaa    2760
gtttccattg ggttacaaga cattccagga cgcgatttct ccgcagcatg ctatcgaggt    2820
tcttgatgag ttgactaatg gagatgctat tgttagtact ggggttgggc agcatcaaat    2880
gtgggctgcg cagttttaca agtacaagag accgaggcag tggttgacct caggggtct    2940 tggagccatg ggttttggat tgcctgcggc tattggtgct gctgttgcta accctggggc    3000
tgttgtggtt gacattgatg gggatggtag tttcatcatg aatgttcagg agttggccac    3060
tataagagtg gagaatctcc cagttaagat attgttgttg aacaatcagc atttgggtat    3120
ggtggttcag ttggaggata ggttctacaa gtccaataga gctcacacct atcttggaga    3180
tccgtctagc gagagcgaga tattcccaaa catgctcaag tttgctgatg cttgtgggat    3240
accggcagcg cgagtgacga agaaggaaga gcttagagcg gcaattcaga gaatgttgga    3300 caccctggc ccctaccttc ttgatgtcat tgtgccccat caggagcatg tgttgccgat    3360 gattccagt aatggatcct tcaaggatgt gataactgag ggtgatggta gaacgaggta    3420
ctgattgcct agaccaaatg ttccttgatg cttgttttgt acaatatata taagataatg    3480
ctgtcctagt tgcaggattt ggcctgtggt gagcatcata gtctgtagta gttttggtag    3540
caagacattt tattttcctt ttatttaact tactacatgc agtagcatct atctatctct    3600
```

```
gtagtctgat atctcctgtt gtctgtattg tgccgttgga ttttttgctg tagtgagact    3660
gaaaatgatg tgctagtaat aatatttctg ttagaaatct aagtgagaaa tctgttgaag    3720
aagtcaaaag ctaatggaat caggttacat attcaatgtt tttcttttt tagcggttgg    3780
tagacgtgta gattcaactt ctcttggagc tcacctaggc aatcagtaaa atgcatattc    3840
ctttttaac ttgccattta tttacttta gtggaaattg tgaccaattt gttcatgtag    3900
aacggatttg gaccattgcg tccacaaaac gtctcttttg ctcgatcttc acaaagcgat    3960
accgaaatcc agagatagtt ttcaaaagtc agaaatggca aagttataaa tagtaaaaca    4020
gaatagatgc tgtaatcgac ttcaataaca agtggcatca cgtttctagt tctagaccca    4080
tcagatcgaa ttaacatatc ataacttcgt ataatgtatg ctatacgaag ttataggcct    4140
ggatccacta gttctagagc ggccgctcga ggggggggccc ggtaccggcg cgccgttcta    4200
tagtgtcacc taaatcgtat gtgtatgata cataaggtta tgtattaatt gtagccgcgt    4260
tctaacgaca atatgtccat atggtgcact ctcagtacaa tctgctctga tgccgcatag    4320
ttaagccagc cccgacaccc gccaacaccc gctgacgcgc cctgacgggc ttgtctgctc    4380
ccggcatccg cttacagaca agctgtgacc gtctccggga gctgcatgtg tcagaggttt    4440
tcaccgtcat caccgaaacg cgcgagacga aagggcctcg tgatacgcct atttttatag    4500
gttaatgtca tgaccaaaat cccttaacgt gagttttcgt tccactgagc gtcagacccc    4560
gtagaaaaga tcaaaggatc ttcttgagat cctttttttc tgcgcgtaat ctgctgcttg    4620
caaacaaaaa aaccaccgct accagcggtg gtttgtttgc cggatcaaga gctaccaact    4680
ctttttccga aggtaactgg cttcagcaga gcgcagatac caaatactgt ccttctagtg    4740
tagccgtagt taggccacca cttcaagaac tctgtagcac cgcctacata cctcgctctg    4800
ctaatcctgt taccagtggc tgctgccagt ggcgataagt cgtgtcttac cgggttggac    4860
tcaagacgat agttaccgga taaggcgcag cggtcgggct gaacggggg ttcgtgcaca    4920
cagcccagct tggagcgaac gacctacacc gaactgagat acctacagcg tgagcattga    4980
gaaagcgcca cgcttcccga agggagaaag gcggacaggt atccggtaag cggcagggtc    5040
ggaacaggag agcgcacgag ggagcttcca gggggaaacg cctggtatct ttatagtcct    5100
gtcgggtttc gccacctctg acttgagcgt cgatttttgt gatgctcgtc agggggggcgg    5160
agcctatgga aaaacgccag caacgcggcc ttttacggtt cctggccttt tgctggcct    5220
tttgctcaca tgttctttcc tgcgttatcc cctgattctg tggataaccg tattaccgcc    5280
tttgagtgag ctgataccgc tcgccgcagc cgaacgaccg agcgcagcga gtcagtgagc    5340
gaggaagcgg aagagcgccc aatacgcaaa ccgcctctcc ccgcgcgttg gccgattcat    5400
taatgcaggt tgatcagatc tcgatcccgc gaaattaata cgactcacta gggagacc    5460
acaacggttt ccctctagaa ataattttgt ttaactttaa gaaggagata tacccatgga    5520
aaagcctgaa ctcaccgcga cgtctgtcga agtttctg atcgaaaagt cgacagcgt    5580
ctccgacctg atgcagctct cggagggcga agaatctcgt gctttcagct tcgatgtagg    5640
agggcgtgga tatgtcctgc gggtaaatag ctgcgccgat ggtttctaca aagatcgtta    5700
tgtttatcgg cactttgcat cggccgcgct cccgattccg gaagtgcttg acattgggga    5760
attcagcgag agcctgacct attgcatctc ccgccgtgca cagggtgtca cgttgcaaga    5820
cctgcctgaa accgaactgc ccgctgttct gcagccggtc gcggaggcta tggatgcgat    5880
cgctgcggcc gatcttagcc agacgagcgg gttcggccca ttcggaccgc aaggaatcgg    5940
```

-continued

| | |
|---|---|
| tcaatacact acatggcgtg atttcatatg cgcgattgct gatccccatg tgtatcactg | 6000 |
| gcaaactgtg atggacgaca ccgtcagtgc gtccgtcgcg caggctctcg atgagctgat | 6060 |
| gctttgggcc gaggactgcc ccgaagtccg gcacctcgtg cacgcggatt tcggctccaa | 6120 |
| caatgtcctg acgacaatg gccgcataac agcggtcatt gactggagcg aggcgatgtt | 6180 |
| cggggattcc caatacgagg tcgccaacat cttcttctgg aggccgtggt tggcttgtat | 6240 |
| ggagcagcag acgcgctact tcgagcggag gcatccggag cttgcaggat cgccgcggct | 6300 |
| ccgggcgtat atgctccgca ttggtcttga ccaactctat cagagcttgg ttgacggcaa | 6360 |
| tttcgatgat gcagcttggg cgcagggtcg atgcgacgca atcgtccgat ccggagccgg | 6420 |
| gactgtcggg cgtacacaaa tcgcccgcag aagcgcggcc gtctggaccg atggctgtgt | 6480 |
| agaagtactc gccgatagtg gaaaccgacg ccccagcact cgtccgaggg caaaggaata | 6540 |
| gtgaggtaca gcttggatcg atccggctgc taacaaagcc cgaaaggaag ctgagttggc | 6600 |
| tgctgccacc gctgagcaat aactagcata accccttggg gcctctaaac gggtcttgag | 6660 |
| gggtttttg ctgaaaggag gaactatatc cggatgatcg ggcgcgccgg tacccatcaa | 6720 |
| ccactttgta caagaaagct gggtctagat atctcgaccc gggtgattgc ggttacatca | 6780 |
| tgtacggaaa ataattcta atccttgatt taaatttgaa cttgactatt tatttattct | 6840 |
| ttatttcatt ttgtaaatca ttttatgtat ctcctggcaa gcaattttat ccaccttgca | 6900 |
| ccaacacctt cgggttccat aatcaaacca ccttaacttc acaccatgct gtaactcaca | 6960 |
| ccgcccagca tctccaatgt gaaagaagct aaaatttaat aaacaatcat acgaagcagt | 7020 |
| gacaaaatac cagatggtat taatgcttcg ataaaattaa ttggaaagta taaaatggta | 7080 |
| gaaaataata aattataatt aatttaagta agataaaaaa taattaaaaa ctaaaatgtt | 7140 |
| aaaattttaa aaaaattatt ttaataata tttaaaaaca ttaaaaatca ttttaaaaaa | 7200 |
| tttatttata gaacaattaa ataaatattt cagctaataa aaaacaaaag cttacctagc | 7260 |
| cttagaagac aacttgtcca acaattagat gatacccatt gcccttacgt tttctttaac | 7320 |
| atcaattatt gttttgtca acaagctatc ttttagtttt attttattgg taaaaaatat | 7380 |
| gtcgccttca gttgcatca tttaacacat ctcgtcatta gaaaataaa actcttccct | 7440 |
| aaacgattag tagaaaaaat cattcgataa taaataagaa agaaaaatta gaaaaaaata | 7500 |
| acttcatttt aaaaaaatca ttaaggctat atttttaaa tgactaattt tatatagact | 7560 |
| gtaactaaaa gtatacaatt tattatgcta tgtatcttaa agaattactt ataaaaatct | 7620 |
| acggaagaat atcttacaaa gtgaaaaaca aatgagaaag aatttagtgg gatgattatg | 7680 |
| attttatttg aaaattgaaa aataattat taaagacttt agtggagtaa gaaagctttc | 7740 |
| ctattagtct tttcttatcc ataaaaaaaa aaaaaaaaat ctagcgtgac agcttttcca | 7800 |
| tagattttaa taatgtaaaa tactggtagc agccgaccgt tcaggtaatg gacactgtgg | 7860 |
| tcctaacttg caacgggtgc gggcccaatt taataacgcc gtggtaacgg ataaagccaa | 7920 |
| gcgtgaagcg gtgaaggtac atctctgact ccgtcaagat tacgaaaccg tcaactacga | 7980 |
| aggactcccc gaaatatcat ctgtgtcata acaccaagt cacaccatac atgggcacgc | 8040 |
| gtcacaatat gattggagaa cggttccacc gcatatgcta taaatgccc ccacacccct | 8100 |
| cgaccctaat cgcacttcaa ttgcaatcaa attagttcat tctctttgcg cagttcccta | 8160 |
| cctctccttt caaggttcgt agatttcttc cgtttttttt tcttcttctt tattgtttgt | 8220 |
| tctacatcag catgatgttg atttgattgt gttttctatc gtttcatcga ttataaattt | 8280 |
| tcataatcag aagattcagc ttttattaat gcaagaacgt ccttaattga tgattttata | 8340 |

```
accgtaaatt aggtctaatt agagtttttt tcataaagat tttcagatcc gtttacaaca    8400
agccttaatt gttgattctg tagtcgtaga ttaaggtttt tttcatgaac tacttcagat    8460
ccgttaaaca acagccttat tgttgatac ttcagtcgtt tttcaagaaa ttgttcagat     8520
ccgttgataa aagccttatt cgttgattct gtatggtatt tcaagagata ttgctcaggt    8580
cctttagcaa ctaccttatt tgttgattct gtggccatag attaggattt tttttcacga    8640
aattgcttct tgaaattacg tgatggattt tgattctgat ttatcttgtg attgttgact    8700
ctacagccat ggcccacagc aagcacggcc tgaaggagga gatgaccatg aagtaccaca    8760
tggagggctg cgtgaacggc cacaagttcg tgatcaccgg cgagggcatc ggctacccct    8820
tcaagggcaa gcagaccatc aacctgtgcg tgatcgaggg cggcccctg cccttcagcg      8880
aggacatcct gagcgccggc ttcaagtacg gcgaccggat cttcaccgag tacccccagg    8940
acatcgtgga ctacttcaag aacagctgcc ccgccggcta cacctggggc cggagcttcc    9000
tgttcgagga cggcgccgtg tgcatctgta acgtggacat caccgtgagc gtgaaggaga    9060
actgcatcta ccacaagagc atcttcaacg gcgtgaactt ccccgccgac ggccccgtga    9120
tgaagaagat gaccaccaac tgggaggcca gctgcgagaa gatcatgccc gtgcctaagc    9180
agggcatcct gaagggcgac gtgagcatgt acctgctgct gaaggacggc ggccggtacc    9240
ggtgccagtt cgacaccgtg tacaaggcca gagcgtgcc cagcaagatg cccgagtggc     9300
acttcatcca gcacaagctg ctgcgggagg accggagcga cgccaagaac cagaagtggc    9360
agctgaccga gcacgccatc gccttcccca gcgcccctggc ctgagagctc tgaacgggaa   9420
ttaaacctat aaacataaat ataaataata tatataaacc taagtgtcta agttccataa    9480
attaagctgt agtctctggc ttaaaacatg ttaggtttgt ttatacaagt agttggatgt    9540
ttggagtact tcggtctttt gcgtaccatc aatatttaag aactaagtta gttatgttcc    9600
gtaacttatg ggctcttaat taaactatat ctgcacaaaa ttatatatat atcaaatgtg    9660
atggtatgtg gactataaaa agatatggtt gagaaccaca aactttgaaa cttcgaataa    9720
tatattgcca gtgacagtct tgttgatttg ttatagcaag tcctatttc ttaatcattg     9780
ctttgtttta acgtacctag atttcataac ttttgtcttt gtctcaagct gaacctaatg    9840
atgatagtaa tattaactta ttgtataggg gtatttcata ggataaaaaa tgatgtgcaa    9900
ttacgtgtag accaaatatt acttgatgac agatggaatt ctagtggccg gcccagctga    9960
tatccatcac actggcggcc gcactcgact gaattggttc cggcgccagc ctgctttt     10017
```

<210> SEQ ID NO 36
<211> LENGTH: 10031
<212> TYPE: DNA
<213> ORGANISM: artificial
<220> FEATURE:
<223> OTHER INFORMATION: DNA construct QC340

<400> SEQUENCE: 36

```
tttgtacaaa cttgttgatg gggttaacat atcataactt cgtataatgt atgctatacg     60
aagttatagg cctggatctt cgaggtcgag cggccgcaga tttaggtgac actatagaat    120
atgcatcact agtaagcttt gctctagatc aaactcacat ccaaacataa catggatatc    180
ttccttacca atcatactaa ttattttggg ttaaatatta atcattattt ttaagatatt    240
aattaagaaa ttaaagatt ttttaaaaaa atgtataaaa ttatattatt catgattttt      300
catacatttg attttgataa taatatatt ttttttaatt tcttaaaaaa tgttgcaaga     360
```

```
cacttattag acatagtctt gttctgttta caaaagcatt catcatttaa tacattaaaa    420
aatatttaat actaacagta gaatcttctt gtgagtggtg tgggagtagg caacctggca    480
ttgaaacgag agaaagagag tcagaaccag aagacaaata aaaagtatgc aacaaacaaa    540
tcaaaatcaa agggcaaagg ctggggttgg ctcaattggt tgctacattc aattttcaac    600
tcagtcaacg gttgagattc actctgactt ccccaatcta agccgcggat gcaaacggtt    660
gaatctaacc cacaatccaa tctcgttact tagggctttt ccgtcatta actcacccct     720 gccacccggt ttccctataa attggaactc aatgctcccc tctaaactcg tatcgcttca    780
gagttgagac caagacacac tcgttcatat atctctctgc tcttctcttc tcttctacct    840
ctcaaggtac ttttcttctc cctctaccaa atcctagatt ccgtggttca atttcggatc    900
ttgcacttct ggtttgcttt gccttgcttt ttcctcaact gggtccatct aggatccatg    960
tgaaactcta ctctttcttt aatatctgcg gaatacgcgt ttgactttca gatctagtcg   1020
aaatcatttc ataattgcct ttctttcttt tagcttatga gaaataaaat cactttttt    1080 ttatttcaaa ataaaccttg ggccttgtgc tgactgagat ggggtttggt gattacagaa   1140
ttttagcgaa ttttgtaatt gtacttgttt gtctgtagtt ttgttttgtt ttcttgtttc    1200
tcatacattc cttaggcttc aattttattc gagtataggt cacaatagga attcaaactt   1260
tgagcagggg aattaatccc ttccttcaaa tccagtttgt ttgtatatat gtttaaaaaa   1320
tgaaactttt gctttaaatt ctattataac ttttttttatg gctgaaattt ttgcatgtgt   1380
ctttgctctc tgttgtaaat ttactgttta ggtactaact ctaggcttgt tgtgcagttt    1440
ttgaagtata accatgccac acaacacaat ggcggccacc gcttccagaa ccacccgatt    1500
ctcttcttcc tcttcacacc ccaccttccc caaacgcatt actagatcca ccctccctct   1560
ctctcatcaa accctcacca aacccaacca cgctctcaaa atcaaatgtt ccatctccaa    1620
accccccacg gcggcgccct tcaccaagga agcgccgacc acggagccct tcgtgtcacg   1680
gttcgcctcc ggcgaacctc gcaagggcgc ggacatcctt gtggaggcgc tggagaggca   1740
gggcgtgacg acggtgttcg cgtaccccgg cggtgcgtcg atggagatcc accaggcgct   1800
cacgcgctcc gccgccatcc gcaacgtgct cccgcgccac gagcagggcg gcgtcttcgc   1860
cgccgaaggc tacgcgcgtt cctccggcct ccccggcgtc tgcattgcca cctccggccc   1920
cggcgccacc aacctcgtga gcggcctcgc cgacgcttta atggacagcg tcccagtcgt   1980
cgccatcacc ggccaggtcg cccgccggat gatcggcacc gacgccttcc aagaaacccc   2040
gatcgtggag gtgagcagat ccatcacgaa gcacaactac ctcatcctcg acgtcgacga   2100
catcccccgc gtcgtcgccg aggctttctt cgtcgccacc tccggccgcc ccggtccggt   2160
cctcatcgac attcccaaag acgttcagca gcaactcgcc gtgcctaatt gggacgagcc   2220
cgttaacctc cccggttacc tcgccaggct gcccaggccc cccgccgagg cccaattgga   2280
acacattgtc agactcatca tggaggccca aaagcccgtt ctctacgtcg gcggtggcag   2340
tttgaattcc agtgctgaat tgaggcgctt tgttgaactc actggtattc ccgttgctag   2400
cactttaatg ggtcttggaa cttttcctat tggtgatgaa tattcccttc agatgctggg   2460
tatgcatggt actgtttatg ctaactatgc tgttgacaat agtgatttgt tgcttgcctt   2520
tggggtaagg tttgatgacc gtgttactgg gaagcttgag gcttttgcta gtagggctaa   2580
gattgttcac attgatattg attctgccga gattgggaag aacaagcagg cgcacgtgtc   2640
ggtttgcgcg gatttgaagt tggccttgaa gggaattaat atgattttgg aggagaaagg   2700
agtggagggt aagtttgatc ttggaggttg gagagaagag attaatgtgc agaaacacaa   2760
```

| | |
|---|---|
| gtttccattg ggttacaaga cattccagga cgcgatttct ccgcagcatg ctatcgaggt | 2820 |
| tcttgatgag ttgactaatg gagatgctat tgttagtact ggggttgggc agcatcaaat | 2880 |
| gtgggctgcg cagttttaca agtacaagag accgaggcag tggttgacct caggggtct | 2940 |
| tggagccatg ggttttggat tgcctgcggc tattggtgct gctgttgcta accctggggc | 3000 |
| tgttgtggtt gacattgatg gggatggtag tttcatcatg aatgttcagg agttggccac | 3060 |
| tataagagtg gagaatctcc cagttaagat attgttgttg aacaatcagc atttgggtat | 3120 |
| ggtggttcag ttggaggata ggttctacaa gtccaataga gctcacacct atcttggaga | 3180 |
| tccgtctagc gagagcgaga tattcccaaa catgctcaag tttgctgatg cttgtgggat | 3240 |
| accggcagcg cgagtgacga agaaggaaga gcttagagcg gcaattcaga gaatgttgga | 3300 |
| cacccctggc ccctaccttc ttgatgtcat tgtgccccat caggagcatg tgttgccgat | 3360 |
| gattcccagt aatggatcct tcaaggatgt gataactgag ggtgatggta gaacgaggta | 3420 |
| ctgattgcct agaccaaatg ttccttgatg cttgttttgt acaatatata taagataatg | 3480 |
| ctgtcctagt tgcaggattt ggcctgtggt gagcatcata gtctgtagta gttttggtag | 3540 |
| caagacattt tatttccctt ttattaact tactacatgc agtagcatct atctatctct | 3600 |
| gtagtctgat atctcctgtt gtctgtattg tgccgttgga ttttttgctg tagtgagact | 3660 |
| gaaaatgatg tgctagtaat aatatttctg ttagaaatct aagtagagaa tctgttgaag | 3720 |
| aagtcaaaag ctaatggaat caggttacat attcaatgtt tttctttttt tagcggttgg | 3780 |
| tagacgtgta gattcaactt ctcttggagc tcacctaggc aatcagtaaa atgcatattc | 3840 |
| cttttttaac ttgccattta tttacttta gtggaaattg tgaccaattt gttcatgtag | 3900 |
| aacggatttg gaccattgcg tccacaaaac gtctcttttg ctcgatcttc acaaagcgat | 3960 |
| accgaaatcc agagatagtt ttcaaaagtc agaaatggca aagttataaa tagtaaaaca | 4020 |
| gaatagatgc tgtaatcgac ttcaataaca agtggcatca cgtttctagt tctagaccca | 4080 |
| tcagatcgaa ttaacatatc ataacttcgt ataatgtatg ctatacgaag ttataggcct | 4140 |
| ggatccacta gttctagagc ggccgctcga gggggggccc ggtaccggcg cgccgttcta | 4200 |
| tagtgtcacc taaatcgtat gtgtatgata cataaggtta tgtattaatt gtagccgcgt | 4260 |
| tctaacgaca atatgtccat atggtgcact ctcagtacaa tctgctctga tgccgcatag | 4320 |
| ttaagccagc cccgacaccc gccaacaccc gctgacgcgc cctgacgggc ttgtctgctc | 4380 |
| ccggcatccg cttacagaca agctgtgacc gtctccggga gctgcatgtg tcagaggttt | 4440 |
| tcaccgtcat caccgaaacg cgcgagacga aagggcctcg tgatacgcct atttttatag | 4500 |
| gttaatgtca tgaccaaaat cccttaacgt gagttttcgt tccactgagc gtcagacccc | 4560 |
| gtagaaaaga tcaaaggatc ttcttgagat cctttttttc tgcgcgtaat ctgctgcttg | 4620 |
| caaacaaaaa aaccaccgct accagcggtg gtttgtttgc cggatcaaga gctaccaact | 4680 |
| cttttccga aggtaactgg cttcagcaga gcgcagatac caaatactgt ccttctagtg | 4740 |
| tagccgtagt taggccacca cttcaagaac tctgtagcac cgcctacata cctcgctctg | 4800 |
| ctaatcctgt taccagtggc tgctgccagt ggcgataagt cgtgtcttac cgggttggac | 4860 |
| tcaagacgat agttaccgga taaggcgcag cggtcgggct gaacggggggg ttcgtgcaca | 4920 |
| cagcccagct tggagcgaac gacctacacc gaactgagat acctacagcg tgagcattga | 4980 |
| gaaagcgcca cgcttcccga agggagaaag gcggacaggt atccggtaag cggcagggtc | 5040 |
| ggaacaggag agcgcacgag ggagcttcca gggggaaacg cctggtatct ttatagtcct | 5100 |

```
gtcgggtttc gccacctctg acttgagcgt cgatttttgt gatgctcgtc agggggggcgg    5160 agcctatgga aaaacgccag caacgcggcc tttttacggt tcctggcctt ttgctggcct    5220
tttgctcaca tgttctttcc tgcgttatcc cctgattctg tggataaccg tattaccgcc    5280
tttgagtgag ctgataccgc tcgccgcagc cgaacgaccg agcgcagcga gtcagtgagc    5340
gaggaagcgg aagagcgccc aatacgcaaa ccgcctctcc ccgcgcgttg gccgattcat    5400
taatgcaggt tgatcagatc tcgatcccgc gaaattaata cgactcacta gggagacc      5460 acaacggttt ccctctagaa ataattttgt ttaactttaa gaaggagata tacccatgga    5520
aaagcctgaa ctcaccgcga cgtctgtcga agtttctg atcgaaaagt tcgacagcgt      5580
ctccgacctg atgcagctct cggagggcga agaatctcgt gctttcagct tcgatgtagg    5640
agggcgtgga tatgtcctgc gggtaaatag ctgcgccgat ggtttctaca agatcgtta    5700 tgtttatcgg cactttgcat cggccgcgct cccgattccg gaagtgcttg acattgggga    5760
attcagcgag agcctgacct attgcatctc ccgccgtgca cagggtgtca cgttgcaaga    5820
cctgcctgaa accgaactgc ccgctgttct gcagccggtc gcggaggcta tggatgcgat    5880
cgctgcggcc gatcttagcc agacgagcgg gttcggccca ttcggaccgc aaggaatcgg    5940
tcaatacact acatggcgtg atttcatatg cgcgattgct gatccccatg tgtatcactg    6000
gcaaactgtg atggacgaca ccgtcagtgc gtccgtcgcg caggctctcg atgagctgat    6060
gctttgggcc gaggactgcc ccgaagtccg gcacctcgtg cacgcggatt tcggctccaa    6120
caatgtcctg acggacaatg gccgcataac agcggtcatt gactggagcg aggcgatgtt    6180
cggggattcc caatacgagg tcgccaacat cttcttctgg aggccgtggt tggcttgtat    6240
ggagcagcag acgcgctact tcgagcggag gcatccggag cttgcaggat cgccgcggct    6300
ccgggcgtat atgctccgca ttggtcttga ccaactctat cagagcttgg ttgacggcaa    6360
tttcgatgat gcagcttggg cgcagggtcg atgcgacgca atcgtccgat ccggagccgg    6420
gactgtcggc cgtacacaaa tcgcccgcag aagcgcggcc gtctggaccg atggctgtgt    6480
agaagtactc gccgatagtg gaaaccgacg ccccagcact cgtccgaggg caaaggaata    6540
gtgaggtaca gcttggatcg atccggctgc taacaaagcc cgaaaggaag ctgagttggc    6600
tgctgccacc gctgagcaat aactagcata accccttggg gcctctaaac gggtcttgag    6660
gggttttttg ctgaaaggag gaactatatc cggatgatcg gcgcgccgg tacccatcaa     6720 ccactttgta caagaaagct gggtctagat atctcgaccc gggtgattgc ggttacatca    6780
tgtacggaaa aataattcta atccttgatt taaatttgaa cttgactatt tatttattct    6840
ttatttcatt ttgtaaatca ttttatgtat ctcctggcaa gcaatttat ccaccttgca     6900 ccaacacctt cgggttccat aatcaaacca ccttaacttc acaccatgct gtaactcaca    6960
ccgcccagca tctccaatgt gaaagaagct aaaatttaat aaacaatcat acgaagcagt    7020
gacaaaatac cagatggtat taatgcttcg ataaaattaa ttggaaagta taaaatggta    7080
gaaaataata aattataatt aatttaagta agataaaaaa taattaaaaa ctaaaatgtt    7140 aaaatttaa aaaattatt ttaataata tttaaaaaca ttaaaaatca ttttaaaaaa       7200
tttatttata gaacaattaa ataaatattt cagctaataa aaaacaaaag cttacctagc    7260
cttagaagac aacttgtcca acaattagat gatacccatt gcccttacgt tttctttaac    7320
atcaattatt gttttgtcaa acaagctatc ttttagtttt attttattgg taaaaaatat    7380
gtcgccttca agttgcatca tttaacacat ctcgtcatta gaaaaataaa actcttccct    7440
aaacgattag tagaaaaaat cattcgataa taaataagaa agaaaaatta gaaaaaaata    7500
```

```
acttcatttt aaaaaaatca ttaaggctat attttttaaa tgactaattt tatatagact    7560
gtaactaaaa gtatacaatt tattatgcta tgtatcttaa agaattactt ataaaaatct    7620
acggaagaat atcttacaaa gtgaaaaaca aatgagaaag aatttagtgg gatgattatg    7680
attttatttg aaaattgaaa aataattat taaagacttt agtggagtaa gaaagctttc     7740
ctattagtct tttcttatcc ataaaaaaaa aaaaaaaaat ctagcgtgac agcttttcca    7800
tagattttaa taatgtaaaa tactggtagc agccgaccgt tcaggtaatg gacactgtgg    7860
tcctaacttg caacgggtgc gggcccaatt taataacgcc gtggtaacgg ataaagccaa    7920
gcgtgaagcg gtgaaggtac atctctgact ccgtcaagat tacgaaaccg tcaactacga    7980
aggactcccc gaaatatcat ctgtgtcata acaccaagt cacaccatac atgggcacgc     8040
gtcacaatat gattggagaa cggttccacc gcatatgcta taaatgccc ccacacccct     8100 cgaccctaat cgcacttcaa ttgcaatcaa attagttcat tctctttgcg cagttcccta    8160
cctctccttt caaggttcgt agatttcttc cgttttttt tcttcttctt tattgtttgt     8220
tctacatcag catgatgttg atttgattgt gttttctatc gtttcatcga ttataaattt    8280
tcataatcag aagattcagc ttttattaat gcaagaacgt ccttaattga tgattttata    8340
accgtaaatt aggtctaatt agagttttt tcataaagat tttcagatcc gtttacaaca    8400
agccttaatt gttgattctg tagtcgtaga ttaaggtttt tttcatgaac tacttcagat    8460
ccgttaaaca acagccttat tgttgatac ttcagtcgtt tttcaagaaa ttgttcagat     8520
ccgttgataa aagccttatt cgttgattct gtatggtatt tcaagagata ttgctcaggt    8580
cctttagcaa ctaccttatt tgttgattct gtggccatag attaggattt tttttcacga    8640
aattgcttct tgaaattacg tgatggattt tgattctgat ttatcttgtg attgttgact    8700
ctacagccat ggcccacagc aagcacggcc tgaaggagga gatgaccatg aagtaccaca    8760
tggagggctg cgtgaacggc cacaagttcg tgatcaccgg cgagggcatc ggctacccct    8820
tcaagggcaa gcagaccatc aacctgtgcg tgatcgaggg cggccccctg cccttcagcg    8880
aggacatcct gagcgccggc ttcaagtacg gcgaccggat cttcaccgag tacccccagg    8940
acatcgtgga ctacttcaag aacagctgcc ccgccggcta cacctggggc cggagcttcc    9000
tgttcgagga cggcgccgtg tgcatctgta acgtggacat caccgtgagc gtgaaggaga    9060
actgcatcta ccacaagagc atcttcaacg gcgtgaactt ccccgccgac ggccccgtga    9120
tgaagaagat gaccaccaac tgggaggcca gctgcgagaa gatcatgccc gtgcctaagc    9180
agggcatcct gaagggcgac gtgagcatgt acctgctgct gaaggacggc ggccggtacc    9240
ggtgccagtt cgacaccgtg tacaaggcca agagcgtgcc cagcaagatg cccgagtggc    9300
acttcatcca gcacaagctg ctgcgggagg accggagcga cgccaagaac cagaagtggc    9360
agctgaccga gcacgccatc gccttcccca gcgccctggc ctgagagctc tgaagcagta    9420
ccacactggc ccaaaaaaa aattcatgtg cttaatttct agctgtgaga gacaattaag    9480
tgtatgacca ataaaatggt tttgttgtag gaccaagtct gagagacgcc aagcaccaca    9540
tgaataaaat aaccaaagct tggtttgtat tgtagccttc tctaatgcta ttggtctggt    9600
tacatcatct ttaattcccc tttatatatg catatgttta ttatttattg atttatcctt    9660
gaaagagtac aatttaactt ttaatttttt attttatctt taatttaatc aaaagattta    9720
gttgtcagaa agaaagaacg aagggtgaga taatgatgat agatcatcca tgggccgccg    9780
ttaatagcct ttttcagtct ctaagtcaaa gttaaccccta cagaatccat gtctaagtct    9840
```

```
aacaaccata aggtcaaagc ctccgtcaat tttcagatgc gatttcagtt tattcctcat     9900
tgtaataaac cctatttca gagtaacttg aggatcacga acttcctccg aattctagtg     9960
gccggcccag ctgatatcca tcacactggc ggccgcactc gactgaattg gttccggcgc    10020
cagcctgctt t                                                         10031
```

<210> SEQ ID NO 37
<211> LENGTH: 9995
<212> TYPE: DNA
<213> ORGANISM: artificial
<220> FEATURE:
<223> OTHER INFORMATION: DNA construct QC350

<400> SEQUENCE: 37

```
tttgtacaaa cttgttgatg gggttaacat atcataactt cgtataatgt atgctatacg      60
aagttatagg cctggatctt cgaggtcgag cggccgcaga tttaggtgac actatagaat     120
atgcatcact agtaagcttt gctctagatc aaactcacat ccaaacataa catggatatc     180
ttccttacca atcatactaa ttattttggg ttaaatatta atcattattt ttaagatatt     240
aattaagaaa ttaaaagatt ttttaaaaaa atgtataaaa ttatattatt catgattttt     300
catacatttg attttgataa taaatatatt ttttttaatt tcttaaaaaa tgttgcaaga     360
cacttattag acatagtctt gttctgttta caaaagcatt catcatttaa tacattaaaa     420
aatatttaat actaacagta gaatcttctt gtgagtggtg tgggagtagg caacctggca     480
ttgaaacgag agaaagagag tcagaaccag aagacaaata aaagtatgc aacaaacaaa     540 tcaaaatcaa agggcaaagg ctggggttgg ctcaattggt tgctacattc aattttcaac     600
tcagtcaacg gttgagattc actctgactt ccccaatcta agccgcggat gcaaacggtt     660
gaatctaacc cacaatccaa tctcgttact tagggggcttt ccgtcatta actcacccct     720 gccacccggt ttccctataa attggaactc aatgctcccc tctaaactcg tatcgcttca     780
gagttgagac caagacacac tcgttcatat atctctctgc tcttctcttc tcttctacct     840
ctcaaggtac ttttcttctc cctctaccaa atcctagatt ccgtggttca atttcggatc     900
ttgcacttct ggtttgcttt gccttgcttt tcctcaact gggtccatct aggatccatg     960
tgaaactcta ctctttcttt aatatctgcg gaatacgcgt ttgactttca gatctagtcg    1020
aaatcatttc ataattgcct ttctttcttt tagcttatga gaaataaaat cactttttt    1080 ttatttcaaa ataaaccttg ggccttgtgc tgactgagat ggggtttggt gattacagaa    1140
ttttagcgaa ttttgtaatt gtacttgttt gtctgtagtt ttgttttgtt ttcttgtttc    1200
tcatacattc cttaggcttc aattttattc gagtataggt cacaatagga attcaaactt    1260
tgagcagggg aattaatccc ttccttcaaa tccagtttgt ttgtatatat gtttaaaaaa    1320
tgaaactttt gctttaaatt ctattataac ttttttatg gctgaaattt ttgcatgtgt    1380
ctttgctctc tgttgtaaat ttactgttta ggtactaact ctaggcttgt tgtgcagttt    1440
ttgaagtata accatgccac acaacacaat ggcggccacc gcttccagaa ccacccgatt    1500
ctcttcttcc tcttcacacc ccaccttccc caaacgcatt actagatcca cctccctct    1560 ctctcatcaa accctcacca aacccaacca cgctctcaaa atcaaatgtt ccatctccaa    1620 acccccacg gcggcgccct tcaccaagga agcgccgacc acggagccct tcgtgtcacg    1680
gttcgcctcc ggcgaacctc gcaagggcgc ggacatcctt gtggaggcgc tggagaggca    1740
gggcgtgacg acggtgttcg cgtacccggg cggtgcgtcg atggagatcc accaggcgct    1800
cacgcgctcc gccgccatcc gcaacgtgct cccgcgccac gagcagggcg gcgtcttcgc    1860
```

```
cgccgaaggc tacgcgcgtt cctccggcct ccccggcgtc tgcattgcca cctccggccc    1920
cggcgccacc aacctcgtga gcggcctcgc cgacgcttta atggacagcg tcccagtcgt    1980
cgccatcacc ggccaggtcg cccgccggat gatcggcacc gacgccttcc aagaaacccc    2040
gatcgtggag gtgagcagat ccatcacgaa gcacaactac ctcatcctcg acgtcgacga    2100
catccccgc  gtcgtcgccg aggctttctt cgtcgccacc tccggccgcc ccggtccggt    2160
cctcatcgac attcccaaag acgttcagca gcaactcgcc gtgcctaatt gggacgagcc    2220
cgttaacctc cccggttacc tcgccaggct gcccaggccc ccgccgagg  cccaattgga    2280
acacattgtc agactcatca tggaggccca aagcccgtt  ctctacgtcg gcggtggcag    2340
tttgaattcc agtgctgaat tgaggcgctt tgttgaactc actggtattc ccgttgctag    2400
cactttaatg ggtcttggaa cttttcctat tggtgatgaa tattcccttc agatgctggg    2460
tatgcatggt actgtttatg ctaactatgc tgttgacaat agtgatttgt tgcttgcctt    2520
tggggtaagg tttgatgacc gtgttactgg gaagcttgag gcttttgcta gtagggctaa    2580
gattgttcac attgatattg attctgccga gattgggaag aacaagcagg cgcacgtgtc    2640
ggtttgcgcg gatttgaagt tggccttgaa gggaattaat atgattttgg aggagaaagg    2700
agtggagggt aagtttgatc ttggaggttg gagagaagag attaatgtgc agaaacacaa    2760
gtttccattg ggttacaaga cattccagga cgcgatttct ccgcagcatg ctatcgaggt    2820
tcttgatgag ttgactaatg gagatgctat tgttagtact ggggttgggc agcatcaaat    2880
gtgggctgcg cagttttaca agtacaagag accgaggcag tggttgacct caggggtct     2940
tggagccatg ggttttggat tgcctgcggc tattggtgct gctgttgcta accctggggc    3000
tgttgtggtt gacattgatg gggatggtag tttcatcatg aatgttcagg agttggccac    3060
tataagagtg gagaatctcc cagttaagat attgttgttg aacaatcagc atttgggtat    3120
ggtggttcag ttggaggata ggttctacaa gtccaataga gctcacacct atcttggaga    3180
tccgtctagc gagagcgaga tattcccaaa catgctcaag tttgctgatg cttgtgggat    3240
accggcagcg cgagtgacga agaaggaaga gcttagagcg gcaattcaga gaatgttgga    3300
cacccctggc ccctaccttc ttgatgtcat tgtgccccat caggagcatg tgttgccgat    3360
gattcccagt aatggatcct tcaaggatgt gataactgag ggtgatggta gaacgaggta    3420
ctgattgcct agaccaaatg ttccttgatg cttgttttgt acaatatata taagataatg    3480
ctgtcctagt tgcaggattt ggcctgtggt gagcatcata gtctgtagta gttttggtag    3540
caagacattt tattttccct ttatttaact tactacatgc agtagcatct atctatctct    3600
gtagtctgat atctcctgtt gtctgtattg tgccgttgga ttttttgctg tagtgagact    3660
gaaaatgatg tgctagtaat aatatttctg ttagaaatct aagtagagaa tctgttgaag    3720
aagtcaaaag ctaatggaat caggttacat attcaatgtt tttcttttt  tagcggttgg    3780
tagacgtgta gattcaactt ctcttggagc tcacctaggc aatcagtaaa atgcatattc    3840
cttttttaac ttgccattta tttacttttta gtggaaattg tgaccaattt gttcatgtag    3900
aacggatttg gaccattgcg tccacaaaac gtctcttttg ctcgatcttc acaaagcgat    3960
accgaaatcc agagatagtt ttcaaaagtc agaaatggca aagttataaa tagtaaaaca    4020
gaatagatgc tgtaatcgac ttcaataaca agtggcatca cgtttctagt tctagaccca    4080
tcagatcgaa ttaacatatc ataacttcgt ataatgtatg ctatacgaag ttataggcct    4140
ggatccacta gttctagagc ggccgctcga ggggggggccc ggtaccggcg cgccgttcta    4200
```

```
tagtgtcacc taaatcgtat gtgtatgata cataaggtta tgtattaatt gtagccgcgt    4260
tctaacgaca atatgtccat atggtgcact ctcagtacaa tctgctctga tgccgcatag    4320
ttaagccagc cccgacaccc gccaacaccc gctgacgcgc cctgacgggc ttgtctgctc    4380
ccggcatccg cttacagaca agctgtgacc gtctccggga gctgcatgtg tcagaggttt    4440
tcaccgtcat caccgaaacg cgcgagacga aagggcctcg tgatacgcct attttttatag   4500 gttaatgtca tgaccaaaat cccttaacgt gagttttcgt tccactgagc gtcagacccc    4560
gtagaaaaga tcaaaggatc ttcttgagat cctttttttc tgcgcgtaat ctgctgcttg    4620
caaacaaaaa aaccaccgct accagcggtg gtttgtttgc cggatcaaga gctaccaact    4680 cttttttccga aggtaactgg cttcagcaga gcgcagatac caaatactgt ccttctagtg   4740
tagccgtagt taggccacca cttcaagaac tctgtagcac cgcctacata cctcgctctg    4800
ctaatcctgt taccagtggc tgctgccagt ggcgataagt cgtgtcttac cgggttggac    4860
tcaagacgat agttaccgga taaggcgcag cggtcgggct gaacggggggt tcgtgcaca    4920 cagcccagct tggagcgaac gacctacacc gaactgagat acctacagcg tgagcattga    4980
gaaagcgcca cgcttcccga agggagaaag gcggacaggt atccggtaag cggcagggtc    5040
ggaacaggag agcgcacgag ggagcttcca ggggaaacg cctggtatct ttatagtcct    5100
gtcgggtttc gccacctctg acttgagcgt cgatttttgt gatgctcgtc agggggggcgg   5160 agcctatgga aaaacgccag caacgcggcc ttttacggt tcctggcctt ttgctggcct    5220
tttgctcaca tgttctttcc tgcgttatcc cctgattctg tggataaccg tattaccgcc    5280
tttgagtgag ctgataccgc tcgccgcagc cgaacgaccg agcgcagcga gtcagtgagc    5340
gaggaagcgg aagagcgccc aatacgcaaa ccgcctctcc ccgcgcgttg gccgattcat    5400
taatgcaggt tgatcagatc tcgatcccgc gaaattaata cgactcacta tagggagacc    5460
acaacggttt ccctctagaa ataattttgt ttaactttaa gaaggagata tacccatgga    5520
aaagcctgaa ctcaccgcga cgtctgtcga agtttctg atcgaaaagt tcgacagcgt     5580
ctccgacctg atgcagctct cggagggcga agaatctcgt gctttcagct tcgatgtagg    5640
agggcgtgga tatgtcctgc gggtaaatag ctgcgccgat ggtttctaca agatcgtta    5700 tgtttatcgg cactttgcat cggccgcgct cccgattccg gaagtgcttg acattgggga    5760
attcagcgag agcctgacct attgcatctc ccgccgtgca cagggtgtca cgttgcaaga    5820
cctgcctgaa accgaactgc ccgctgttct gcagccggtc gcggaggcta tggatgcgat    5880
cgctgcggcc gatcttagcc agacgagcgg gttcggccca ttcggaccgc aaggaatcgg    5940
tcaatacact acatggcgtg atttcatatg cgcgattgct gatccccatg tgtatcactg    6000
gcaaactgtg atggacgaca ccgtcagtgc gtccgtcgcg caggctctcg atgagctgat    6060
gctttgggcc gaggactgcc ccgaagtccg gcacctcgtg cacgcggatt tcggctccaa    6120
caatgtcctg acggacaatg gccgcataac agcggtcatt gactggagcg aggcgatgtt    6180
cggggattcc caatacgagg tcgccaacat cttcttctgg aggccgtggt tggcttgtat    6240
ggagcagcag acgcgctact cgagcggag gcatccggag cttgcaggat cgccgcggct    6300
ccgggcgtat atgctccgca ttggtcttga ccaactctat cagagcttgg ttgacggcaa    6360
tttcgatgat gcagcttggg cgcagggtcg atgcgacgca atcgtccgat ccggagccgg    6420
gactgtcggg cgtacacaaa tcgcccgcag aagcgcggcc gtctggaccg atggctgtgt    6480
agaagtactc gccgatagtg gaaaccgacg ccccagcact cgtccgaggg caaggaata    6540 gtgaggtaca gcttggatcg atccggctgc taacaaagcc cgaaaggaag ctgagttggc    6600
```

```
tgctgccacc gctgagcaat aactagcata accccttggg gcctctaaac gggtcttgag    6660
gggttttttg ctgaaaggag gaactatatc cggatgatcg ggcgcgccgg tacccatcaa    6720
ccactttgta caagaaagct gggtctagat atctcgaccc gggtgattgc ggttacatca    6780
tgtacggaaa ataattcta atccttgatt taaatttgaa cttgactatt tatttattct     6840
ttatttcatt ttgtaaatca ttttatgtat ctcctggcaa gcaattttat ccaccttgca    6900
ccaacacctt cgggttccat aatcaaacca ccttaacttc acaccatgct gtaactcaca    6960
ccgcccagca tctccaatgt gaaagaagct aaaatttaat aaacaatcat acgaagcagt    7020
gacaaaatac cagatggtat taatgcttcg ataaaattaa ttggaaagta taaaatggta    7080
gaaaataata aattataatt aatttaagta agataaaaaa taattaaaaa ctaaaatgtt    7140
aaaattttaa aaaaattatt ttaaataata tttaaaaaca ttaaaaatca ttttaaaaaa    7200
tttatttata gaacaattaa ataaatattt cagctaataa aaaacaaaag cttacctagc    7260
cttagaagac aacttgtcca acaattagat gatacccatt gcccttacgt tttctttaac    7320
atcaattatt gttttttgtca acaagctatc ttttagtttt atttttattgg taaaaaatat    7380
gtcgccttca agttgcatca tttaacacat ctcgtcatta gaaaaataaa actcttccct    7440
aaacgattag tagaaaaaat cattcgataa taaataagaa agaaaaatta gaaaaaaata    7500
acttcatttt aaaaaaatca ttaaggctat atttttttaaa tgactaattt tatatagact    7560
gtaactaaaa gtatacaatt tattatgcta tgtatcttaa agaattactt ataaaaatct    7620
acggaagaat atcttacaaa gtgaaaaaca aatgagaaag aatttagtgg gatgattatg    7680
attttatttg aaaattgaaa aataattat taaagacttt agtggagtaa gaaagctttc      7740
ctattagtct tttcttatcc ataaaaaaaa aaaaaaaaat ctagcgtgac agcttttcca    7800
tagattttaa taatgtaaaa tactggtagc agccgaccgt tcaggtaatg gacactgtgg    7860
tcctaacttg caacgggtgc gggcccaatt taataacgcc gtggtaacgg ataaagccaa    7920
gcgtgaagcg gtgaaggtac atctctgact ccgtcaagat tacgaaaccg tcaactacga    7980
aggactcccc gaaatatcat ctgtgtcata acaccaagt cacaccatac atgggcacgc     8040
gtcacaatat gattggagaa cggttccacc gcatatgcta taaaatgccc ccacacccct    8100
cgaccctaat cgcacttcaa ttgcaatcaa attagttcat tctctttgcg cagttccta     8160
cctctccttt caaggttcgt agattctttc cgttttttttt tcttcttctt tattgtttgt    8220
tctacatcag catgatgttg atttgattgt gttttctatc gtttcatcga ttataaattt    8280
tcataatcag aagattcagc ttttattaat gcaagaacgt ccttaattga tgatttttata   8340
accgtaaatt aggtctaatt agagttttttt tcataaagat tttcagatcc gtttacaaca    8400
agccttaatt gttgattctg tagtcgtaga ttaaggtttt tttcatgaac tacttcagat    8460
ccgttaaaca acagccttat tgttgatac ttcagtcgtt tttcaagaaa ttgttcagat      8520
ccgttgataa aagccttatt cgttgattct gtatggtatt tcaagagata ttgctcaggt    8580
cctttagcaa ctaccttatt tgttgattct gtggccatag attaggattt ttttttcacga   8640
aattgcttct tgaaattacg tgatggattt tgattctgat ttatcttgtg attgttgact    8700
ctacagccat ggcccacagc aagcacggcc tgaaggagga gatgaccatg aagtaccaca    8760
tggagggctg cgtgaacggc cacaagttcg tgatcaccgg cgagggcatc ggctaccccct   8820
tcaagggcaa gcagaccatc aacctgtgcg tgatcgaggg cggcccctg cccttcagcg     8880
aggacatcct gagcgccggc ttcaagtacg gcgaccggat cttcaccgag taccccagg     8940
```

```
acatcgtgga ctacttcaag aacagctgcc ccgccggcta cacctggggc cggagcttcc      9000
tgttcgagga cggcgccgtg tgcatctgta acgtggacat caccgtgagc gtgaaggaga      9060
actgcatcta ccacaagagc atcttcaacg gcgtgaactt ccccgccgac ggccccgtga      9120
tgaagaagat gaccaccaac tgggaggcca gctgcgagaa gatcatgccc gtgcctaagc      9180
agggcatcct gaagggcgac gtgagcatgt acctgctgct gaaggacggc ggccggtacc      9240
ggtgccagtt cgacaccgtg tacaaggcca gagcgtgcc cagcaagatg cccgagtggc      9300
acttcatcca gcacaagctg ctgcgggagg accggagcga cgccaagaac agaagtggc      9360 agctgaccga gcacgccatc gccttcccca gcgccctggc ctgagagctc tgattcaatc      9420
aaacggttca tgcttaatca agttgggaac aacaacaaca acaaaaatca agccaatgtt      9480
tgtgggtttt ggtttcattt cattaagatg atctgtttat ctcttttctt cttttaaaa      9540 tttaaagtct ttgtattttg tatgtaaaga tgtaaaatta tgattattag gtggtgcatg      9600
tgtcgcgtca tgggccaatg ttatcctctg cttttaagtt ggaagaggcc caactcatgt      9660
gtgatgtacg gctgtgattg tgtaatttaa tttgcaaaat caaaaataac accagagtca      9720
tatatatgca tctcttttatt ttctctggcc cccaccatgt cttctatgta atatttgttg      9780
ccctcttccc ccaagtatat gacaaggttg ggtttctttt tatccacgcc tgtgcccgtt      9840
atcacttgct atggataatt gaaatccggt gagagtgaga agtggggttg gcttggtggg      9900
tgggtgggtg gatgaattct agtggccggc ccagctgata tccatcacac tggcggccgc      9960
actcgactga attggttccg gcgccagcct gcttt                                9995

<210> SEQ ID NO 38
<211> LENGTH: 9922
<212> TYPE: DNA
<213> ORGANISM: artificial
<220> FEATURE:
<223> OTHER INFORMATION: DNA construct QC351

<400> SEQUENCE: 38
tttgtacaaa cttgttgatg gggttaacat atcataactt cgtataatgt atgctatacg        60
aagttatagg cctggatctt cgaggtcgag cggccgcaga tttaggtgac actatagaat       120
atgcatcact agtaagcttt gctctagatc aaactcacat ccaaacataa catgatatc        180 ttccttacca atcatactaa ttattttggg ttaaatatta atcattattt ttaagatatt       240
aattaagaaa ttaaaagatt ttttaaaaaa atgtataaaa ttatattatt catgattttt       300
catacatttg attttgataa taaatatatt ttttttaatt tcttaaaaaa tgttgcaaga       360
cacttattag acatagtctt gttctgttta caaaagcatt catcatttaa tacattaaaa       420
aatatttaat actaacagta gaatcttctt gtgagtggtg tgggagtagg caacctggca       480
ttgaaacgag agaaagagag tcagaaccag aagacaaata aaaagtatgc aacaaacaaa       540
tcaaaatcaa agggcaaagg ctggggttgg ctcaattggt tgctacattc aattttcaac       600
tcagtcaacg gttgagattc actctgactt ccccaatcta agccgcggat gcaaacggtt       660
gaatctaacc cacaatccaa tctcgttact tagggcttt tccgtcatta actcaccct        720 gccaccggt ttccctataa attggaactc aatgctcccc tctaaactcg tatcgcttca       780
gagttgagac caagacacac tcgttcatat atctctctgc tcttctcttc tcttctacct      840
ctcaaggtac ttttcttctc cctctaccaa atcctagatt ccgtggttca atttcggatc       900
ttgcacttct ggtttgcttt gccttgcttt ttcctcaact gggtccatct aggatccatg       960
tgaaactcta ctctttcttt aatatctgcg gaatacgcgt ttgactttca gatctagtcg      1020
```

```
aaatcatttc ataattgcct ttctttcttt tagcttatga gaaataaaat cactttttt     1080 ttatttcaaa ataaaccttg ggccttgtgc tgactgagat ggggtttggt gattacagaa     1140
ttttagcgaa ttttgtaatt gtacttgttt gtctgtagtt ttgttttgtt ttcttgtttc     1200
tcatacattc cttaggcttc aattttattc gagtataggt cacaatagga attcaaactt     1260
tgagcagggg aattaatccc ttccttcaaa tccagtttgt tgtatatat gtttaaaaaa     1320 tgaaactttt gctttaaatt ctattataac ttttttatg gctgaaattt ttgcatgtgt     1380
ctttgctctc tgttgtaaat ttactgttta ggtactaact ctaggcttgt tgtgcagttt     1440
ttgaagtata accatgccac acaacacaat ggcggccacc gcttccagaa ccacccgatt     1500
ctcttcttcc tcttcacacc ccaccttccc caaacgcatt actagatcca ccctccctct     1560
ctctcatcaa accctcacca aacccaacca cgctctcaaa atcaaatgtt ccatctccaa     1620
accccccacg gcggcgccct tcaccaagga agcgccgacc acggagccct tcgtgtcacg     1680
gttcgcctcc ggcgaacctc gcaagggcgc ggacatcctt gtggaggcgc tggagaggca     1740
gggcgtgacg acggtgttcg cgtaccccgg cggtgcgtcg atggagatcc accaggcgct     1800
cacgcgctcc gccgccatcc gcaacgtgct cccgcgccac gagcagggcg gcgtcttcgc     1860
cgccgaaggc tacgcgcgtt cctccggcct ccccggcgtc tgcattgcca cctccggccc     1920
cggcgccacc aacctcgtga gcggcctcgc cgacgcttta atggacagcg tcccagtcgt     1980
cgccatcacc ggccaggtcg cccgccggat gatcggcacc gacgccttcc aagaaacccc     2040
gatcgtggag gtgagcagat ccatcacgaa gcacaactac ctcatcctcg acgtcgacga     2100
catcccccgc gtcgtcgccg aggctttctt cgtcgccacc tccggccgcc ccggtccggt     2160
cctcatcgac attcccaaag acgttcagca gcaactcgcc gtgcctaatt gggacgagcc     2220
cgttaacctc cccggttacc tcgccaggct gcccaggccc ccgccgagg cccaattgga     2280 acacattgtc agactcatca tggaggccca aaagcccgtt ctctacgtcg gcggtggcag     2340
tttgaattcc agtgctgaat tgaggcgctt tgttgaactc actggtattc ccgttgctag     2400
cactttaatg ggtcttggaa cttttcctat tggtgatgaa tattcccttc agatgctggg     2460
tatgcatggt actgtttatg ctaactatgc tgttacaat agtgatttgt tgcttgcctt     2520
tggggtaagg tttgatgacc gtgttactgg gaagcttgag gcttttgcta gtagggctaa     2580
gattgttcac attgatattg attctgccga gattgggaag aacaagcagg cgcacgtgtc     2640
ggtttgcgcg gatttgaagt tggccttgaa gggaattaat atgattttgg aggagaaagg     2700
agtggagggt aagtttgatc ttggaggttg gagagaagag attaatgtgc agaaacacaa     2760
gtttccattg ggttacaaga cattccagga cgcgatttct ccgcagcatg ctatcgaggt     2820
tcttgatgag ttgactaatg gagatgctat tgttagtact ggggttgggc agcatcaaat     2880
gtgggctgcg cagttttaca agtacaagag accgaggcag tggttgacct caggggggtct     2940 tggagccatg ggttttggat tgcctgcggc tattggtgct gctgttgcta accctggggc     3000
tgttgtggtt gacattgatg gggatggtag tttcatcatg aatgttcagg agttggccac     3060
tataagagtg gagaatctcc cagttaagat attgttgttg aacaatcagc atttgggtat     3120
ggtggttcag ttggaggata ggttctacaa gtccaataga gctcacacct atcttggaga     3180
tccgtctagc gagagcgaga tattcccaaa catgctcaag tttgctgatg cttgtgggat     3240
accggcagcg cgagtgacga agaaggaaga gcttagagcg gcaattcaga gaatgttgga     3300
cacccctggc ccctaccttc ttgatgtcat tgtgccccat caggagcatg tgttgccgat     3360
```

```
gattcccagt aatggatcct tcaaggatgt gataactgag ggtgatggta gaacgaggta    3420
ctgattgcct agaccaaatg ttccttgatg cttgttttgt acaatatata taagataatg    3480
ctgtcctagt tgcaggattt ggcctgtggt gagcatcata gtctgtagta gttttggtag    3540
caagacattt tattttcctt ttatttaact tactacatgc agtagcatct atctatctct    3600
gtagtctgat atctcctgtt gtctgtattg tgccgttgga ttttttgctg tagtgagact    3660
gaaaatgatg tgctagtaat aatatttctg ttagaaatct aagtagagaa tctgttgaag    3720
aagtcaaaag ctaatggaat caggttacat attcaatgtt tttctttttt tagcggttgg    3780
tagacgtgta gattcaactt ctcttggagc tcacctaggc aatcagtaaa atgcatattc    3840
cttttttaac ttgccattta tttacttttaa gtggaaattg tgaccaattt gttcatgtag    3900
aacggatttg gaccattgcg tccacaaaac gtctcttttg ctcgatcttc acaaagcgat    3960
accgaaatcc agagatagtt ttcaaaagtc agaaatggca aagttataaa tagtaaaaca    4020
gaatagatgc tgtaatcgac ttcaataaca agtggcatca cgtttctagt tctagaccca    4080
tcagatcgaa ttaacatatc ataacttcgt ataatgtatg ctatacgaag ttataggcct    4140
ggatccacta gttctagagc ggccgctcga gggggggccc ggtaccggcg cgccgttcta    4200
tagtgtcacc taaatcgtat gtgtatgata cataaggtta tgtattaatt gtagccgcgt    4260
tctaacgaca atatgtccat atggtgcact ctcagtacaa tctgctctga tgccgcatag    4320
ttaagccagc cccgacaccc gccaacaccc gctgacgcgc cctgacgggc ttgtctgctc    4380
ccggcatccg cttacagaca agctgtgacc gtctccggga gctgcatgtg tcagaggttt    4440
tcaccgtcat caccgaaacg cgcgagacga aagggcctcg tgatacgcct attttttatag    4500 gttaatgtca tgaccaaaat cccttaacgt gagttttcgt tccactgagc gtcagacccc    4560
gtagaaaaga tcaaaggatc ttcttgagat cctttttttc tgcgcgtaat ctgctgcttg    4620
caaacaaaaa aaccaccgct accagcggtg gtttgtttgc cggatcaaga gctaccaact    4680
ctttttccga aggtaactgg cttcagcaga gcgcagatac caaatactgt ccttctagtg    4740
tagccgtagt taggccacca cttcaagaac tctgtagcac cgcctacata cctcgctctg    4800
ctaatcctgt taccagtggc tgctgccagt ggcgataagt cgtgtcttac cgggttggac    4860
tcaagacgat agttaccgga taaggcgcag cggtcgggct gaacggggggg ttcgtgcaca    4920 cagcccagct tggagcgaac gacctacacc gaactgagat acctacagcg tgagcattga    4980
gaaagcgcca cgcttcccga agggagaaag gcggacaggt atccggtaag cggcagggtc    5040
ggaacaggag agcgcacgag ggagcttcca gggggaaacg cctggtatct ttatagtcct    5100
gtcgggtttc gccacctctg acttgagcgt cgatttttgt gatgctcgtc aggggggcgg    5160
agcctatgga aaaacgccag caacgcggcc ttttttacggt tcctggcctt ttgctggcct    5220
tttgctcaca tgttctttcc tgcgttatcc cctgattctg tggataaccg tattaccgcc    5280
tttgagtgag ctgataccgc tcgccgcagc cgaacgaccg agcgcagcga gtcagtgagc    5340
gaggaagcgg aagagcgccc aatacgcaaa ccgcctctcc ccgcgcgttg gccgattcat    5400
taatgcaggt tgatcagatc tcgatcccgc gaaattaata cgactcacta gggagacc    5460 acaacggttt ccctctagaa ataattttgt ttaactttaa gaaggagata tacccatgga    5520
aaagcctgaa ctcaccgcga cgtctgtcga gaagtttctg atcgaaaagt tcgacagcgt    5580
ctccgacctg atgcagctct cggagggcga agaatctcgt gctttcagct tcgatgtagg    5640
agggcgtgga tatgtcctgc gggtaaatag ctgcgccgat ggtttctaca agatcgtta    5700 tgtttatcgg cactttgcat cggccgcgct cccgattccg gaagtgcttg acattgggga    5760
```

```
attcagcgag agcctgacct attgcatctc ccgccgtgca cagggtgtca cgttgcaaga   5820
cctgcctgaa accgaactgc ccgctgttct gcagccggtc gcggaggcta tggatgcgat   5880
cgctgcggcc gatcttagcc agacgagcgg gttcggccca ttcggaccgc aaggaatcgg   5940
tcaatacact acatggcgtg atttcatatg cgcgattgct gatccccatg tgtatcactg   6000
gcaaactgtg atggacgaca ccgtcagtgc gtccgtcgcg caggctctcg atgagctgat   6060
gctttgggcc gaggactgcc ccgaagtccg gcacctcgtg cacgcggatt tcggctccaa   6120
caatgtcctg acggacaatg ccgcataac agcggtcatt gactggagcg aggcgatgtt   6180
cggggattcc caatacgagg tcgccaacat cttcttctgg aggccgtggt tggcttgtat   6240
ggagcagcag acgcgctact tcgagcggag gcatccggag cttgcaggat cgccgcggct   6300
ccgggcgtat atgctccgca ttggtcttga ccaactctat cagagcttgg ttgacggcaa   6360
tttcgatgat gcagcttggg cgcagggtcg atgcgacgca atcgtccgat ccggagccgg   6420
gactgtcggg cgtacacaaa tcgcccgcag aagcgcggcc gtctgaccg atggctgtgt   6480
agaagtactc gccgatagtg gaaaccgacg ccccagcact cgtccgaggg caaaggaata   6540
gtgaggtaca gcttggatcg atccggctgc taacaaagcc cgaaaggaag ctgagttggc   6600
tgctgccacc gctgagcaat aactagcata accccttggg gcctctaaac gggtcttgag   6660
gggttttttg ctgaaaggag gaactatatc cggatgatcg ggcgcgccgg tacccatcaa   6720
ccactttgta caagaaagct gggtctagat atctcgaccc gggtgattgc ggttacatca   6780
tgtacggaaa aataattcta atccttgatt taaatttgaa cttgactatt tatttattct   6840
ttatttcatt ttgtaaatca ttttatgtat ctcctggcaa gcaatttat ccaccttgca   6900
ccaacacctt cgggttccat aatcaaacca ccttaacttc acaccatgct gtaactcaca   6960
ccgcccagca tctccaatgt gaaagaagct aaaatttaat aaacaatcat acgaagcagt   7020
gacaaaatac cagatggtat taatgcttcg ataaaattaa ttggaaagta taaaatggta   7080
gaaaataata aattataatt aatttaagta agataaaaaa taattaaaaa ctaaaatgtt   7140
aaaattttaa aaaaattatt ttaaataata tttaaaaaca ttaaaaatca ttttaaaaaa   7200
tttatttata gaacaattaa ataaatattt cagctaataa aaaacaaaag cttacctagc   7260
cttagaagac aacttgtcca acaattagat gatacccatt gcccttacgt tttctttaac   7320
atcaattatt gttttgtca acaagctatc ttttagtttt attttattgg taaaaaatat   7380
gtcgccttca agttgcatca tttaacacat ctcgtcatta gaaaataaa actcttccct   7440
aaacgattag tagaaaaaat cattcgataa taaataagaa agaaaattaa gaaaaaaata   7500
acttcatttt aaaaaatca ttaaggctat atttttaaa tgactaattt tatatagact   7560
gtaactaaaa gtatacaatt tattatgcta tgtatcttaa agaattactt ataaaaatct   7620
acggaagaat atcttacaaa gtgaaaaaca aatgagaaag aatttagtgg gatgattatg   7680
attttatttg aaaattgaaa aataattat taaagacttt agtggagtaa gaaagctttc   7740
ctattagtct tttcttatcc ataaaaaaaa aaaaaaaat ctagcgtgac agcttttcca   7800
tagattttaa taatgtaaaa tactggtagc agccgaccgt tcaggtaatg gacactgtgg   7860
tcctaacttg caacgggtgc gggcccaatt taataacgcc gtggtaacgg ataaagccaa   7920
gcgtgaagcg gtgaaggtac atctctgact ccgtcaagat tacgaaaccg tcaactacga   7980
aggactcccc gaaatatcat ctgtgtcata aacaccaagt cacaccatac atgggcacgc   8040
gtcacaatat gattggagaa cggttccacc gcatatgcta taaaatgccc ccacacccct   8100
```

```
cgaccctaat cgcacttcaa ttgcaatcaa attagttcat tctctttgcg cagttccta      8160 cctctccttt caaggttcgt agatttcttc cgttttttt tcttcttctt tattgtttgt      8220
tctacatcag catgatgttg atttgattgt gttttctatc gtttcatcga ttataaattt     8280
tcataatcag aagattcagc ttttattaat gcaagaacgt ccttaattga tgattttata     8340
accgtaaatt aggtctaatt agagtttttt tcataaagat tttcagatcc gtttacaaca     8400
agccttaatt gttgattctg tagtcgtaga ttaaggtttt tttcatgaac tacttcagat     8460
ccgttaaaca acagccttat tgttgatac ttcagtcgtt tttcaagaaa ttgttcagat      8520
ccgttgataa aagccttatt cgttgattct gtatggtatt tcaagagata ttgctcaggt     8580
cctttagcaa ctaccttatt tgttgattct gtggccatag attaggattt tttttcacga    8640
aattgcttct tgaaattacg tgatggattt tgattctgat ttatcttgtg attgttgact    8700
ctacagccat ggcccacagc aagcacggcc tgaaggagga gatgaccatg aagtaccaca    8760
tggagggctg cgtgaacggc cacaagttcg tgatcaccgg cgagggcatc ggctacccct     8820
tcaagggcaa gcagaccatc aacctgtgcg tgatcgaggg cggcccctg cccttcagcg     8880 aggacatcct gagcgccggc ttcaagtacg gcgaccggat cttcaccgag tacccccagg    8940
acatcgtgga ctacttcaag aacagctgcc ccgccggcta cacctgggc cggagcttcc     9000 tgttcgagga cggcgccgtg tgcatctgta acgtggacat caccgtgagc gtgaaggaga    9060
actgcatcta ccacaagagc atcttcaacg gcgtgaactt ccccgccgac ggccccgtga    9120
tgaagaagat gaccaccaac tgggaggcca gctgcgagaa gatcatgccc gtgcctaagc    9180
agggcatcct gaagggcgac gtgagcatgt acctgctgct gaaggacggc ggccggtacc    9240
ggtgccagtt cgacaccgtg tacaaggcca agagcgtgcc cagcaagatg cccgagtggc    9300
acttcatcca gcacaagctg ctgcgggagg accggagcga cgccaagaac cagaagtggc    9360
agctgaccga gcacgccatc gccttcccca gcgccctggc ctgagagctc tgattgcatt    9420
ttggcaattt tgctagcaca tgtgatcatc aacgtggttt caaaaaaact tgttcctta    9480 cagtagttta tctttgcaga gtcttaggtg tttgttttac cagttatatt tgaagtgtc     9540 cgccgatttc atgtagccgt agccttcaaa actgggttct tgatcggcgg taacatttc     9600 gttgctgttt gttttgatg agtactgttt tttgttttga tggtaaaagt ctgagatttt     9660
caaattcaca agcagccata gggttttagt ccatttcctt tgctgctgag gaggatgtc     9720 ttaaatttgc atttaattta taaggaagtt ttgttaactg tttttatgg tttattattc     9780 cctttgaatt tgaagccatg tgagtgtgtg aggtgtgcgc ctgatctggg attttattt     9840 gaattctagt ggccggccca gctgatatcc atcacactgg cggccgcact cgactgaatt    9900
ggttccggcg ccagcctgct tt                                              9922
```

<210> SEQ ID NO 39
<211> LENGTH: 9939
<212> TYPE: DNA
<213> ORGANISM: artificial
<220> FEATURE:
<223> OTHER INFORMATION: DNA construct QC352

<400> SEQUENCE: 39

```
tttgtacaaa cttgttgatg gggttaacat atcataactt cgtataatgt atgctatacg      60
aagttatagg cctggatctt cgaggtcgag cggccgcaga tttaggtgac actatagaat     120
atgcatcact agtaagcttt gctctagatc aaactcacat ccaaacataa catggatatc     180
ttccttacca atcatactaa ttattttggg ttaaatatta atcattattt ttaagatatt    240
```

```
aattaagaaa ttaaaagatt ttttaaaaaa atgtataaaa ttatattatt catgattttt    300
catacatttg attttgataa taaatatatt tttttttaatt tcttaaaaaa tgttgcaaga    360
cacttattag acatagtctt gttctgttta caaaagcatt catcatttaa tacattaaaa    420
aatatttaat actaacagta gaatcttctt gtgagtggtg tgggagtagg caacctggca    480
ttgaaacgag agaaagagag tcagaaccag aagacaaata aaagtatgc aacaaacaaa      540 tcaaaatcaa agggcaaagg ctggggttgg ctcaattggt tgctacattc aattttcaac    600
tcagtcaacg gttgagattc actctgactt ccccaatcta agccgcggat gcaaacggtt    660
gaatctaacc cacaatccaa tctcgttact tagggggcttt tccgtcatta actcaccct     720 gccacccggt ttccctataa attggaactc aatgctcccc tctaaactcg tatcgcttca    780
gagttgagac caagacacac tcgttcatat atctctctgc tcttctcttc tcttctacct    840
ctcaaggtac ttttcttctc cctctaccaa atcctagatt ccgtggttca atttcggatc    900
ttgcacttct ggtttgcttt gccttgcttt ttcctcaact gggtccatct aggatccatg    960
tgaaactcta ctctttcttt aatatctgcg gaatacgcgt ttgactttca gatctagtcg    1020
aaatcatttc ataattgcct ttctttcttt tagcttatga gaaataaaat cactttttttt   1080 ttatttcaaa ataaaccttg ggccttgtgc tgactgagat ggggtttggt gattacagaa    1140
ttttagcgaa ttttgtaatt gtacttgttt gtctgtagtt ttgttttgtt ttcttgtttc    1200
tcatacattc cttaggcttc aatttttattc gagtataggt cacaatagga attcaaactt   1260
tgagcagggg aattaatccc ttccttcaaa tccagtttgt ttgtatatat gtttaaaaaa    1320
tgaaactttt gctttaaatt ctattataac tttttttatg gctgaaattt ttgcatgtgt    1380
ctttgctctc tgttgtaaat ttactgttta ggtactaact ctaggcttgt tgtgcagttt    1440
ttgaagtata accatgccac acaacacaat ggcggccacc gcttccagaa ccacccgatt    1500
ctcttcttcc tcttcacacc ccaccttccc caaacgcatt actagatcca cctccctct     1560 ctctcatcaa accctcacca aacccaacca cgctctcaaa atcaaatgtt ccatctccaa    1620 acccccacg gcggcgccct tcaccaagga agcgccgacc acggagccct tcgtgtcacg     1680
gttcgcctcc ggcgaacctc gcaagggcgc ggacatcctt gtggaggcgc tggagaggca    1740
gggcgtgacg acggtgttcg cgtacccegg cggtgcgtcg atggagatcc accaggcgct    1800
cacgcgctcc gccgccatcc gcaacgtgct cccgcgccac gagcagggcg gcgtcttcgc    1860
cgccgaaggc tacgcgcgtt cctccggcct ccccggcgtc tgcattgcca cctccggccc    1920
cggcgccacc aacctcgtga gcggcctcgc cgacgcttta atggacagcg tcccagtcgt    1980
cgccatcacc ggccaggtcg cccgccggat gatcggcacc gacgccttcc aagaaacccc    2040
gatcgtggag gtgagcagat ccatcacgaa gcacaactac ctcatcctcg acgtcgacga    2100 catccccgc gtcgtcgccg aggctttctt cgtcgccacc tccggccgcc ccggtccggt      2160
cctcatcgac attcccaaag acgttcagca gcaactcgcc gtgcctaatt gggacgagcc    2220
cgttaacctc cccggttacc tcgccaggct gcccaggccc ccgccgagg cccaattgga      2280 acacattgtc agactcatca tggaggccca aaagcccgtt ctctacgtcg gcggtggcag    2340
tttgaattcc agtgctgaat tgaggcgctt tgttgaactc actggtattc ccgttgctag    2400
cactttaatg ggtcttggaa cttttcctat tggtgatgaa tattcccttc agatgctggg    2460
tatgcatggt actgttttatg ctaactatgc tgttgacaat agtgatttgt tgcttgcctt    2520
tggggtaagg tttgatgacc gtgttactgg gaagcttgag gcttttgcta gtagggctaa    2580
```

```
gattgttcac attgatattg attctgccga gattgggaag aacaagcagg cgcacgtgtc    2640
ggtttgcgcg gatttgaagt tggccttgaa gggaattaat atgattttgg aggagaaagg    2700
agtggagggt aagtttgatc ttggaggttg gagagaagag attaatgtgc agaaacacaa    2760
gtttccattg ggttacaaga cattccagga cgcgatttct ccgcagcatg ctatcgaggt    2820
tcttgatgag ttgactaatg gagatgctat tgttagtact ggggttgggc agcatcaaat    2880
gtgggctgcg cagttttaca agtacaagag accgaggcag tggttgacct caggggtct    2940
tggagccatg ggttttggat tgcctgcggc tattggtgct gctgttgcta accctggggc    3000
tgttgtggtt gacattgatg gggatggtag tttcatcatg aatgttcagg agttggccac    3060
tataagagtg gagaatctcc cagttaagat attgttgttg aacaatcagc atttgggtat    3120
ggtggttcag ttggaggata ggttctacaa gtccaataga gctcacacct atcttggaga    3180
tccgtctagc gagagcgaga tattcccaaa catgctcaag tttgctgatg cttgtgggat    3240
accggcagcg cgagtgacga agaaggaaga gcttagagcg gcaattcaga gaatgttgga    3300
caccctggc ccctaccttc ttgatgtcat tgtgccccat caggagcatg tgttgccgat    3360
gattcccagt aatggatcct tcaaggatgt gataactgag ggtgatggta aacgaggta    3420
ctgattgcct agaccaaatg ttccttgatg cttgttttgt acaatatata taagataatg    3480
ctgtcctagt tgcaggattt ggcctgtggt gagcatcata gtctgtagta gttttggtag    3540
caagacattt tattttcctt ttatttaact tactacatgc agtagcatct atctatctct    3600
gtagtctgat atctcctgtt gtctgtattg tgccgttgga ttttttgctg tagtgagact    3660
gaaaatgatg tgctagtaat aatatttctg ttagaaatct aagtagagaa tctgttgaag    3720
aagtcaaaag ctaatggaat caggttacat attcaatgtt tttctttttt tagcggttgg    3780
tagacgtgta gattcaactt ctcttggagc tcacctaggc aatcagtaaa atgcatattc    3840
ctttttaac ttgccattta tttacttta gtggaaattg tgaccaattt gttcatgtag    3900
aacggatttg gaccattgcg tccacaaaac gtctcttttg ctcgatcttc acaaagcgat    3960
accgaaatcc agagatagtt ttcaaaagtc agaaatggca agttataaa tagtaaaaca    4020
gaatagatgc tgtaatcgac ttcaataaca agtggcatca cgtttctagt tctagaccca    4080
tcagatcgaa ttaacatatc ataacttcgt ataatgtatg ctatacgaag ttataggcct    4140
ggatccacta gttctagagc ggccgctcga ggggggccc ggtaccggcg cgccgttcta    4200
tagtgtcacc taaatcgtat gtgtatgata cataaggtta tgtattaatt gtagccgcgt    4260
tctaacgaca atatgtccat atggtgcact ctcagtacaa tctgctctga tgccgcatag    4320
ttaagccagc cccgacaccc gccaacaccc gctgacgcgc cctgacgggc ttgtctgctc    4380
ccggcatccg cttacagaca agctgtgacc gtctccggga gctgcatgtg tcagaggttt    4440
tcaccgtcat caccgaaacg cgcgagacga aagggcctcg tgatacgcct atttttatag    4500
gttaatgtca tgaccaaaat cccttaacgt gagttttcgt tccactgagc gtcagacccc    4560
gtagaaaaga tcaaaggatc ttcttgagat cctttttttc tgcgcgtaat ctgctgcttg    4620
caaacaaaaa aaccaccgct accagcggtg gtttgtttgc cggatcaaga gctaccaact    4680
ctttttccga aggtaactgg cttcagcaga gcgcagatac caaatactgt ccttctagtg    4740
tagccgtagt taggccacca cttcaagaac tctgtagcac cgcctacata cctcgctctg    4800
ctaatcctgt taccagtggc tgctgccagt ggcgataagt cgtgtcttac cgggttggac    4860
tcaagacgat agttaccgga taaggcgcag cggtcgggct gaacggggg ttcgtgcaca    4920
cagcccagct tggagcgaac gacctacacc gaactgagat acctacagcg tgagcattga    4980
```

```
gaaagcgcca cgcttcccga agggagaaag gcggacaggt atccggtaag cggcagggtc    5040
ggaacaggag agcgcacgag ggagcttcca gggggaaacg cctggtatct ttatagtcct    5100
gtcgggtttc gccacctctg acttgagcgt cgattttgt gatgctcgtc agggggcgg     5160 agcctatgga aaaacgccag caacgcggcc ttttacggt tcctggcctt ttgctggcct     5220
tttgctcaca tgttctttcc tgcgttatcc cctgattctg tggataaccg tattaccgcc    5280
tttgagtgag ctgataccgc tcgccgcagc cgaacgaccg agcgcagcga gtcagtgagc    5340
gaggaagcgg aagagcgccc aatacgcaaa ccgcctctcc ccgcgcgttg gccgattcat    5400
taatgcaggt tgatcagatc tcgatcccgc gaaattaata cgactcacta tagggagacc    5460
acaacggttt ccctctagaa ataattttgt ttaactttaa gaaggagata tacccatgga    5520
aaagcctgaa ctcaccgcga cgtctgtcga agtttctg atcgaaaagt tcgacagcgt       5580
ctccgacctg atgcagctct cggagggcga agaatctcgt gctttcagct tcgatgtagg    5640
agggcgtgga tatgtcctgc gggtaaatag ctgcgccgat ggtttctaca agatcgtta    5700 tgtttatcgg cactttgcat cggccgcgct cccgattccg gaagtgcttg acattgggga    5760
attcagcgag agcctgacct attgcatctc ccgccgtgca cagggtgtca cgttgcaaga    5820
cctgcctgaa accgaactgc ccgctgttct gcagccggtc gcggaggcta tggatgcgat    5880
cgctgcggcc gatcttagcc agacgagcgg gttcggccca ttcggaccgc aaggaatcgg    5940
tcaatacact acatggcgtg atttcatatg cgcgattgct gatccccatg tgtatcactg    6000
gcaaactgtg atggacgaca ccgtcagtgc gtccgtcgcg caggctctcg atgagctgat    6060
gctttgggcc gaggactgcc ccgaagtccg gcacctcgtg cacgcggatt tcggctccaa    6120
caatgtcctg acggacaatg gccgcataac agcggtcatt gactggagcg aggcgatgtt    6180
cggggattcc caatacgagg tcgccaacat cttcttctgg aggccgtggt tggcttgtat    6240
ggagcagcag acgcgctact cgagcggag catccggag cttgcaggat cgccgcggct      6300
ccgggcgtat atgctccgca ttggtcttga ccaactctat cagagcttgg ttgacggcaa    6360
tttcgatgat gcagcttggg cgcagggtcg atgcgacgca atcgtccgat ccggagccgg    6420
gactgtcggg cgtacacaaa tcgcccgcag aagcgcggcc gtctggaccg atggctgtgt    6480
agaagtactc gccgatagtg aaaccgacg ccccagcact cgtccgaggg caaaggaata    6540
gtgaggtaca gcttggatcg atccggctgc taacaaagcc cgaaaggaag ctgagttggc    6600
tgctgccacc gctgagcaat aactagcata accccttggg gcctctaaac gggtcttgag    6660
gggttttttg ctgaaaggag gaactatatc cggatgatcg ggcgcgccgg tacccatcaa    6720
ccactttgta caagaaagct gggtctagat atctcgaccc gggtgattgc ggttacatca    6780
tgtacggaaa ataattcta atccttgatt taaatttgaa cttgactatt tatttattct      6840
ttatttcatt ttgtaaatca tttatgtat ctcctggcaa gcaattttat ccaccttgca      6900
ccaacacctt cgggttccat aatcaaacca ccttaacttc acaccatgct gtaactcaca    6960
ccgcccagca tctccaatgt gaaagaagct aaaatttaat aaacaatcat acgaagcagt    7020
gacaaaatac cagatggtat taatgcttcg ataaaattaa ttggaaagta taaaatggta    7080 gaaataata aattataatt aatttaagta agataaaaaa taattaaaaa ctaaaatgtt    7140
aaaattttaa aaaattatt ttaataata tttaaaaaca ttaaaaatca ttttaaaaaa     7200
tttatttata gaacaattaa ataaatattt cagctaataa aaaacaaaag cttacctagc    7260
cttagaagac aacttgtcca acaattagat gatacccatt gcccttacgt tttctttaac    7320
```

```
atcaattatt gttttttgtca acaagctatc ttttagtttt attttattgg taaaaaatat    7380
gtcgccttca agttgcatca tttaacacat ctcgtcatta gaaaaataaa actcttccct    7440
aaacgattag tagaaaaaat cattcgataa taaataagaa agaaaaatta gaaaaaata     7500 acttcatttt aaaaaaatca ttaaggctat attttttaaa tgactaattt tatatagact    7560
gtaactaaaa gtatacaatt tattatgcta tgtatcttaa agaattactt ataaaaatct    7620
acggaagaat atcttacaaa gtgaaaaaca aatgagaaag aatttagtgg gatgattatg    7680 atttttatttg aaaattgaaa aataattat taaagacttt agtggagtaa gaaagctttc    7740
ctattagtct tttcttatcc ataaaaaaaa aaaaaaaat ctagcgtgac agcttttcca     7800
tagattttaa taatgtaaaa tactggtagc agccgaccgt tcaggtaatg gacactgtgg    7860
tcctaacttg caacgggtgc gggcccaatt taataacgcc gtggtaacgg ataaagccaa    7920
gcgtgaagcg gtgaaggtac atctctgact ccgtcaagat tacgaaaccg tcaactacga    7980
aggactcccc gaaatatcat ctgtgtcata acaccaagt cacaccatac atgggcacgc     8040
gtcacaatat gattggagaa cggttccacc gcatatgcta taaaatgccc ccacaccct     8100 cgaccctaat cgcacttcaa ttgcaatcaa attagttcat tctctttgcg cagttcccta    8160
cctctccttt caaggttcgt agatttcttc cgtttttttt tcttcttctt tattgtttgt    8220
tctacatcag catgatgttg atttgattgt gttttctatc gtttcatcga ttataaattt    8280
tcataatcag aagattcagc ttttattaat gcaagaacgt ccttaattga tgattttata   8340
accgtaaatt aggtctaatt agagtttttt tcataaagat tttcagatcc gtttacaaca    8400
agccttaatt gttgattctg tagtcgtaga ttaaggtttt tttcatgaac tacttcagat    8460
ccgttaaaca acagccttat ttgttgatac ttcagtcgtt tttcaagaaa ttgttcagat    8520
ccgttgataa aagcccttat cgttgattct gtatggtatt tcaagagata ttgctcaggt    8580
cctttagcaa ctaccttatt tgttgattct gtggccatag attaggattt ttttcacga     8640 aattgcttct tgaaattacg tgatggattt tgattctgat ttatcttgtg attgttgact    8700
ctacagccat ggcccacagc aagcacggcc tgaaggagga gatgaccatg aagtaccaca    8760
tggagggctg cgtgaacggc cacaagttcg tgatcaccgg cgagggcatc ggctaccct     8820 tcaagggcaa gcagaccatc aacctgtgcg tgatcgaggg cggccccctg cccttcagcg    8880
aggacatcct gagcgccggc ttcaagtacg gcgaccggat cttcaccgag tacccccagg    8940
acatcgtgga ctacttcaag aacagctgcc ccgccggcta cacctggggc cggagcttcc    9000
tgttcgagga cggcgccgtg tgcatctgta acgtggacat caccgtgagc gtgaaggaga    9060
actgcatcta ccacaagagc atcttcaacg gcgtgaactt ccccgccgac ggccccgtga    9120
tgaagaagat gaccaccaac tgggaggcca gctgcgagaa gatcatgccc gtgcctaagc    9180
agggcatcct gaagggcgac gtgagcatgt acctgctgct gaaggacggc ggccggtacc    9240
ggtgccagtt cgacaccgtg tacaaggcca gagcgtgcc cagcaagatg cccgagtggc     9300
acttcatcca gcacaagctg ctgcgggagg accggagcga cgccaagaac cagaagtggc    9360
agctgaccga gcacgccatc gccttcccca gcgccctggc ctgagagctc tgaggtgttg    9420
gagagctaaa gcttcaagca gagatggccc ttagaaataa tgataaaaac tatatgtagt    9480
ttcaaaactt caaaattatg tagtatgtat tatgttgcac tctggtgttt tgtgtctaaa    9540
caaacaccct tagaataaag tggtcatttc ttgcccttga gcaagttcaa gtgttttgga    9600
cttgtgatgg gtgtgttaag gtcatggttg ccttttatat atatatatat ataaatgttc    9660
ggtaattggt cgcttctgta taaagttcgg ctagttaatc tgaattatga atctctgctt    9720
```

```
ataatattaa actagtacta ttgctggaat aaagtgtcta gtttttctgt ttgttttctt    9780
tgccataata tgcgattttc ctctttgtct ttcacaattg aagtcgaggg tgcgaaactt    9840
cggcatggtg gcaaagtgaa ttctagtggc cggcccagct gatatccatc acactggcgg    9900
ccgcactcga ctgaattggt tccggcgcca gcctgcttt                            9939
```

<210> SEQ ID NO 40
<211> LENGTH: 38
<212> TYPE: DNA
<213> ORGANISM: artificial
<220> FEATURE:
<223> OTHER INFORMATION: primer PSO323364Sac

<400> SEQUENCE: 40

```
aacttgagct ctgaacggga attaaaccta taaacata                              38
```

<210> SEQ ID NO 41
<211> LENGTH: 37
<212> TYPE: DNA
<213> ORGANISM: artificial
<220> FEATURE:
<223> OTHER INFORMATION: primer PSO323364Eco

<400> SEQUENCE: 41

```
aagtagaatt ccatctgtca tcaagtaata tttggtc                               37
```

<210> SEQ ID NO 42
<211> LENGTH: 33
<212> TYPE: DNA
<213> ORGANISM: artificial
<220> FEATURE:
<223> OTHER INFORMATION: primer PSO323364Sac2

<400> SEQUENCE: 42

```
ttatcgagct ctgaagcagt accacactgg ccc                                   33
```

<210> SEQ ID NO 43
<211> LENGTH: 34
<212> TYPE: DNA
<213> ORGANISM: artificial
<220> FEATURE:
<223> OTHER INFORMATION: primer PSO400362Eco

<400> SEQUENCE: 43

```
tagtagaatt cggaggaagt tcgtgatcct caag                                  34
```

<210> SEQ ID NO 44
<211> LENGTH: 34
<212> TYPE: DNA
<213> ORGANISM: artificial
<220> FEATURE:
<223> OTHER INFORMATION: primer PSO332986Sac

<400> SEQUENCE: 44

```
ctattgagct ctgattcaat caaacggttc atgc                                  34
```

<210> SEQ ID NO 45
<211> LENGTH: 28
<212> TYPE: DNA
<213> ORGANISM: artificial
<220> FEATURE:
<223> OTHER INFORMATION: PSO332986Eco

<400> SEQUENCE: 45

-continued atcaagaatt catccaccca cccaccca                28

<210> SEQ ID NO 46
<211> LENGTH: 34
<212> TYPE: DNA
<213> ORGANISM: artificial
<220> FEATURE:
<223> OTHER INFORMATION: primer PSO333268Sac

<400> SEQUENCE: 46
aatctgagct ctgattgcat tttggcaatt ttgc          34

<210> SEQ ID NO 47
<211> LENGTH: 34
<212> TYPE: DNA
<213> ORGANISM: artificial
<220> FEATURE:
<223> OTHER INFORMATION: primer PSO333268Eco

<400> SEQUENCE: 47
actacgaatt caaataaaaa tcccagatca ggcg          34

<210> SEQ ID NO 48
<211> LENGTH: 36
<212> TYPE: DNA
<213> ORGANISM: artificial
<220> FEATURE:
<223> OTHER INFORMATION: primer PSO333209Sac

<400> SEQUENCE: 48
actatgagct ctgaggtgtt ggagagctaa agcttc        36

<210> SEQ ID NO 49
<211> LENGTH: 31
<212> TYPE: DNA
<213> ORGANISM: artificial
<220> FEATURE:
<223> OTHER INFORMATION: primer PSO333209Eco

<400> SEQUENCE: 49
acttagaatt cactttgcca ccatgccgaa g             31

<210> SEQ ID NO 50
<211> LENGTH: 39
<212> TYPE: DNA
<213> ORGANISM: artificial
<220> FEATURE:
<223> OTHER INFORMATION: oligo dT primer 3UTR-1 with tail

<400> SEQUENCE: 50
gcgacacgac ggcacggttt tttttttttt tttttttt     39

<210> SEQ ID NO 51
<211> LENGTH: 20
<212> TYPE: DNA
<213> ORGANISM: artificial
<220> FEATURE:
<223> OTHER INFORMATION: primer 3UTR-2 specific to the tail in primer
      3UTR-1

<400> SEQUENCE: 51
gcgacacgac ggcacggttt                          20

<210> SEQ ID NO 52
<211> LENGTH: 23
<212> TYPE: DNA

```
<213> ORGANISM: artificial
<220> FEATURE:
<223> OTHER INFORMATION: primer 3UTR-3

<400> SEQUENCE: 52
gccgccagtg tgatggatat cag                                          23

<210> SEQ ID NO 53
<211> LENGTH: 26
<212> TYPE: DNA
<213> ORGANISM: artificial
<220> FEATURE:
<223> OTHER INFORMATION: primer SAMS-L

<400> SEQUENCE: 53
gaccaagaca cactcgttca tatatc                                       26

<210> SEQ ID NO 54
<211> LENGTH: 25
<212> TYPE: DNA
<213> ORGANISM: artificial
<220> FEATURE:
<223> OTHER INFORMATION: primer SAMS-L2

<400> SEQUENCE: 54
tctgctgctc aatgtttaca aggac                                        25

<210> SEQ ID NO 55
<211> LENGTH: 31
<212> TYPE: DNA
<213> ORGANISM: artificial
<220> FEATURE:
<223> OTHER INFORMATION: primer SAMS-A1

<400> SEQUENCE: 55
cccaaaataa ttagtatgat tggtaaggaa g                                 31

<210> SEQ ID NO 56
<211> LENGTH: 33
<212> TYPE: DNA
<213> ORGANISM: artificial
<220> FEATURE:
<223> OTHER INFORMATION: primer SAMS-A2

<400> SEQUENCE: 56
gaacaagact atgtctaata agtgtcttgc aac                               33

<210> SEQ ID NO 57
<211> LENGTH: 23
<212> TYPE: DNA
<213> ORGANISM: artificial
<220> FEATURE:
<223> OTHER INFORMATION: primer YFP-1

<400> SEQUENCE: 57
tggcccacag caagcacggc ctg                                          23

<210> SEQ ID NO 58
<211> LENGTH: 23
<212> TYPE: DNA
<213> ORGANISM: artificial
<220> FEATURE:
<223> OTHER INFORMATION: primer YFP-2

<400> SEQUENCE: 58
aggccagggc gctggggaag gcg                                          23
```

<210> SEQ ID NO 59
<211> LENGTH: 22
<212> TYPE: DNA
<213> ORGANISM: artificial
<220> FEATURE:
<223> OTHER INFORMATION: primer YFP-3

<400> SEQUENCE: 59
ggagcgacgc caagaaccag aa                                              22

<210> SEQ ID NO 60
<211> LENGTH: 23
<212> TYPE: DNA
<213> ORGANISM: artificial
<220> FEATURE:
<223> OTHER INFORMATION: primer YFP-A

<400> SEQUENCE: 60
tgcagttctc cttcacgctc acg                                             23

<210> SEQ ID NO 61
<211> LENGTH: 24
<212> TYPE: DNA
<213> ORGANISM: artificial
<220> FEATURE:
<223> OTHER INFORMATION: primer UBQ-S2

<400> SEQUENCE: 61
gcgcagttcc ctacctctcc tttc                                            24

<210> SEQ ID NO 62
<211> LENGTH: 22
<212> TYPE: DNA
<213> ORGANISM: artificial
<220> FEATURE:
<223> OTHER INFORMATION: SAMS forward primer (SAMS-48F)

<400> SEQUENCE: 62
ggaagaagag aatcgggtgg tt                                              22

<210> SEQ ID NO 63
<211> LENGTH: 23
<212> TYPE: DNA
<213> ORGANISM: artificial
<220> FEATURE:
<223> OTHER INFORMATION: FAM labeled SAMS probe (SAMS-88T)

<400> SEQUENCE: 63
attgtgttgt gtggcatggt tat                                             23

<210> SEQ ID NO 64
<211> LENGTH: 23
<212> TYPE: DNA
<213> ORGANISM: artificial
<220> FEATURE:
<223> OTHER INFORMATION: SAMS reverse primer (SAMS-134R)

<400> SEQUENCE: 64
ggcttgttgt gcagttttg aag                                              23

<210> SEQ ID NO 65
<211> LENGTH: 20
<212> TYPE: DNA
<213> ORGANISM: artificial
<220> FEATURE:

```
<223> OTHER INFORMATION: YFP forward primer (YFP-67F)

<400> SEQUENCE: 65
aacggccaca agttcgtgat                                              20

<210> SEQ ID NO 66
<211> LENGTH: 20
<212> TYPE: DNA
<213> ORGANISM: artificial
<220> FEATURE:
<223> OTHER INFORMATION: FAM labeled YFP probe (YFP-88T)

<400> SEQUENCE: 66
accggcgagg gcatcggcta                                              20

<210> SEQ ID NO 67
<211> LENGTH: 20
<212> TYPE: DNA
<213> ORGANISM: artificial
<220> FEATURE:
<223> OTHER INFORMATION: YFP reverse primer (YFP-130R)

<400> SEQUENCE: 67
cttcaagggc aagcagacca                                              20

<210> SEQ ID NO 68
<211> LENGTH: 24
<212> TYPE: DNA
<213> ORGANISM: artificial
<220> FEATURE:
<223> OTHER INFORMATION: HSP forward primer (HSP-F1)

<400> SEQUENCE: 68
caaacttgac aaagccacaa ctct                                         24

<210> SEQ ID NO 69
<211> LENGTH: 20
<212> TYPE: DNA
<213> ORGANISM: artificial
<220> FEATURE:
<223> OTHER INFORMATION: VIC labeled HSP probe (HSP probe)

<400> SEQUENCE: 69
ctctcatctc atataaatac                                              20

<210> SEQ ID NO 70
<211> LENGTH: 21
<212> TYPE: DNA
<213> ORGANISM: artificial
<220> FEATURE:
<223> OTHER INFORMATION: HSP reverse primer (HSP-R1)

<400> SEQUENCE: 70
ggagaaattg gtgtcgtgga a                                            21

<210> SEQ ID NO 71
<211> LENGTH: 23
<212> TYPE: DNA
<213> ORGANISM: artificial
<220> FEATURE:
<223> OTHER INFORMATION: primer SamsPro-F

<400> SEQUENCE: 71
ttcttgtgag tggtgtggga gta                                          23
```

```
<210> SEQ ID NO 72
<211> LENGTH: 16
<212> TYPE: DNA
<213> ORGANISM: artificial
<220> FEATURE:
<223> OTHER INFORMATION: FAM labeled MGB probe SamsPro-T

<400> SEQUENCE: 72
caacctggca ttgaaa                                              16

<210> SEQ ID NO 73
<211> LENGTH: 27
<212> TYPE: DNA
<213> ORGANISM: artificial
<220> FEATURE:
<223> OTHER INFORMATION: primer SamsPro-R

<400> SEQUENCE: 73
gtcttctggt tctgactctc tttctct                                  27

<210> SEQ ID NO 74
<211> LENGTH: 20
<212> TYPE: DNA
<213> ORGANISM: artificial
<220> FEATURE:
<223> OTHER INFORMATION: primer YFP-139F

<400> SEQUENCE: 74
tgccagttcg acaccgtgta                                          20

<210> SEQ ID NO 75
<211> LENGTH: 15
<212> TYPE: DNA
<213> ORGANISM: artificial
<220> FEATURE:
<223> OTHER INFORMATION: FAM labeled MGB probe YFP-160T

<400> SEQUENCE: 75
aaggccaaga gcgtg                                               15

<210> SEQ ID NO 76
<211> LENGTH: 18
<212> TYPE: DNA
<213> ORGANISM: artificial
<220> FEATURE:
<223> OTHER INFORMATION: primer YFP-195R

<400> SEQUENCE: 76
ccactcgggc atcttgct                                            18

<210> SEQ ID NO 77
<211> LENGTH: 28
<212> TYPE: DNA
<213> ORGANISM: artificial
<220> FEATURE:
<223> OTHER INFORMATION: primer PSO323364S1

<400> SEQUENCE: 77
aaacctattc tccacccagt tatcaagg                                 28

<210> SEQ ID NO 78
<211> LENGTH: 26
<212> TYPE: DNA
<213> ORGANISM: artificial
<220> FEATURE:
<223> OTHER INFORMATION: primer PSO323364R1
```

<400> SEQUENCE: 78
agagcccata agttacggaa cataac                                                                      26

<210> SEQ ID NO 79
<211> LENGTH: 27
<212> TYPE: DNA
<213> ORGANISM: artificial
<220> FEATURE:
<223> OTHER INFORMATION: primer PSO400362S1

<400> SEQUENCE: 79
gcttgtgttc tgccagtatg atgagac                                                                     27

<210> SEQ ID NO 80
<211> LENGTH: 28
<212> TYPE: DNA
<213> ORGANISM: artificial
<220> FEATURE:
<223> OTHER INFORMATION: Primer PSO400362R1

<400> SEQUENCE: 80
ttaaagatga tgtaaccaga ccaatagc                                                                    28

<210> SEQ ID NO 81
<211> LENGTH: 23
<212> TYPE: DNA
<213> ORGANISM: artificial
<220> FEATURE:
<223> OTHER INFORMATION: primer PSO332982F

<400> SEQUENCE: 81
agcactctac caccaggtcg taa                                                                         23

<210> SEQ ID NO 82
<211> LENGTH: 24
<212> TYPE: DNA
<213> ORGANISM: artificial
<220> FEATURE:
<223> OTHER INFORMATION: primer PSO332986JK-A

<400> SEQUENCE: 82
ttacacaatc acagccgtac atca                                                                        24

<210> SEQ ID NO 83
<211> LENGTH: 18
<212> TYPE: DNA
<213> ORGANISM: artificial
<220> FEATURE:
<223> OTHER INFORMATION: primer PSO333268F

<400> SEQUENCE: 83
gaaagacccc accggagc                                                                               18

<210> SEQ ID NO 84
<211> LENGTH: 20
<212> TYPE: DNA
<213> ORGANISM: artificial
<220> FEATURE:
<223> OTHER INFORMATION: primer PSO333268R

<400> SEQUENCE: 84
aacgaaaatg ttaccgccga                                                                             20

<210> SEQ ID NO 85
<211> LENGTH: 20

```
<212> TYPE: DNA
<213> ORGANISM: artificial
<220> FEATURE:
<223> OTHER INFORMATION: primer PSO333209F

<400> SEQUENCE: 85
tcatgggagt ggcaccagtt                                                 20

<210> SEQ ID NO 86
<211> LENGTH: 25
<212> TYPE: DNA
<213> ORGANISM: artificial
<220> FEATURE:
<223> OTHER INFORMATION: primer PSO333209JK-A

<400> SEQUENCE: 86
tgaccttaac acacccatca caagt                                           25

<210> SEQ ID NO 87
<211> LENGTH: 100
<212> TYPE: DNA
<213> ORGANISM: artificial
<220> FEATURE:
<223> OTHER INFORMATION: AttL1

<400> SEQUENCE: 87
caaataatga ttttattttg actgatagtg acctgttcgt tgcaacaaat tgataagcaa     60 tgcttttttta taatgccaac tttgtacaaa aaagcaggct                         100

<210> SEQ ID NO 88
<211> LENGTH: 100
<212> TYPE: DNA
<213> ORGANISM: artificial
<220> FEATURE:
<223> OTHER INFORMATION: AttL2

<400> SEQUENCE: 88
caaataatga ttttattttg actgatagtg acctgttcgt tgcaacaaat tgataagcaa     60
tgctttctta taatgccaac tttgtacaag aaagctgggt                          100

<210> SEQ ID NO 89
<211> LENGTH: 125
<212> TYPE: DNA
<213> ORGANISM: artificial
<220> FEATURE:
<223> OTHER INFORMATION: AttR1

<400> SEQUENCE: 89
acaagtttgt acaaaaaagc tgaacgagaa acgtaaaatg atataaatat caatatatta     60
aattagattt tgcataaaaa acagactaca taatactgta aaacacaaca tatccagtca    120
ctatg                                                                125

<210> SEQ ID NO 90
<211> LENGTH: 125
<212> TYPE: DNA
<213> ORGANISM: artificial
<220> FEATURE:
<223> OTHER INFORMATION: AttR2

<400> SEQUENCE: 90
accactttgt acaagaaagc tgaacgagaa acgtaaaatg atataaatat caatatatta     60
aattagattt tgcataaaaa acagactaca taatactgta aaacacaaca tatccagtca    120
``` ctatg                                                              125

<210> SEQ ID NO 91
<211> LENGTH: 21
<212> TYPE: DNA
<213> ORGANISM: artificial
<220> FEATURE:
<223> OTHER INFORMATION: AttB1

<400> SEQUENCE: 91
caagtttgta caaaaaagca g                                             21

<210> SEQ ID NO 92
<211> LENGTH: 21
<212> TYPE: DNA
<213> ORGANISM: artificial
<220> FEATURE:
<223> OTHER INFORMATION: AttB2

<400> SEQUENCE: 92
cagctttctt gtacaaagtg g                                             21

<210> SEQ ID NO 93
<211> LENGTH: 20
<212> TYPE: DNA
<213> ORGANISM: Artificial
<220> FEATURE:
<223> OTHER INFORMATION: VIC labeled MGB probe ATPS-117T

<400> SEQUENCE: 93
agattgggcc agaggatcct                                               20

<210> SEQ ID NO 94
<211> LENGTH: 28
<212> TYPE: DNA
<213> ORGANISM: artificial
<220> FEATURE:
<223> OTHER INFORMATION: PSO323364UTR2 primer

<400> SEQUENCE: 94
gacactatta tctgactatc ccaacacg                                      28

<210> SEQ ID NO 95
<211> LENGTH: 23
<212> TYPE: DNA
<213> ORGANISM: artificial
<220> FEATURE:
<223> OTHER INFORMATION: PSO323364UTR3 primer

<400> SEQUENCE: 95
agagttaggt tcccgtcaca agg                                           23

<210> SEQ ID NO 96
<211> LENGTH: 31
<212> TYPE: DNA
<213> ORGANISM: artificial
<220> FEATURE:
<223> OTHER INFORMATION: PSO323364UTR4 primer

<400> SEQUENCE: 96
gccttcaagt aatataagat tagttaggtg g                                  31

<210> SEQ ID NO 97
<211> LENGTH: 24
<212> TYPE: DNA
<213> ORGANISM: artificial

```
<220> FEATURE:
<223> OTHER INFORMATION: PSO323364UTR5 primer

<400> SEQUENCE: 97
ccataatagg gcatgacaca atcc                                              24

<210> SEQ ID NO 98
<211> LENGTH: 32
<212> TYPE: DNA
<213> ORGANISM: artificial
<220> FEATURE:
<223> OTHER INFORMATION: PSO323364UTR6 primer

<400> SEQUENCE: 98
ggatcttaag taagacttac tcatctgttc aa                                     32

<210> SEQ ID NO 99
<211> LENGTH: 30
<212> TYPE: DNA
<213> ORGANISM: artificial
<220> FEATURE:
<223> OTHER INFORMATION: PSO323364UTR7 primer

<400> SEQUENCE: 99
cgattcctga cttaagaata gagatgtaat                                        30

<210> SEQ ID NO 100
<211> LENGTH: 23
<212> TYPE: DNA
<213> ORGANISM: artificial
<220> FEATURE:
<223> OTHER INFORMATION: PSO400362UTR2 primer

<400> SEQUENCE: 100
tcctgacctg tccttccata tcc                                               23

<210> SEQ ID NO 101
<211> LENGTH: 27
<212> TYPE: DNA
<213> ORGANISM: artificial
<220> FEATURE:
<223> OTHER INFORMATION: PSO400362UTR3 primer

<400> SEQUENCE: 101
ggtctccgca tagtaatagt agacagg                                           27

<210> SEQ ID NO 102
<211> LENGTH: 32
<212> TYPE: DNA
<213> ORGANISM: artificial
<220> FEATURE:
<223> OTHER INFORMATION: PSO400362UTR4 primer

<400> SEQUENCE: 102
atataagaac ctaagcagaa gtaattaagt gc                                     32

<210> SEQ ID NO 103
<211> LENGTH: 24
<212> TYPE: DNA
<213> ORGANISM: artificial
<220> FEATURE:
<223> OTHER INFORMATION: PSO400362UTR5 primer

<400> SEQUENCE: 103
ggagctcaat ggagaaccca taac                                              24
```

```
<210> SEQ ID NO 104
<211> LENGTH: 34
<212> TYPE: DNA
<213> ORGANISM: artificial
<220> FEATURE:
<223> OTHER INFORMATION: PSO400362UTR6 primer

<400> SEQUENCE: 104
atgtagatat acatatctaa cataattggc aatc                                34

<210> SEQ ID NO 105
<211> LENGTH: 23
<212> TYPE: DNA
<213> ORGANISM: artificial
<220> FEATURE:
<223> OTHER INFORMATION: PSO400362UTR7 primer

<400> SEQUENCE: 105
atcgacatga atcccaatat ccc                                           23

<210> SEQ ID NO 106
<211> LENGTH: 23
<212> TYPE: DNA
<213> ORGANISM: artificial
<220> FEATURE:
<223> OTHER INFORMATION: PSO332986UTR2 primer

<400> SEQUENCE: 106
gcattcccgt tgaagctgat aag                                           23

<210> SEQ ID NO 107
<211> LENGTH: 26
<212> TYPE: DNA
<213> ORGANISM: artificial
<220> FEATURE:
<223> OTHER INFORMATION: PSO332986UTR3 primer

<400> SEQUENCE: 107
gcaaatgcta aatcacaaga atcaag                                        26

<210> SEQ ID NO 108
<211> LENGTH: 26
<212> TYPE: DNA
<213> ORGANISM: artificial
<220> FEATURE:
<223> OTHER INFORMATION: PSO332986UTR4 primer

<400> SEQUENCE: 108
ggttagaatc tgtcaatcga attccc                                        26

<210> SEQ ID NO 109
<211> LENGTH: 25
<212> TYPE: DNA
<213> ORGANISM: artificial
<220> FEATURE:
<223> OTHER INFORMATION: PSO332986UTR5 primer

<400> SEQUENCE: 109 cctcccttc aataaaattc cttcc                                          25

<210> SEQ ID NO 110
<211> LENGTH: 29
<212> TYPE: DNA
<213> ORGANISM: artificial
<220> FEATURE:
<223> OTHER INFORMATION: PSO332986UTR6 primer
```

```
<400> SEQUENCE: 110 cccttttta cttatgagaa ttcatcatc                                29

<210> SEQ ID NO 111
<211> LENGTH: 30
<212> TYPE: DNA
<213> ORGANISM: artificial
<220> FEATURE:
<223> OTHER INFORMATION: PSO332986UTR7 primer

<400> SEQUENCE: 111
aagaacttac aatcaaggtc tcatctttta                              30

<210> SEQ ID NO 112
<211> LENGTH: 26
<212> TYPE: DNA
<213> ORGANISM: artificial
<220> FEATURE:
<223> OTHER INFORMATION: PSO333268UTR2 primer

<400> SEQUENCE: 112
tctaaacgtt gaatggaata tggaac                                  26

<210> SEQ ID NO 113
<211> LENGTH: 23
<212> TYPE: DNA
<213> ORGANISM: artificial
<220> FEATURE:
<223> OTHER INFORMATION: PSO333268UTR3 primer

<400> SEQUENCE: 113
ataagaatgg cttgcgtgat tgg                                     23

<210> SEQ ID NO 114
<211> LENGTH: 24
<212> TYPE: DNA
<213> ORGANISM: artificial
<220> FEATURE:
<223> OTHER INFORMATION: PSO333268UTR4 primer

<400> SEQUENCE: 114
aatcaacaag gggataaaga aggc                                    24

<210> SEQ ID NO 115
<211> LENGTH: 24
<212> TYPE: DNA
<213> ORGANISM: artificial
<220> FEATURE:
<223> OTHER INFORMATION: PSO333268UTR5 primer

<400> SEQUENCE: 115
caccgactca attaggctag gatg                                    24

<210> SEQ ID NO 116
<211> LENGTH: 32
<212> TYPE: DNA
<213> ORGANISM: artificial
<220> FEATURE:
<223> OTHER INFORMATION: PSO333268UTR6 primer

<400> SEQUENCE: 116
tgtaatagac tatcgaacag tatatgcact tg                           32

<210> SEQ ID NO 117
```

```
<211> LENGTH: 22
<212> TYPE: DNA
<213> ORGANISM: artificial
<220> FEATURE:
<223> OTHER INFORMATION: PSO333268UTR7 primer

<400> SEQUENCE: 117
cctccaccga tcataaccct tc                                              22

<210> SEQ ID NO 118
<211> LENGTH: 31
<212> TYPE: DNA
<213> ORGANISM: artificial
<220> FEATURE:
<223> OTHER INFORMATION: PSO333209UTR2 primer

<400> SEQUENCE: 118
gcagttcatc attaaaataa tccttcttat c                                    31

<210> SEQ ID NO 119
<211> LENGTH: 23
<212> TYPE: DNA
<213> ORGANISM: artificial
<220> FEATURE:
<223> OTHER INFORMATION: PSO333209UTR3 primer

<400> SEQUENCE: 119
aaggggacca acaatgacct cag                                             23

<210> SEQ ID NO 120
<211> LENGTH: 28
<212> TYPE: DNA
<213> ORGANISM: artificial
<220> FEATURE:
<223> OTHER INFORMATION: PSO333209UTR4 primer

<400> SEQUENCE: 120
aagtagtgaa atgaaaagga aggagttg                                        28

<210> SEQ ID NO 121
<211> LENGTH: 23
<212> TYPE: DNA
<213> ORGANISM: artificial
<220> FEATURE:
<223> OTHER INFORMATION: PSO333209UTR5 primer

<400> SEQUENCE: 121
tgccaaacat gattacgacc ttg                                             23

<210> SEQ ID NO 122
<211> LENGTH: 27
<212> TYPE: DNA
<213> ORGANISM: artificial
<220> FEATURE:
<223> OTHER INFORMATION: PSO333209UTR6 primer

<400> SEQUENCE: 122
tgattgacaa tgatatacaa atgctcg                                         27

<210> SEQ ID NO 123
<211> LENGTH: 26
<212> TYPE: DNA
<213> ORGANISM: artificial
<220> FEATURE:
<223> OTHER INFORMATION: PSO333209UTR7 primer

<400> SEQUENCE: 123
```

```
aagtctcctt ttcaatattc tcagcc                                          26

<210> SEQ ID NO 124
<211> LENGTH: 1564
<212> TYPE: DNA
<213> ORGANISM: Glycine max

<400> SEQUENCE: 124
gagctctgaa cgggaattaa acctataaac ataaatataa ataatatata taaacctaag     60
tgtctaagtt ccataaatta agctgtagtc tctggcttaa acatgttag gtttgtttat     120 acaagtagtt ggatgtttgg agtacttcgg tcttttgcgt accatcaata tttaagaact    180
aagttagtta tgttccgtaa cttatgggct cttaattaaa ctatatctgc acaaaattat    240
atatatatca aatgtgatgg tatgtggact ataaaaagat atggttgaga accacaaact    300
ttgaaacttc gaataatata ttgccagtga cagtcttgtt gatttgttat agcaagtcct    360
attttcttaa tcattgcttt gttttaacgt acctagattt cataacttttt gtctttgtct   420 caagctgaac ctaatgatga tagtaatatt aacttattgt ataggggtat ttcataggat   480
aaaaaatgat gtgcaattac gtgtagacca aatattactt gatgacagat ggataaatat    540
tttaaaactt tctcatgttg atagttctttt ctactgtttt tcattgaact ttaaaatttt   600
aatagtttgg caagtaaatt gtgtaactaa cgtgttggga tagtcagata atagtgtcag    660
agatcacctt catataaacg gaaagacaac caagcatgtg ctctcatgaa ctagcattta   720
atccccatat atattaaaaa gtggtcacat tatagccacc ttagaaatat ttgttaacaa   780
ttcacccgct tttttccttg tgacgggaac ctaactcttg tccatgactg catcatgcag    840
tgacgtcttc agtcttcaca tttgcctcgt aaactcacgt aatcgccgta tcctttttta    900
ttaaggaaat taatagcaat aatagaaaac tatcactatc attttgatat ggaactcata    960
aatagttgct aactattggt ctcatttatc atagtcatag ataatttatt taataatatt    1020
ttcttttatc aataaatatt aattattagt ttgtttctat ttgttagtaa aataaattaa    1080
actcgtagac ttttttttta accacctaac taatcttata ttacttgaag gctatgatca    1140
tgggttcatg gcattattgg aagtgggata atgttgtgag taattctaac tgaaagacat    1200
tgtcatgttg tgagtaccaa gttaggccag tgatgatatc agagtaagag cattcgtggt    1260
gtaccaaact tcaactttag tttagcttcc aaactcttat tcgtcctggg attgtgtcat    1320
gccctattat ggaaacaagg acaatttctt ctagtcttta actttgtacc tatgccatgc    1380
caaaaggaac tgcagcatct atgagccact cgttctattc agtcacatgt tttatgtgcg    1440
gaattcaatt tcaacacccg cacgtgatgt gataaggaag attcacgtgg tgggtcggcc    1500
actgagacag aacatggtta aatatttgaa ttttgaacag atgagtaagt cttacttaag    1560
atcc                                                                 1564

<210> SEQ ID NO 125
<211> LENGTH: 1472
<212> TYPE: DNA
<213> ORGANISM: Glycine max

<400> SEQUENCE: 125
gagctctgaa gcagtaccac actggcccaa aaaaaaaatt catgtgctta atttctagct     60
gtgagagaca attaagtgta tgaccaataa aatggttttg ttgtaggacc aagtctgaga    120
gacgccaagc accacatgaa taaaataacc aaagcttggt ttgtattgta gccttctcta   180
```

```
atgctattgg tctggttaca tcatctttaa ttccccttta tatatgcata tgtttattat        240
ttattgattt atccttgaaa gagtacaatt taacttttaa ttttttattt tatctttaat        300
ttaatcaaaa gatttagttg tcagaaagaa agaacgaagg gtgagataat gatgatagat        360
catccatggg ccgccgttaa tagccttttt cagtctctaa gtcaaagtta accctacaga        420
atccatgtct aagtctaaca accataaggt caaagcctcc gtcaattttc agatgcgatt        480
tcagtttatt cctcattgta ataaacccta ttttcagagt aacttgagga tcacgaactt        540
cctccatata tggttgacat aattttttcaa atattttgag atgctgcttt cattctcaat        600
ttttatataa gtgtctctca acttttaaag taaagggtca aatttgttat agaccttatt        660
ttatgttagg ctggctttga gtgccagttc caaaaggata tggaaggaca ggtcaggaaa        720
taaaacaatt cgagggatga tttgcaatgc ttcggtttac tcttaataaa gaagaggtaa        780
gcttttgaaa ggtaaaggtt atattatata tgttcataca tcctgtctac tattactatg        840
cggagacctt tgcttttctct actattacta tgcgggggacc ttttcttaa gaattacgtt        900 ttttaatttt atacataaga attacattat tcaaatcctt aaaatgattt attagatgta        960
agtaacatta agactttgtg tgcgtgcact taattacttc tgcttaggtt cttatataga       1020
tataaaaaga gagaaaggga gaaaaaacaa aataaaagtg agatgaagag aagttaagtg       1080
tataaatata attactaatt cacctgcaaa caagctagtt tttatttatt taattttggc       1140
acagatcttt ttttcttcttt aattttattt caggaaacta gctagattga tgaagtatat       1200
tgttagcatt ccctttattt tattcttcat aaaactttt ttcttttgtt atgggttctc       1260
cattgagctc ctttaattag gttcacatct ccattgtgat cgattttgaa tcgtatattc       1320
tctttgtgtc tcgaaagcgt ggatttaggt acatgcattg gtaggattga cgatctattg       1380
tgtcatgact tgacccttca aggttgttgg tgatctattg tgttccatgg ttacatttga       1440
ttgccaatta tgttagatat gtatatctac at                                     1472
```

<210> SEQ ID NO 126
<211> LENGTH: 1553
<212> TYPE: DNA
<213> ORGANISM: Glycine max

<400> SEQUENCE: 126

```
gagctctgat tcaatcaaac ggttcatgct taatcaagtt gggaacaaca acaacaacaa         60
aaatcaagcc aatgtttgtg ggttttggtt tcatttcatt aagatgatct gtttatctct        120
tttcttcttt ttaaaattta aagtctttgt attttgtatg taaagatgta aaattatgat        180
tattaggtgg tgcatgtgtc gcgtcatggg ccaatgttat cctctgcttt taagttggaa        240
gaggcccaac tcatgtgtga tgtacggctg tgattgtgta atttaatttg caaaatcaaa        300
aataacacca gagtcatata tatgcatctc tttatttttct ctggcccccca ccatgtcttc        360 tatgtaatat ttgttgccct cttcccccaa gtatatgaca aggttgggtt tctttttatc        420
cacgcctgtg cccgttatca cttgctatgg ataattgaaa tccggtgaga gtgagaagtg        480
gggttggctt ggtgggtggg tgggtggatg aatgatgtct cttgcttaat atgggaccac        540
ttttcttcct caataatgca catattctag tgttgtccat ttaataatga tttgtgatca        600
tagccttggg gaaaaaacgt acactgtttt tatattttt ttgtgctaaa attaagacaa        660
gtttgatctt atcagcttca acgggaatgc cgcttcctcc tagttacttc catggaatcc        720
tctcacggaa aagacgtggc actcgtggga tgggtaactg aggagaaagc attaataatt        780
tgacacgtat aaatcattat catatactca tgcttgattc ttgtgattta gcatttgctt        840
```

| | | |
|---|---|---|
| tttttttttt tttatcaaaa tatcaaatgc caactaggaa taaaatgtga tttctgcttt | 900 | |
| tctaattgtg aatgtcactg ataacattgc ctcaaaagtt cttcaaataa tccacttcag | 960 | |
| aattagcgag aataaaagag acctcaaccg atgtctaatc actaaacaaa tactttgttg | 1020 | |
| gattggagag aaaatgtagg gaattcgatt gacagattct aacccttttt acttttact | 1080 | |
| aattaaaggt tcagttaatt tgtcaggatt ggatttgtat cctgtaaaaa atttgagttt | 1140 | |
| caattgttga cttacgagaa ttttgtggat aaaataactt ataagtacca agtcttgata | 1200 | |
| tgatcttggt gaattctcaa agtcataacc caagtcactt aacttttaac ttttttttaa | 1260 | |
| gaaaatctaa tcactttcat taatacactg gttagtttaa ttggaaggaa ttttattgaa | 1320 | |
| agggaggaaa tttaacaaaa tgcagggata ttttagggga aaacaaatga aaattcttat | 1380 | |
| tatttaatga atttatggt catatatatt aataagataa aataatttta tatcgtcatc | 1440 | |
| taataaaaaa ttatcattag gaaaaattaa taaatttatt atttataata atttatgatt | 1500 | |
| aaaaaataat tttatattat caatgatgat gaattctcat aagttaaaaa ggg | 1553 | |

<210> SEQ ID NO 127
<211> LENGTH: 1509
<212> TYPE: DNA
<213> ORGANISM: Glycine max

<400> SEQUENCE: 127

| | | |
|---|---|---|
| gagctctgat tgcattttgg caattttgct agcacatgtg atcatcaacg tggtttcaaa | 60 | |
| aaaacttgtt cctttacagt agtttatctt tgcagagtct taggtgtttg ttttaccagt | 120 | |
| tatattttga agtgtccgcc gatttcatgt agccgtagcc ttcaaaactg ggttcttgat | 180 | |
| cggcggtaac attttcgttg ctgtttgttt ttgatgagta ctgttttttg ttttgatggt | 240 | |
| aaaagtctga gattttcaaa ttcacaagca gccatagggt tttagtccat ttcctttgct | 300 | |
| gctgaggagg gatgtcttaa atttgcattt aatttataag gaagttttgt taactgtttt | 360 | |
| ttatggttta ttattccctt tgaatttgaa gccatgtgag tgtgtgaggt gtgcgcctga | 420 | |
| tctgggattt ttatttgagc tctaaataat gcgatcgtag attcgtagtt tcactaatta | 480 | |
| ctaaagaaca tttgttgctt gtgaaatgag catctataga caaacgagtg aggaaaatat | 540 | |
| atatttagtt ctacaattct aaagttccat attccattca acgtttagaa aatctcataa | 600 | |
| ttgaatctca tgcactcctg aaatgttgca catgtcattc tatgtgtaga gcatcttatt | 660 | |
| atacacatgt taaataaggc tatcaagaaa ataaggctac gaggaggata caggaacgtt | 720 | |
| gttagacatt ttaagcgctt cgtttaaatt ttttgaggtc accaatcacg caagccattc | 780 | |
| ttatgattga ttgataaatg tcagaaaaag actacgcacg caaatatatt gaaatattgt | 840 | |
| atgaaaacat tgaaataaag tttcatttat caaatctctt aatcaacttt gagagaccta | 900 | |
| ctcttttcat gatatcgata tcaccaaaat aggttttgct taatatctta agtcttaata | 960 | |
| aagccttctt tatcccttg ttgatttta ttatatgtct acaccttagt ttgaaacaaa | 1020 | |
| caaaaaatac ttgaaataat tttaagaatt aagaattctg attattaata gcgtagattt | 1080 | |
| ttcacaatgc atgagcaaac tgaatgaaaa tcacgaaact ggaagctgat tgatgaagcg | 1140 | |
| cattgtggaa aaaacagtaa acagatgtaa tgaatgttac caaaggttgt ccttgatggg | 1200 | |
| gatgagtttg tactacaaaa tccagttttcc ttgtcatgtt ccgacaactc aatcccccat | 1260 | |
| gcgaccatcc tagcctaatt gagtcggtgc aaaatttgtt ggatgggttc atctattcat | 1320 | |
| agcactattt ggtgtgaccg gaaatagtct taatcatctt gttatgtagc actctgattg | 1380 | |

-continued

```
aataacaaca aaatgagaga gattcataga ctgtgcagat atgacaatgt acaatagatg    1440
ataacttaaa agaattaatt gatactacct atattaacaa gtgcatatac tgttcgatag    1500
tctattaca                                                           1509

<210> SEQ ID NO 128
<211> LENGTH: 1366
<212> TYPE: DNA
<213> ORGANISM: Glycine max

<400> SEQUENCE: 128
gagctctgag gtgttggaga gctaaagctt caagcagaga tggcccttag aaataatgat      60
aaaaactata tgtagtttca aaacttcaaa attatgtagt atgtattatg ttgcactctg     120
gtgttttgtg tctaaacaaa caccctttaga ataaagtggt catttcttgc ccttgagcaa    180
gttcaagtgt tttggacttg tgatgggtgt gttaaggtca tggttgcctt ttatatatat    240
atatatataa atgtttggta attggtcgct tctgtataaa gttcggccag ttaatctgaa    300
ttatgaatct ctgcttataa tattaaacta gtactattgc tggaataaag tgtctagttt    360
ttctgtttgt tttcttttgcc ataatatgcg attttcctct ttgtctttca caattgaagt   420
cgagggtgcg aaacttcggc atggtggcaa agtggcattt agatgataaa tagcatttat    480
tttaatggat gtgacttgtg agtattgaag ggcagtgatg taagagcatt taatggttaa    540
gctcttgtga gaatcatgaa tttcaacaaa gaactgataa gaaggattat tttaatgatg    600
aactgcataa atttagaaat ttcataaacc actctggttg aaatttgaaa atattctaaa    660
aatgtttcgt ttagaggata taaagggtga ttttttcttca ttttttcttt agaggttaca   720
aatgcaattt tttattataa acaatgcatt atctcaaaaa cacgtgctga ggtcattgtt   780 ggtcccctttc tactttttgct aaagactcat caagattgtg attttcagtt ccatgtgtgt   840
gtttctgact tggatggtga tggatacgta aacatgctcg tgatttgtga ctgattaaaa    900
aatttgtttt catttatatg aatacaattg aggcttacat tattacagca attccttacg    960 ttatttttgta tacttacttt acttttctttt caactccttc cttttcattt cactacttaa   1020
ttaatacgta tcgcacgcat ttatatcttt ttttcctcta cctatttatt tctctctctc   1080
tctctctctc atgtatactt atttttttatg gtgtgaaact ttttcttttt tcacaattcc   1140
tattcttatc tgattcaagg tcgtaatcat gtttggcaaa atcttttttc caaataagct    1200
taaagaaagt aattcagaaa aaattttata gttatttttt ttatttatat atagataatg    1260
ttaagtactt caaatttaaa caaaaggaat tattttctgt tattgaaata aatattttta    1320
cagcatttta taaatgattc gagcatttgt atatcattgt caatca                   1366
```

SOYBEAN TRANSCRIPTION TERMINATORS AND USE IN EXPRESSION OF TRANSGENIC GENES IN PLANTS

This application is a Divisional of U.S. application Ser. No. 14/255,267, filed Apr. 17, 2014, now U.S. Pat. No. 9,273,311 issued Mar. 1, 2016, which is a Divisional of U.S. application Ser. No. 13/561,150, filed Jul. 30, 2012, now U.S. Pat. No. 8,741,634, issued Jun. 3, 2014, which is a Divisional of U.S. application Ser. No. 13/288,992, filed Nov. 4, 2011, now U.S. Pat. No. 8,263,399, issued Sep. 11, 2012, which is a Divisional of U.S. application Ser. No. 12/486,793 filed Jun. 18, 2009, now U.S. Pat. No. 8,080,413, issued Dec. 20, 2011, which claims the benefit of U.S. Provisional Application No. 61/073,389, filed Jun. 18, 2008, the entire contents of which are herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named 20160119_BB1645USDIV4_SeqLst.txt created on Jan. 19, 2016, and having a size of 137 kilobytes. The sequence listing contained in this ASCII formatted document is part of the specification and is herein incorporated by reference in its entirety.

FIELD OF THE INVENTION

This invention relates to novel plant transcription terminators MYB2, KTI1, PIP1, EF1A2, and MTH1 isolated from soybean and their use in the regulation of gene expression in plants.

BACKGROUND OF THE INVENTION

Recent advances in plant genetic engineering have opened new doors to engineer plants with improved characteristics or traits, such as plant disease resistance, insect resistance, drought tolerance, extreme temperature tolerance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated into a plant's genome. The newly integrated gene (or genes) coding sequence can then be expressed in the plant cell to exhibit the desired new trait or characteristic. It is important that appropriate regulatory signals be present in proper configurations in order to obtain expression of the newly inserted gene coding sequence in the plant cell. These regulatory signals typically include a promoter region, a 5' non-translated leader sequence, and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The insertion of promoter sequences in recombinant DNA constructs dictates when and where in the plant the introduced DNA sequences will be expressed.

In contrast, sequences located downstream (3') to the relevant coding sequence, i.e. transcription terminators, appear to control quantitative levels of expression (Ali and Taylor, *Plant Mol. Biol.* 46:251-61 (2001)). Transcription terminators function to stop transcription and also have important effects on the processing and degradation of RNA strands generated by transcription. In recombinant DNA constructs, terminators are typically inserted immediately after the 3'-end of the translated region of a gene of interest.

Recombinant DNA constructs may contain more than one gene cassette, each consisting of a promoter, gene of interest, and a terminator. If RNA transcription is not terminated effectively, the transcription of one gene cassette may interfere with the expression of a gene in another cassette. Similarly, unwanted transcription of trait-unrelated (downstream) sequences may interfere with trait performance. Weak terminators, for example, can generate read-through, thereby affecting the expression of genes located in neighboring expression cassettes (Padidam and Cao, *Biotechniques* 31:328-30, 332-4 (2001)). However, the use of appropriate transcription terminators in recombinant DNA constructs can minimize read-through into downstream sequences (e.g., other expression cassettes) and allow more efficient recycling of RNA polymerase II, thereby improving gene expression.

Often, the same transcription termination sequence is used multiple times in one transgenic organism, sometimes resulting in unintended silencing. Thus, there is a demand for alternative transcription termination sequences. Unfortunately, the prediction of functional, efficient transcription termination sequences by bioinformatics is difficult since virtually no conserved sequences exist to allow for such a prediction. Thus, there is an ongoing interest in the isolation of novel terminators that are capable of controlling transcription termination and that improve gene expression.

SUMMARY OF THE INVENTION

In a first embodiment, this invention concerns a terminator, wherein said terminator comprises the nucleotide sequence set forth in SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128; a full-length complement of SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128; or a nucleotide sequence having at least 90% sequence identity, based on the BLASTN method of alignment, when compared to the sequence set forth in SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128, or a full-length complement thereof.

In a second embodiment, the invention concerns a terminator, wherein said terminator is a nucleotide sequence comprising a fragment of SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128; a full-length complement of a fragment of SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128; or a nucleotide sequence having at least 90% sequence identity, based on the BLASTN method of alignment, when compared to the fragment of SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128, or a full-length complement thereof.

In a third embodiment, this invention concerns a recombinant DNA construct comprising a promoter, at least one heterologous nucleic acid fragment, and the terminator of the invention, wherein the promoter, heterologous nucleic acid fragment, and terminator are operably linked.

In a fourth embodiment, this invention concerns a vector, cell, plant, or seed comprising a recombinant DNA construct of the present disclosure.

In a fifth embodiment, this invention concerns plants comprising this recombinant DNA construct and seeds obtained from such plants.

In a sixth embodiment, this invention concerns a method of expressing at least one heterologous nucleic acid fragment in a plant cell which comprises:

(a) transforming a plant cell with the recombinant DNA construct described above;
(b) growing fertile mature plants from the transformed plant cell of step (a);
(c) selecting plants containing the transformed plant cell wherein the heterologous nucleic acid fragment is expressed.

In a seventh embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

BRIEF DESCRIPTION OF SEQUENCES AND DRAWINGS

The invention can be more fully understood from the following detailed descriptions, the drawings, and the sequence descriptions that form a part of this application. The Sequence Listing contains the one letter code for nucleotide sequence characters and the three letter codes for amino acids as defined in conformity with the IUPAC-IUBMB standards described in *Nucleic Acids Research* 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

SEQ ID NO:1 is the nucleotide sequence of the soybean MYB2 terminator cloned into DNA construct QC339.

SEQ ID NO:2 is the nucleotide sequence of the soybean KTI1 terminator cloned into DNA construct QC340.

SEQ ID NO:3 is the nucleotide sequence of the soybean PIP1 terminator cloned into DNA construct QC350.

SEQ ID NO:4 is the nucleotide sequence of the soybean EF1A2 terminator cloned into DNA construct QC351.

SEQ ID NO:5 is the nucleotide sequence of the soybean MTH1 terminator cloned into DNA construct QC352.

SEQ ID NO:6 is the 1061 bp nucleotide sequence of the putative soybean transcription factor MYB2 gene PSO323364. Nucleotides 1 to 144 represent 5' untranslated sequence, while the coding sequence is found at nucleotides 145 to 756, with the translation initiation codon at nucleotides 145 to 147 and the termination codon at nucleotides 757 to 759. Nucleotides 757 to 1061 are part of the 3' untranslated sequence.

SEQ ID NO:7 is the 882 bp nucleotide sequence of the putative soybean Kunitz trypsin inhibitor KTI1 gene PSO400362. Nucleotides 1 to 30 represent 5' untranslated sequence, while the coding sequence is found at nucleotides 31 to 639, with the translation initiation codon at nucleotides 31 to 33 and the termination codon at nucleotides 640 to 642. Nucleotides 640 to 882 are part of the 3' untranslated sequence.

SEQ ID NO:8 is the 1247 bp nucleotide sequence of the putative soybean aquaporin protein PIP1 gene PSO332986. Nucleotides 1 to 67 represent 5' untranslated sequence, while the coding sequence is found at nucleotides 68 to 934, with the translation initiation codon at nucleotides 68 to 70 and the termination codon at nucleotides 935 to 937. Nucleotides 935 to 1247 are part of the 3' untranslated sequence.

SEQ ID NO:9 is the 1772 bp nucleotide sequence of the putative soybean translation elongation factor EF1 alpha homolog (EF1A2) gene PSO333268. Nucleotides 1 to 86 represent 5' untranslated sequence, while the coding sequence is found at nucleotides 87 to 1427, with the translation initiation codon at nucleotides 87 to 89 and the termination codon at nucleotides 1428 to 1430. Nucleotides 1428 to 1772 are part of the 3' untranslated sequence.

SEQ ID NO:10 is the 574 bp nucleotide sequence of the putative soybean type 2 metallothionein MTH1 gene PSO333209. Nucleotides 1 to 78 represent 5' untranslated sequence, while the coding sequence is found at nucleotides 79 to 315, with the translation initiation codon at nucleotides 79 to 81 and the termination codon at nucleotides 316 to 318. Nucleotides 316 to 574 are part of the 3' untranslated sequence.

SEQ ID NO:11 is the predicted amino acid sequence of the protein encoded by the putative soybean transcription factor MYB2 gene PSO323364 (SEQ ID NO:6).

SEQ ID NO:12 is the predicted amino acid sequence of the protein encoded by the putative soybean Kunitz trypsin inhibitor KTI1 gene PSO400362 (SEQ ID NO:7).

SEQ ID NO:13 is the predicted amino acid sequence of the protein encoded by the putative soybean aquaporin protein PIP1 gene PSO332986 (SEQ ID NO:8).

SEQ ID NO:14 is the predicted amino acid sequence of the protein encoded by the putative soybean translation elongation factor EF1 alpha homolog (EF1A2) gene PSO333268 (SEQ ID NO:9).

SEQ ID NO:15 is the predicted amino acid sequence of the protein encoded by the putative soybean type 2 metallothionein MTH1 gene PSO333209 (SEQ ID NO:10).

SEQ ID NO:16 is the MPSS tag sequence specific to the PSO323364 gene.

SEQ ID NO:17 is the MPSS tag sequence specific to the PSO400362 gene.

SEQ ID NO:18 is the MPSS tag sequence specific to the PSO332986 gene.

SEQ ID NO:19 is the MPSS tag sequence specific to the PSO333268 gene.

SEQ ID NO:20 is the sense primer ATPS-87F for qRT-PCR of the endogenous control gene ATP sulfurylase (ATPS).

SEQ ID NO:21 is the antisense primer ATPS-161R for qRT-PCR of the endogenous control gene ATPS.

SEQ ID NO:22 is the sense primer PSO0323364F for qRT-PCR analysis of the PSO323364 gene.

SEQ ID NO:23 is the antisense primer PSO323364R for qRT-PCR analysis of the PSO323364 gene.

SEQ ID NO:24 is the sense primer PSO400362F for qRT-PCR analysis of the PSO400362 gene.

SEQ ID NO:25 is the antisense primer PSO0400362R for qRT-PCR analysis of the PSO400362 gene.

SEQ ID NO:26 is the sense primer PSO0332986F for qRT-PCR analysis of the PSO332986 gene.

SEQ ID NO:27 is the antisense primer PSO332986R for qRT-PCR analysis of the PSO332986 gene.

SEQ ID NO:28 is the sense primer PSO333268F for qRT-PCR analysis of the PSO333268 gene.

SEQ ID NO:29 is the antisense primer PSO333268R for qRT-PCR analysis of the PSO333268 gene.

SEQ ID NO:30 is the sense primer PSO0333209F for qRT-PCR analysis of the PSO333209 gene.

SEQ ID NO:31 is the antisense primer PSO0333209R for qRT-PCR analysis of the PSO333209 gene.

SEQ ID NO:32 is the 5232 bp sequence of the DNA construct QC315.

SEQ ID NO:33 is the 5492 bp sequence of the DNA construct QC327.

SEQ ID NO:34 is the 8409 bp sequence of the DNA construct QC324i.

SEQ ID NO:35 is the 10017 bp sequence of the DNA construct QC339.

SEQ ID NO:36 is the 10031 bp sequence of the DNA construct QC340.

SEQ ID NO:37 is the 9995 bp sequence of the DNA construct QC350.

SEQ ID NO:38 is the 9922 bp sequence of the DNA construct QC351.

SEQ ID NO:39 is the 9939 bp sequence of the DNA construct QC352.

SEQ ID NO:40 is the oligonucleotide primer PSO0323364Sac used as a sense primer in the PCR amplification of the MYB2 terminator (PSO323364) from the soybean genome. A SacI recognition site (GAGCTC) was added for subsequent cloning.

SEQ ID NO:41 is the oligonucleotide primer PSO323364Eco used as an antisense primer in the PCR amplification of the MYB2 terminator (PSO323364) from the soybean genome. An EcoRI recognition site (GAATTC) was added for subsequent cloning.

SEQ ID NO:42 is the oligonucleotide primer PSO400362Sac used as a sense primer in the PCR amplification of the KTI1 terminator (PSO400362) from the soybean genome. A SacI recognition site (GAGCTC) was added for subsequent cloning.

SEQ ID NO:43 is the oligonucleotide primer PSO400362Eco used as an antisense primer in the PCR amplification of the KTI1 terminator (PSO400362) from the soybean genome. An EcoRI recognition site (GAATTC) was added for subsequent cloning.

SEQ ID NO:44 is the oligonucleotide primer PSO332986Sac used as a sense primer in the PCR amplification of the PIP1 terminator (PSO332986) from the soybean genome. A SacI recognition site (GAGCTC) was added for subsequent cloning.

SEQ ID NO:45 is the oligonucleotide primer PSO332986Eco used as an antisense primer in the PCR amplification of the PIP1 terminator (PSO332986) from the soybean genome. An EcoRI recognition site (GAATTC) was added for subsequent cloning.

SEQ ID NO:46 is the oligonucleotide primer PSO333268Sac used as a sense primer in the PCR amplification of the EF1A2 terminator (PSO333268) from the soybean genome. A SacI recognition site (GAGCTC) was added for subsequent cloning.

SEQ ID NO:47 is the oligonucleotide primer PSO333268Eco used as an antisense primer in the PCR amplification of the EF1A2 terminator (PSO333268) from the soybean genome. An EcoRI recognition site (GAATTC) was added for subsequent cloning.

SEQ ID NO:48 is the oligonucleotide primer PSO333209Sac used as a sense primer in the PCR amplification of the MTH1 terminator (PSO333209) from the soybean genome. A SacI recognition site (GAGCTC) was added for subsequent cloning.

SEQ ID NO:49 is the oligonucleotide primer PSO333209Eco used as an antisense primer in the PCR amplification of the MTH1 terminator (PSO333209) from the soybean genome. An EcoRI recognition site (GAATTC) was added for subsequent cloning.

SEQ ID NO:50 is the antisense oligo dT primer 3UTR-1 used to synthesize first strand cDNA from polyadenylated mRNA. A non-specific tail sequence included on the 5' end of the primer will be used as a priming site for subsequent PCR.

SEQ ID NO:51 is the antisense primer 3UTR-2, which is specific to the tail sequence in primer 3UTR-1.

SEQ ID NO:52 is the antisense primer 3UTR-3, which is specific to a region downstream of terminators MYB2, KTI1, PIP1, EF1A2, and MTH1 in their respective constructs QC339, QC340, QC350, QC351, and QC352.

SEQ ID NO:53 is the sense primer SAMS-L, which is specific to an S-adenosylmethionine synthetase (SAMS) gene and is used in a diagnostic PCR to check for soybean genomic DNA presence in total RNA or cDNA.

SEQ ID NO:54 is the antisense primer SAMS-L2, which is specific to an S-adenosylmethionine synthetase (SAMS) gene and is used in a diagnostic PCR to check for soybean genomic DNA presence in total RNA or cDNA.

SEQ ID NO:55 is the antisense primer SAMS-A1, which is specific to the SAMS promoter used in constructs QC339, QC340, QC350, QC351, and QC352.

SEQ ID NO:56 is the antisense primer SAMS-A2, which is specific to the SAMS promoter.

SEQ ID NO:57 is the sense primer YFP-1, which is specific to the ZS-YELLOW1 N1 (YFP) gene used in constructs QC339, QC340, QC350, QC351, and QC352.

SEQ ID NO:58 is the antisense primer YFP-2, which is specific to the YFP gene.

SEQ ID NO:59 is the sense primer YFP-3, which is specific to the YFP gene.

SEQ ID NO:60 is the antisense primer YFP-A, which is specific to the YFP gene.

SEQ ID NO:61 is the sense primer UBQ-S2, which is specific to the soybean UBQ promoter used in constructs QC339, QC340, QC350, QC351, and QC352.

SEQ ID NO:62 is the sense primer SAMS-48F used in quantitative PCR analysis of SAMS:ALS transgene copy numbers.

SEQ ID NO:63 is the FAM labeled (fluorescein) DNA probe SAMS-88T used in quantitative PCR analysis of SAMS:ALS transgene copy numbers.

SEQ ID NO:64 is the antisense primer SAMS-134R used in quantitative PCR analysis of SAMS:ALS transgene copy numbers.

SEQ ID NO:65 is the sense primer YFP-67F used in quantitative PCR analysis of YFP transgene copy numbers.

SEQ ID NO:66 is the FAM labeled (fluorescein) DNA probe YFP-88T used in quantitative PCR analysis of YFP transgene copy numbers.

SEQ ID NO:67 is the antisense primer YFP-130R used in quantitative PCR analysis of YFP transgene copy numbers.

SEQ ID NO:68 is the sense primer HSP-F1 used as an endogenous control gene primer HSP-F1 in quantitative PCR analysis of transgene copy numbers.

SEQ ID NO:69 is the VIC-labeled DNA probe HSP used as an endogenous control gene probe in quantitative PCR analysis of transgene copy numbers.

SEQ ID NO:70 is the antisense primer HSP-R1 used as an endogenous control gene primer in quantitative PCR analysis of transgene copy numbers.

SEQ ID NO:71 is the sense primer SamsPro-F used in quantitative RT-PCR analysis of SAMS promoter transcripts.

SEQ ID NO:72 is the FAM-labeled (fluorescein) DNA MGB probe SamsPro-T used in quantitative RT-PCR analysis of SAMS promoter transcripts.

SEQ ID NO:73 is the antisense primer SamsPro-R used in quantitative RT-PCR analysis of SAMS promoter transcripts.

SEQ ID NO:74 is the sense primer YFP-139F used in quantitative RT-PCR analysis of YFP transgene transcripts.

SEQ ID NO:75 is the FAM-labeled (fluorescein) DNA MGB probe YFP-160T used in quantitative RT-PCR analysis of YFP transgene transcripts.

SEQ ID NO:76 is the antisense primer YFP-195R used in quantitative RT-PCR analysis of YFP transgene transcripts.

SEQ ID NO:77 is the sense primer PSO323364S1 used for RT-PCR analysis of endogenous gene PSO323364 transcripts.

SEQ ID NO:78 is the antisense primer PSO323364R1 used for RT-PCR analysis of endogenous gene PSO323364 transcripts.

SEQ ID NO:79 is the sense primer PSO400362S1 used for RT-PCR analysis of endogenous gene PSO400362 transcripts.

SEQ ID NO:80 is the antisense primer PSO400362R1 used for RT-PCR analysis of endogenous gene PSO400362 transcripts.

SEQ ID NO:81 is the sense primer PSO0332982F used for RT-PCR analysis of endogenous gene PSO332986 transcripts.

SEQ ID NO:82 is the antisense primer PSO332986JK-A used for RT-PCR analysis of endogenous gene PSO332986 transcripts.

SEQ ID NO:83 is the sense primer PSO333268F used for RT-PCR analysis of endogenous gene PSO333268 transcripts.

SEQ ID NO:84 is the antisense primer PSO0333268R used for RT-PCR analysis of endogenous gene PSO333268 transcripts.

SEQ ID NO:85 is the sense primer PSO0333209F used for RT-PCR analysis of endogenous gene PSO333209 transcripts.

SEQ ID NO:86 is the antisense primer PSO0333209JK-A used for RT-PCR analysis of endogenous gene PSO333209 transcripts.

SEQ ID NO:87 is the recombination site attL1 sequence in the Gateway cloning system (Invitrogen).

SEQ ID NO:88 is the recombination site attL2 sequence in the Gateway cloning system (Invitrogen).

SEQ ID NO:89 is the recombination site attR1 sequence in the Gateway cloning system (Invitrogen).

SEQ ID NO:90 is the recombination site attR2 sequence in the Gateway cloning system (Invitrogen).

SEQ ID NO:91 is the recombination site attB1 sequence in the Gateway cloning system (Invitrogen).

SEQ ID NO:92 is the recombination site attB2 sequence in the Gateway cloning system (Invitrogen).

SEQ ID NO:93 is the VIC-labeled (fluorescein) DNA MGB probe ATPS-117T used as the endogenous control in quantitative RT-PCR analysis of YFP and SAMS promoter transcripts.

SEQ ID NO:94 is the sequence of primer PSO0323364UTR2.

SEQ ID NO:95 is the sequence of primer PSO323364UTR3.

SEQ ID NO:96 is the sequence of primer PSO323364UTR4.

SEQ ID NO:97 is the sequence of primer PSO323364UTR5.

SEQ ID NO:98 is the sequence of primer PSO323364UTR6.

SEQ ID NO:99 is the sequence of primer PSO323364UTR7.

SEQ ID NO:100 is the sequence of primer PSO0400362UTR2.

SEQ ID NO:101 is the sequence of primer PSO400362UTR3.

SEQ ID NO:102 is the sequence of primer PSO400362UTR4.

SEQ ID NO:103 is the sequence of primer PSO400362UTR5.

SEQ ID NO:104 is the sequence of primer PSO400362UTR6.

SEQ ID NO:105 is the sequence of primer PSO400362UTR7.

SEQ ID NO:106 is the sequence of primer PSO332986UTR2.

SEQ ID NO:107 is the sequence of primer PSO332986UTR3.

SEQ ID NO:108 is the sequence of primer PSO332986UTR4.

SEQ ID NO:109 is the sequence of primer PSO332986UTR5.

SEQ ID NO:110 is the sequence of primer PSO332986UTR6.

SEQ ID NO: 111 is the sequence of primer PSO332986UTR7.

SEQ ID NO:112 is the sequence of primer PSO0333268UTR2.

SEQ ID NO:113 is the sequence of primer PSO333268UTR3.

SEQ ID NO:114 is the sequence of primer PSO333268UTR4.

SEQ ID NO:115 is the sequence of primer PSO333268UTR5.

SEQ ID NO:116 is the sequence of primer PSO333268UTR6.

SEQ ID NO:117 is the sequence of primer PSO333268UTR7.

SEQ ID NO:118 is the sequence of primer PSO0333209UTR2.

SEQ ID NO:119 is the sequence of primer PSO333209UTR3.

SEQ ID NO:120 is the sequence of primer PSO333209UTR4.

SEQ ID NO:121 is the sequence of primer PSO333209UTR5.

SEQ ID NO:122 is the sequence of primer PSO333209UTR6.

SEQ ID NO:123 is the sequence of primer PSO0333209UTR7.

SEQ ID NO:124 is the nucleotide sequence of the PSO323364 MYB2L terminator.

SEQ ID NO:125 is the nucleotide sequence of the PSO400362 KTI1L terminator.

SEQ ID NO:126 is the nucleotide sequence of the PSO332986 PIP1L terminator.

SEQ ID NO:127 is the nucleotide sequence of the PSO333268 EF1A2L terminator.

SEQ ID NO:128 is the nucleotide sequence of the PSO333209 MTH1L terminator.

FIG. 1 shows the logarithm of relative gene expression quantifications of five soybean genes PSO323364 (MYB2), PSO400362 (KTI1), PSO332986 (PIP1), PSO333268 (EF1A2), and PSO333209 (MTH1) in 14 different soybean tissues by quantitative RT-PCR. The gene expression profiles indicate that MYB2 is predominately expressed in flowers; KTI1 is predominately expressed in developing seeds; and PIP1, EF1A2, and MTH1 are expressed similarly in all evaluated tissues.

FIGS. 2A, 2B, 2C, and 2D show plasmids QC315, QC327, QC324i, and QC339, respectively. QC327 was made from QC315 by replacing the NOS terminator in QC315 with the MYB2 terminator. The UBQ:YFP:MYB2 cassette in QC327 was linked to the SAMS:HRA cassette in QC324i to make the final construct QC339.

FIGS. 3A, 3B, 3C, and 3D show maps of transformation ready constructs: QC340 for the KTI1 terminator, QC350 for the PIP1 terminator, QC351 for the EF1A2 terminator, and QC352 for the MTH1 terminator, respectively.

Figure 6:
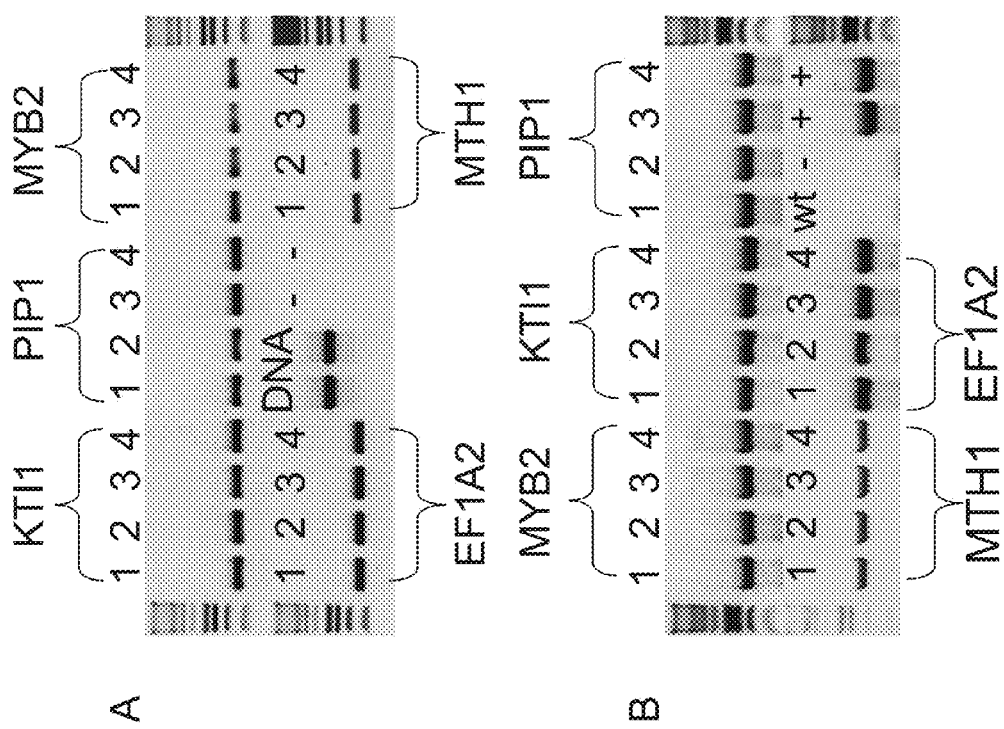

FIG. 6 shows YFP reporter gene expression in four representative transgenic events (samples 1, 2, 3, and 4) for each of the five terminators, MYB2, KTI1, PIP1, EF1A2, and MTH1. A) An RT-PCR check of genomic DNA contamination in RNA samples using primers SAMS-L/SAMS-L2. No genomic DNA-specific band was amplified from any of the RNA samples, and all RNA samples produced the RNA-specific band. B) A YFP expression check by RT-PCR with YFP1/YFP-2 primers. YFP transcripts were detected in all transgenic RNA samples. The two negative controls, wild type RNA (wt) and no template control (−), and the positive controls QC393 (+) and QC350 (+) all worked as expected.

Figure 7:
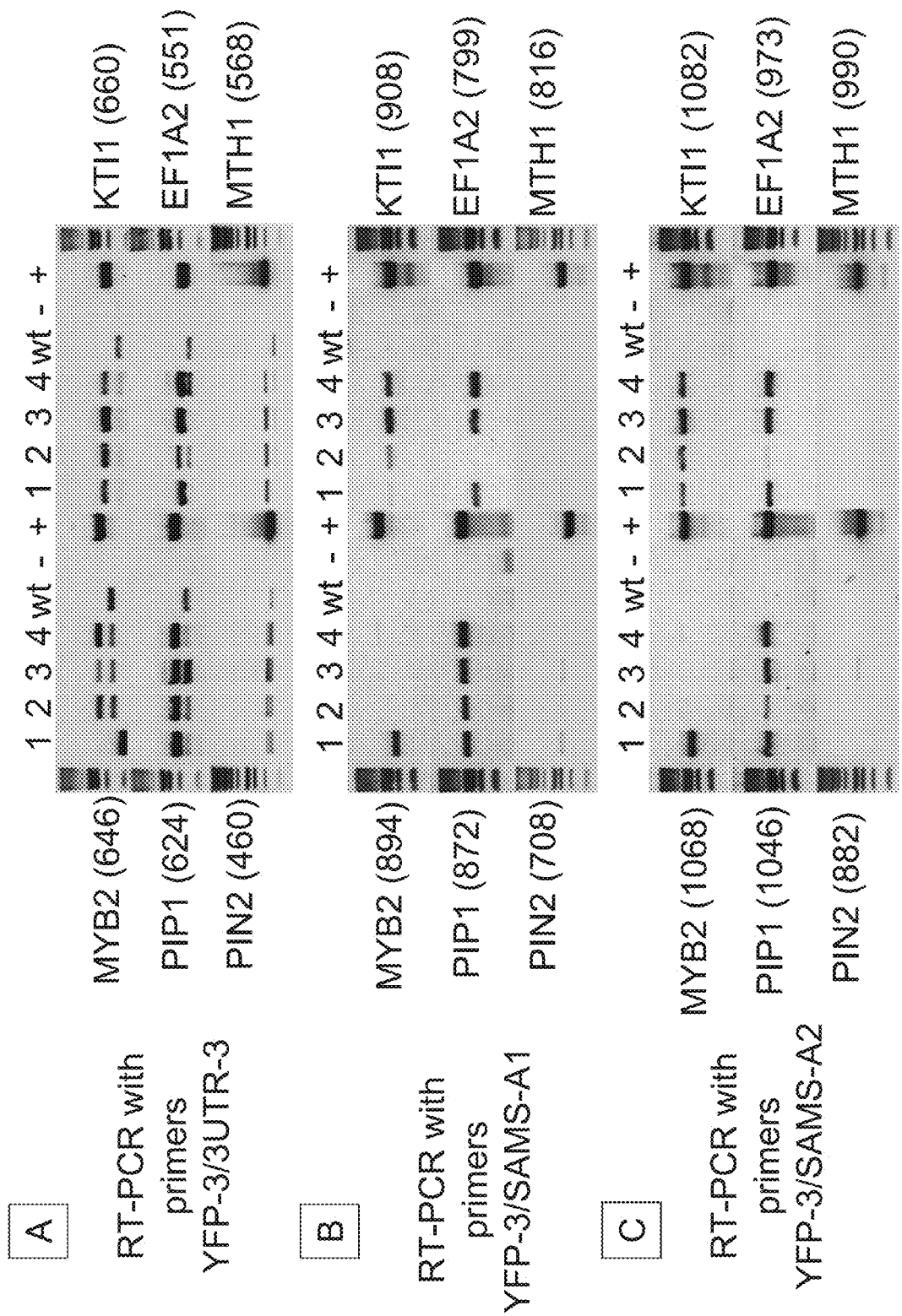

FIG. 7 shows the transcription termination check by RT-PCR of the five novel terminators, MYB2, KTI1, PIP1, EF1A2, and MTH1, and a control terminator PIN2. Wild type RNA (wt) and no template (−) were used as negative controls. QC393, QC340, QC350, QC351, and QC352 were used as positive controls (+). The same YFP-3 primer was used as the sense primer. Three primers, 3UTR-3, SAMS-A1, SAMS-A2, progressively downstream of the terminator, were used as antisense primers for three RT-PCR assays (A, B, and C, respectively). The sizes of the expected RT-PCR bands are provided. A non-specific band was amplified from wild type RNA in the first RT-PCR (A).

Figure 8A:
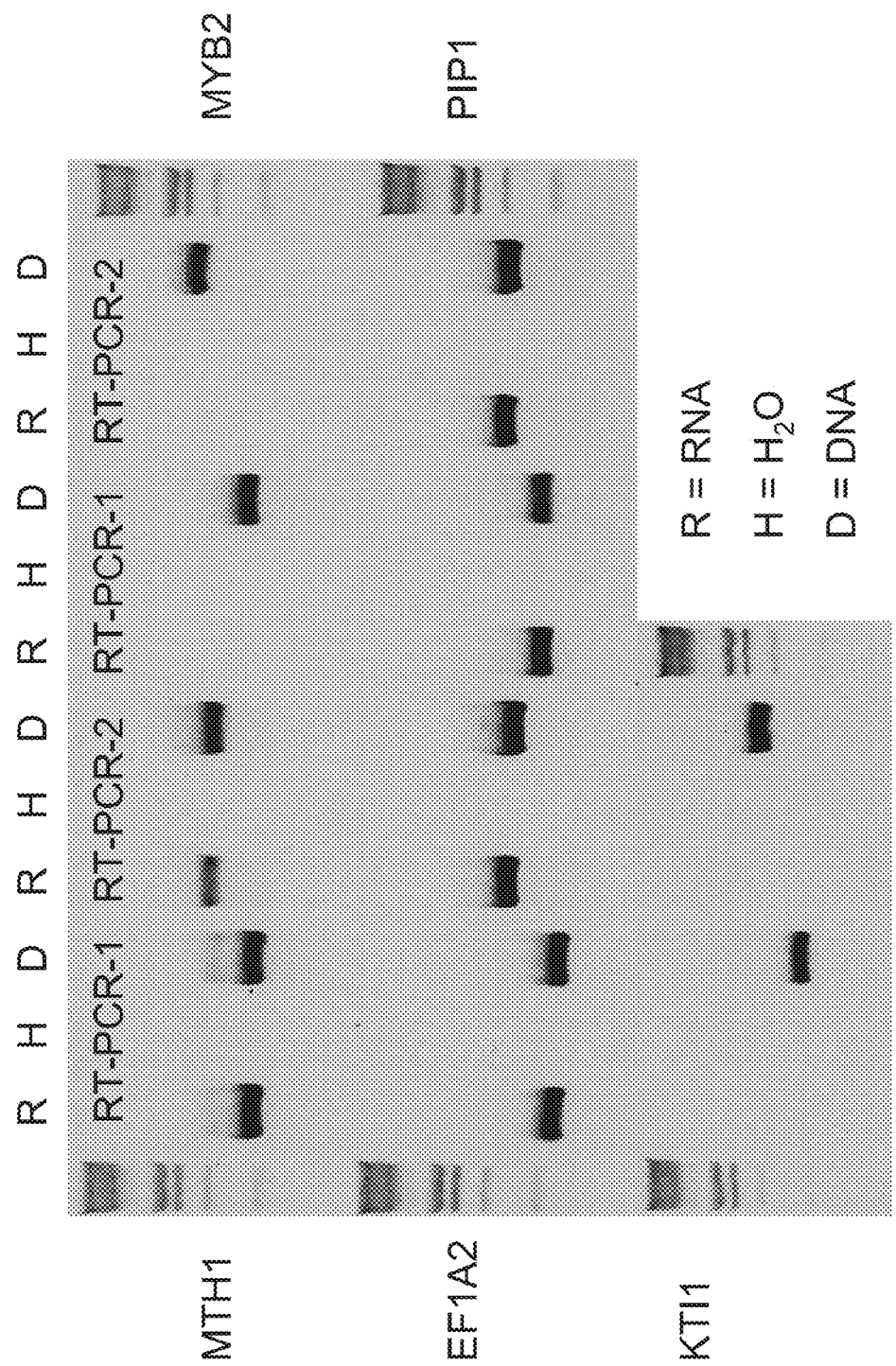
Figure 8B:
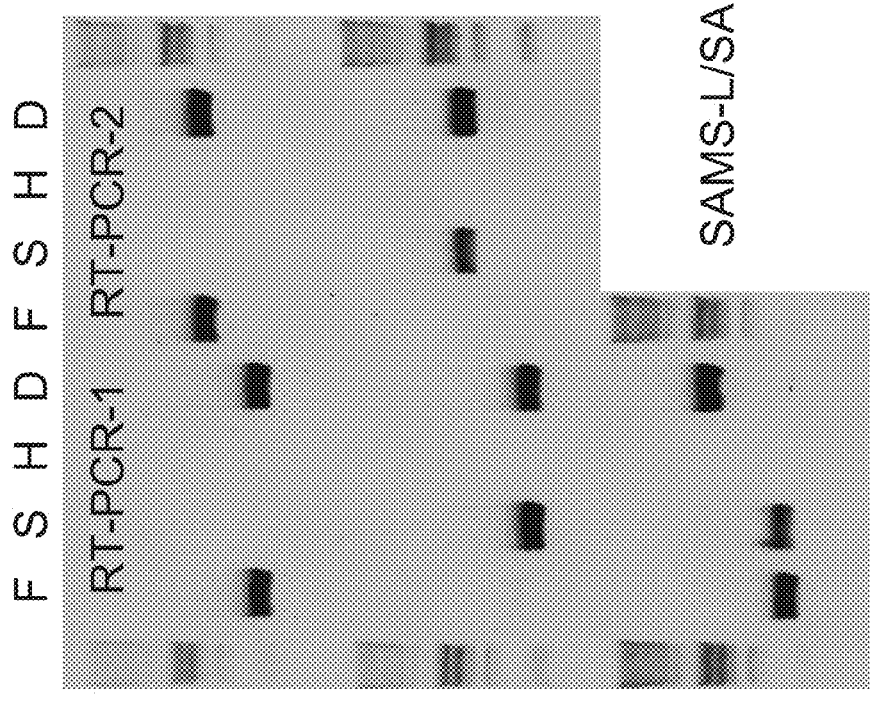

FIGS. 8A and 8B show the transcription termination check by RT-PCR of five endogenous genes from which the MYB2, KTI1, PIP1, EF1A2, and MTH1 terminators were cloned. Gene-specific primers used in the analysis are described in EXAMPLE 7. A) Two RT-PCR assays were performed on the following three templates: wild type plantlet RNA as the target, H$_2$O as the negative control, and genomic DNA as the positive control, with two sets of gene-specific primers for each terminator gene. RT-PCR-1 was specific to mRNA, while RT-PCR-2 was specific to RNA transcription read-through. Specific bands were detected with both RT-PCR assays for the three constitutive genes MTH1, EF1A2, and PIP1, but not for the flower-specific gene MYB2 or the seed-specific gene KTI1. B) Wild type flower and seed RNA were used in similar RT-PCR assays as the target templates to check the flower-specific gene MYB2 and the seed-specific gene KTI1. Specific bands were detected with both RT-PCR assays from flower RNA for the flower-specific gene MYB2 and from seed RNA for the seed-specific gene KTI1. The RT-PCR with the SAMS-L/SAMS-L2 primer set was done to check the flower RNA and seed RNA for genomic DNA contamination.

Figure 9:
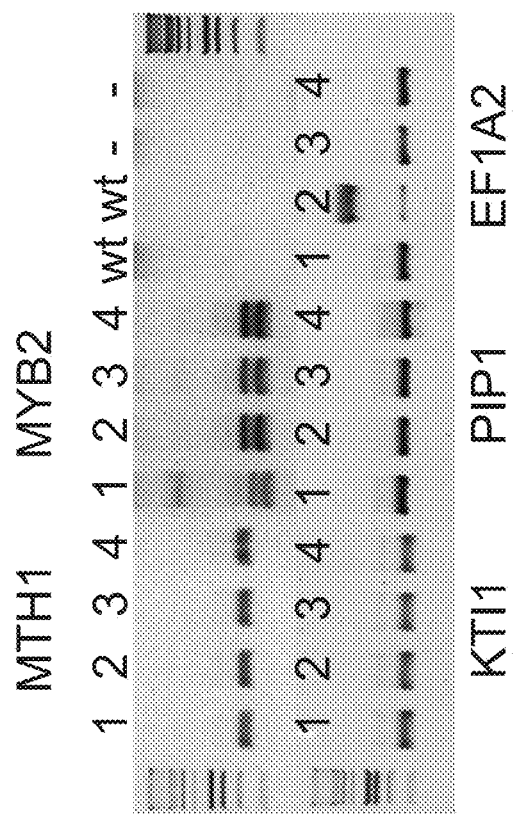

FIG. 9 shows the RT-PCR amplification of 3' UTR from transgenic plants having the MYB2, KTI1, PIP1, EF1A2, and MTH1 terminators. The first strand cDNA was first made with an oligo dT primer 3UTR-1 by reverse transcription. Then the YFP-3/3UTR-2 primer set was used to amplify the poly (A) containing 3UTR by PCR for subsequent cloning and sequencing. No specific band was amplified from the wild type (wt) and no template (−) negative controls.

Figure 10:
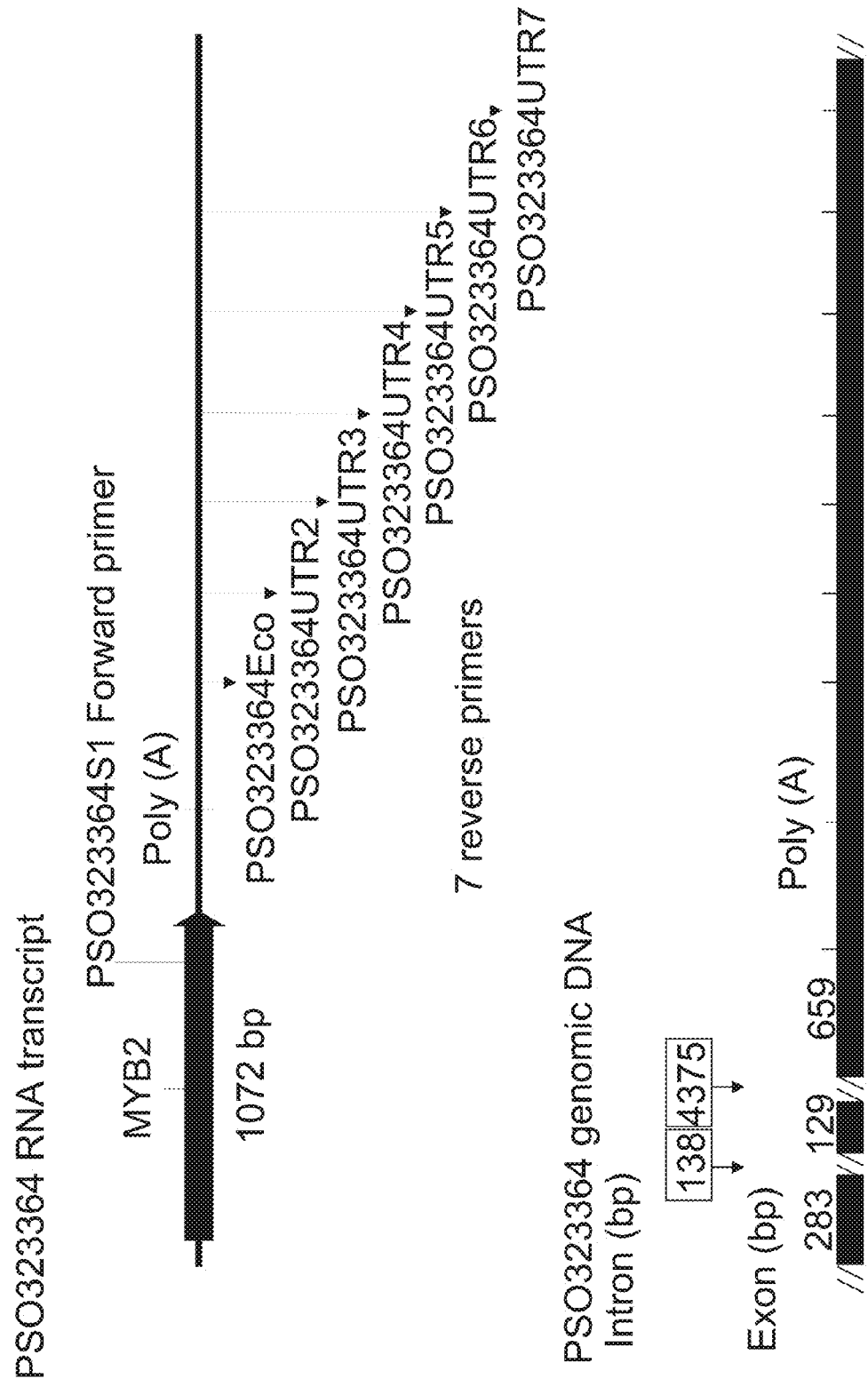

FIG. 10 shows the relative positions of the single forward primer PSO323364S1 (SEQ ID NO:77) and the seven reverse primers PSO323364Eco (SEQ ID NO:41), PSO0323364UTR2 (SEQ ID NO:94), PSO323364UTR3 (SEQ ID NO:95), PSO323364UTR4 (SEQ ID NO:96), PSO323364UTR5 (SEQ ID NO:97), PSO323364UTR6 (SEQ ID NO:98), and PSO0323364UTR7 (SEQ ID NO:99) specific to the RNA transcript and the genomic DNA of gene PSO0323364. These primers were designed to check if the observed transcription read through of endogenous genes would stop and at what point. Primers were designed similarly for each of the other four genes.

FIGS. 11A and 11B show the results of seven RT-PCR experiments for each of the five genes, PSO0323364 (MYB2), PSO400362 (KTI1), PSO332986 (PIP1), PSO0333268 (EF1A2), and PSO333209 (MTH1).

DETAILED DESCRIPTION OF THE INVENTION

The disclosure of all patents, patent applications, and publications cited herein are incorporated by reference in their entirety.

Definitions

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The term "invention" or "present invention" as used herein is not meant to be limiting to any one specific embodiment of the invention but applies generally to any and all embodiments of the invention as described in the claims and specification.

In the context of this disclosure, a number of terms and abbreviations are used. The following definitions are provided.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Polymerase chain reaction" is abbreviated PCR.

"Quantitative reverse transcription polymerase chain reaction" is abbreviated qRT-PCR.

"Reverse transcription polymerase chain reaction" is abbreviated RT-PCR.

As used herein, "GM-MYB2 terminator" or "MYB2 terminator" refer to the 3' untranslated sequence downstream of the coding region of the *Glycine max* PSO323364 gene, which encodes a putative polypeptide with significant homology to MYB transcription factors (Uimari and Strommer, *Plant J.* 12 (6), 1273-1284 (1997)). "GM-KTI1 terminator" or "KTI1 terminator" refer to the 3' untranslated sequence downstream of the coding region of the *Glycine max* PSO0400362 gene, which encodes a putative polypeptide with significant homology to Kunitz trypsin inhibitors (Jofuko and Goldberg, *Plant Cell* 1 (11), 1079-1093 (1989)). A "GM-PIP1 terminator" or "PIP1 terminator" refer to the 3' untranslated sequence downstream of the coding region of the *Glycine max* PSO0332986 gene, which encodes a putative polypeptide with significant homology to plasma membrane intrinsic proteins (Uehlein et al., *Phytochemistry* 68 (1), 122-129 (2007)). A "GM-EF1A2 terminator" or "EF1A2 terminator" refer to the 3' untranslated sequence downstream of the coding region of the *Glycine max* PSO0333268 gene, which encodes a putative polypeptide with significant homology to translation elongation factor EF-1α genes identified in various species, including soybean (Aguilar et al., *Plant Mol. Biol.* 17 (3), 351-360 (1991)). A "GM-MTH1 terminator" or "MTH1 terminator" refer to the 3' untranslated sequence downstream of the coding region of the *Glycine max* PSO333209 gene, which encodes a putative polypeptide with significant homology to metallothionein-like proteins (Munoz et al., *Physiol. Plantarum* 104, 273-279 (1998)).

The terminator nucleotide sequences are useful in combinations with different promoters in regulating the expression of any heterologous nucleotide sequence in a host plant in order to alter the phenotype of a plant.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

A "marketable trait", also referred to herein as a "marketable plant trait" or "commercial trait" or "commercially desirable trait", is any trait of importance to the commercial markets and interests of those involved in the development of the crop, wherein the marketable trait is evaluated in a fertile, mature plant. A marketable or commercial trait can include, without limitation, disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

Genes of interest are reflective of the commercial markets and interests of those involved in the development of the crop. Crops and markets of interest change, and as developing nations open up world markets, new crops and technologies will emerge. In addition, as our understanding of agronomic characteristics and traits, such as yield and heterosis, increases, the choice of genes for transformation will change accordingly. General categories of genes of interest include, but are not limited to, those genes involved in information, such as zinc fingers; those involved in communication, such as kinases; and those involved in housekeeping, such as heat shock proteins. More specific categories of transgenes, for example, include, but are not limited to, genes involved in important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits involve genes and proteins conferring cold, heat, salt, or drought resistance.

Disease and/or insect resistance genes may confer resistance to pests that significantly decrease yield, such as for example, anthracnose; soybean mosaic virus; soybean cyst nematode; root-knot nematode; the fungal agents that cause brown leaf spot, Downy mildew, purple seed stain, seed decay, and seedling diseases; and the bacterium *Pseudomonas syringae* pv. Glycinea that causes bacterial blight. Genes involved in insect resistance include, for example, *Bacillus thuringiensis* toxic protein genes (U.S. Pat. Nos. 5,366,892; 5,747,450; 5,723,756; 5,593,881; and Geiser et al., *Gene* 48:109 (1986)); lectins (Van Damme et al., *Plant Mol. Biol.* 24:825 (1994)); and the like.

Herbicide resistance traits may include genes conferring resistance to herbicides that act to inhibit the action of acetolactate synthase (ALS), in particular the sulfonylurea-type herbicides. The S4 and/or HRA mutations in the acetolactate synthase ALS gene, for example, confer resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al., *Science* 304, 1151-1154 (2004)).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene, the latter of which is more widely used. The nptII gene was initially isolated from the transposon Tn5 present in the bacterium strain *Escherichia coli* K12 (Beck et al., *Gene* 19, 327-36 (1982)). The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin, and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis, or polyacrylamide gel electrophoresis. Plants such as maize, cotton, tobacco, *Arabidopsis*, flax, soybean, and many others have been successfully transformed with the nptII gene.

The hygromycin phosphotransferase (denoted hpt, hph, or aphIV) gene was originally derived from *Escherichia coli* (Gritz et al., *Gene* 25, 179-188 (1983)). The gene codes for hygromycin phosphotransferase (HPT), which detoxifies the aminocyclitol antibiotic hygromycin B. A large number of plants have been transformed with the hpt gene, and hygromycin B has proved very effective in the selection of a wide range of plants, including monocots. Most plants, e.g. cereals, exhibit higher sensitivity to hygromycin B than to kanamycin. Likewise, the hpt gene is used widely in selection of transformed mammalian cells. The sequence of the hpt gene has been modified for use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al., *Plant Physiol.* 131: 167-176 (2003)).

Calcium-dependent protein kinases (CDPK), a family of serine-threonine kinases found primarily in the plant kingdom, are likely to function as sensor molecules in calcium-mediated signaling pathways. Calcium ions are important secondary messengers during plant growth and development (Harper et al., *Science* 252, 951-954 (1993); Roberts et al., *Curr Opin Cell Biol* 5, 242-246 (1993); Roberts et al., *Annu Rev Plant Mol Biol* 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al., *BMC Bioinformatics* 6:169 (2005)).

The quality of seeds and grains is reflected in traits such as levels and types of fatty acids or oils (saturated and unsaturated), quality and quantity of essential amino acids, and levels of carbohydrates. Therefore, commercial traits involving a gene or genes that increase the amino acids methionine and cysteine, two sulfur containing amino acids present in low amounts in soybeans, are of interest. Cystathionine gamma synthase (CGS) and serine acetyl transferase (SAT) are enzymes involved in the synthesis of methionine and cysteine, respectively.

Other commercial traits can involve genes that increase, for example, monounsaturated fatty acids, such as oleic acid, in oil seeds. Soybean oil contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2), and high oleic soybean oil can then be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.), and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species. Thus, downregulation of the expression of the enzymes involved in raffinose saccharide synthesis, such as galactinol synthase, for example, would be a desirable trait.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

The term "expression", as used herein, refers to the production of a functional end-product e.g., an mRNA or a protein (precursor or mature). "Altering expression" refers to the production of gene product(s) in transgenic organisms in amounts or proportions that differ significantly from the amount of the gene product(s) produced by the corresponding wild-type organisms (i.e., expression is increased or decreased).

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., *Plant J.* 16:651-659 (1998); and Gura, *Nature* 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Current data has suggested that dsRNA mediated mRNA cleavage may have been the conserved mechanism underlying these gene silencing phenomena (Elmayan et al., *Plant Cell* 10:1747-1757 (1998); Galun, *In Vitro Cell. Dev. Biol. Plant* 41(2): 113-123 (2005); Pickford et al., *Cell. Mol. Life Sci.* 60(5): 871-882 (2003)).

The terms "fragment (or variant) that is functionally equivalent" and "functionally equivalent fragment (or variant)" are used interchangeably herein. These terms refer to a portion or subsequence or variant of the terminator sequence of the present invention in which the ability to terminate transcription is retained. Fragments and variants can be obtained via methods such as site-directed mutagenesis and synthetic construction. Recombinant DNA constructs can be designed for use in co-suppression or antisense by linking a promoter, a heterologous nucleotide sequence, and a terminator fragment or variant thereof.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene", "recombinant DNA construct", or "recombinant expression construct", which are used interchangeably, refer to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A "heterologous nucleic acid fragment" or "heterologous nucleotide sequence" refers to a nucleotide sequence that is not naturally occurring with the plant terminator sequence of the invention. While this nucleotide sequence is heterologous to the terminator sequence, it may be homologous, or native, or heterologous, or foreign, to the plant host.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene. An exon is not necessarily a part of the sequence that encodes the final gene product.

An "isolated nucleic acid fragment" or "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA, or synthetic DNA.

The term "operably linked" refers to the association of nucleic acid sequences on a single polynucleotide so that the function of one is affected by the other. For example, a promoter is operably linked with a heterologous nucleotide sequence, e.g. a coding sequence, when it is capable of affecting the expression of that heterologous nucleotide sequence (i.e., the coding sequence is under the transcriptional control of the promoter). A coding sequence can be operably linked to regulatory sequences in sense or antisense orientation.

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell. "Expression cassette" refers to a fragment of DNA containing a foreign gene and having elements in addition to the foreign gene that allow for enhanced expression of that gene in a foreign host. "Transformation cassette" refers to a fragment of DNA containing a foreign gene and having elements in addition to the foreign gene that facilitate transformation of a particular host cell.

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, and the two primers complementary to the 3' boundaries of the target segment are annealed at low temperature and then extended at an intermediate temperature. One set of these three consecutive steps comprises a cycle.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Promoter" refers to a nucleotide sequence capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of some variation may have identical promoter activity.

The term "recombinant" refers to an artificial combination of two otherwise separated segments of sequence, e.g., by chemical synthesis or by the manipulation of isolated segments of nucleic acids by genetic engineering techniques.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

Standard recombinant DNA and molecular cloning techniques used herein are well known in the art and are described more fully in Sambrook, J. et al., In *Molecular Cloning: A Laboratory Manual*; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

"RNA transcript" refers to a product resulting from RNA polymerase-catalyzed transcription of a DNA sequence. When an RNA transcript is a perfect complementary copy of a DNA sequence, it is referred to as a primary transcript, or it may be an RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcript accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated yet has an effect on cellular processes.

A "substantially homologous sequence" refers to variants of the disclosed sequences such as those that result from site-directed mutagenesis, as well as synthetically derived sequences. A substantially homologous sequence of the present invention also refers to those fragments of a particular terminator nucleotide sequence disclosed herein that operate to terminate transcription of an operably linked heterologous nucleic acid fragment. These terminator fragments will comprise at least about 20 contiguous nucleotides, preferably at least about 50 contiguous nucleotides, more preferably at least about 75 contiguous nucleotides, even more preferably at least about 100 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present invention.

The terms "substantially similar" and "corresponding substantially" as used herein refer to nucleic acid fragments, particularly terminator sequences, wherein changes in one or more nucleotide bases do not substantially alter the ability of the terminator to terminate transcription. These terms also refer to modifications, including deletions and variants, of the nucleic acid sequences of the instant invention by way of deletion or insertion of one or more nucleotides that do not substantially alter the functional properties of the resulting terminator relative to the initial, unmodified terminator. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the terminator of the invention. Estimates of such homology are provided by either DNA-DNA or DNA-RNA hybridization under conditions of stringency as is well understood by those skilled in the art (Hames and Higgins, Eds.; In *Nucleic Acid Hybridisation*; IRL Press: Oxford, U. K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%, such as 81%, 82%, 83%, 84%, 85%, 86%, 87%, 88%, 89%, 90%, 91%, 92%, 93%, 94%, 95%, 96%, 97%, 98 and 99%.

Sequence alignments and percent similarity calculations may be determined using the Megalign program of the LASARGENE bioinformatics computing suite (DNASTAR Inc., Madison, Wis.) or using the AlignX program of the Vector NTI bioinformatics computing suite (Invitrogen, Carlsbad, Calif.). Multiple alignment of the sequences are performed using the Clustal method of alignment (Higgins and Sharp, *CABIOS* 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., *J. Mol. Biol.* 215:403-410 (1993)) and Gapped Blast (Altschul, S. F. et al., *Nucleic Acids Res.* 25:3389-3402 (1997)). The "BLASTN method of alignment" refers to a BLAST program that compares a nucleotide query sequence against a nucleotide sequence database.

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate, and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Transcription terminator", "3' non-coding sequences", "termination sequences", or "terminator" refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989).

"Transformation" refers to the transfer of a nucleic acid fragment into the genome of a host organism, resulting in genetically stable inheritance. Host organisms containing the transformed nucleic acid fragments are referred to as "transgenic" organisms. Thus, a "transgenic plant cell' as used herein refers to a plant cell containing the transformed nucleic acid fragments. The preferred method of soybean cell transformation is the use of particle-accelerated or "gene gun" transformation technology (Klein et al., *Nature* (London) 327:70-73 (1987); U.S. Pat. No. 4,945,050).

"Transient expression" refers to the temporary expression of a gene, often a reporter gene such as β-glucuronidase (GUS) or any of the fluorescent protein genes, GFP, ZS-YELLOW1 N1, AM-CYAN1, and DS-RED, in selected certain cell types of the host organism in which the transgenic gene is introduced temporally by a transformation method. The transformed material of the host organism is subsequently discarded after the transient gene expression assay.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability, or translation efficiency. Examples of translation leader sequences have been described (Turner, R. and Foster, G. D., *Molecular Biotechnology* 3:225 (1995)).

This invention concerns isolated terminators of a MYB family transcription factor (MYB2), a Kunitz trypsin inhibitor (KTI1), a plasma membrane intrinsic protein (PIP1), a translation elongation factor (EF-1A), and a metallothionein protein (MTH1).

This invention concerns an isolated polynucleotide comprising a terminator wherein said terminator comprises the nucleotide sequence set forth in SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128; a full-length complement of SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128; or a nucleotide sequence having at least 90% sequence identity, based on the BLASTN method of alignment, when compared to the sequence set forth in SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128.

A nucleic acid fragment that is functionally equivalent to an instant terminator is any nucleic acid fragment that is capable of terminating the transcription of a coding sequence or functional RNA in a similar manner as the terminator. Thus, the invention also includes a nucleotide sequence comprising a fragment of SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128; a full-length complement of a fragment of SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128; or a nucleotide sequence having at least 90% sequence identity, based on the BLASTN method of alignment, when compared to the fragment of SEQ ID NO:1, SEQ ID NO:2, SEQ ID NO:3, SEQ ID NO:4, SEQ ID NO:5, SEQ ID NO:124, SEQ ID NO:125, SEQ ID NO:126, SEQ ID NO:127, or SEQ ID NO:128, or a full-length complement thereof, wherein the nucleotide sequence functions as a terminator.

The terminator activity of each of the soybean genomic DNA fragments of SEQ ID NO:1, 2, 3, 4, and 5 was individually assessed by linking the fragment to a yellow fluorescence reporter gene, ZS-YELLOW1 N1 (YFP) which is controlled by a soybean ubiquitin gene promoter GM-UBQ (Matz et al., *Nat. Biotechnol.* 17:969-973 (1999)), transforming the UBQ:YFP:terminator expression cassette into soybean, and analyzing YFP expression in various cell types of the transgenic plants (see EXAMPLES 7 and 8). YFP expression was detected in all parts of the transgenic plants, though stronger expression was detected in fast growing tissues such as developing embryos and pods. These results indicated that the nucleic acid fragment functioned as a transcription terminator to add polyadenylation tails on the YFP gene transcripts and to terminate YFP gene transcription.

It is clear from the disclosure set forth herein that one of ordinary skill in the art could perform the following procedure:

1) operably linking the nucleic acid fragment containing a terminator sequence of the invention to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric promoter:reporter:terminator gene expression cassette into an appropriate plant for expression of the reporter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, and cocoa and the monocots, corn, wheat, rice, barley, and palm.

3) testing for expression of the promoter:reporter:terminator in various cell types of transgenic plant tissues, e.g., leaves, roots, flowers, seeds, transformed with the chimeric promoter:reporter:terminator gene expression cassette by assaying for expression of the reporter gene product.

In another aspect, this invention concerns a recombinant DNA construct comprising a promoter, at least one heterologous nucleic acid fragment, and any terminator, or combination of terminator elements, of the present invention, wherein the promoter, at least one heterologous nucleic acid fragment, and terminator(s) are operably linked. Recombinant DNA constructs can be constructed by operably linking the nucleic acid fragment of the invention, the terminator sequence set forth in SEQ ID NO:1, 2, 3, 4, 5, 124, 125, 126, 127, or 128 or a fragment that is substantially similar and functionally equivalent to any portion of the nucleotide sequence set forth in SEQ ID NO:1, 2, 3, 4, 5, 124, 125, 126, 127, or 128, to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select, and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., *Plant Cell Rep.* 15:653-657 (1996), McKently et al., *Plant Cell Rep.* 14:699-703 (1995)); *papaya* (Ling et al., *Bio/technology* 9:752-758 (1991)); and pea (Grant et al., *Plant Cell Rep.* 15:254-258 (1995)). For a review of other commonly used methods of plant transformation see Newell, C. A., *Mol. Biotechnol.* 16:53-65 (2000). One of these methods of transformation uses *Agrobacterium rhizogenes* (Tepfler, M. and Casse-Delbart, F., *Microbiol. Sci.* 4:24-28 (1987)). Transformation of soybeans using direct delivery of DNA has been published using PEG fusion (PCT Publication No. WO 92/17598), electroporation (Chowrira et al., *Mol. Biotechnol.* 3:17-23 (1995); Christou et al., *Proc. Natl. Acad. Sci. U.S.A.* 84:3962-3966 (1987)), microinjection, or particle bombardment (McCabe et al., *Bio/Technology* 6:923 (1988); Christou et al., *Plant Physiol.* 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In *Methods for Plant Molecular Biology*; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In *Molecular Cloning: A Laboratory Manual;* $2^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., *EMBO J.* 4:2411-2418 (1985); De Almeida et al., *Mol. Gen. Genetics* 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

Another general application of the terminators of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to a promoter of choice and a terminator of the present invention. (See U.S. Pat. No. 5,231,020, and PCT Publication No. WO 99/53050, PCT Publication No. WO 02/00904, and PCT Publication No. WO 98/36083, for methodology to block plant gene expression via cosuppression.) Alternatively, a chimeric gene designed to express antisense RNA for a heterologous nucleic acid fragment can be constructed by linking the fragment in reverse orientation to the terminator of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of expressing at least one heterologous nucleic acid fragment in a plant cell which comprises:
 (a) transforming a plant cell with the recombinant DNA construct described herein;
 (b) growing fertile mature plants from the transformed plant cell of step (a);
 (c) selecting plants containing a transformed plant cell wherein the heterologous nucleic acid fragment is expressed.

Transformation and selection can be accomplished using methods well-known to those skilled in the art including, but not limited to, the methods described herein.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

In the discussion below, parts and percentages are by weight, and degrees are Celsius, unless otherwise stated. Sequences of promoters, cDNA, adaptors, terminators, and primers listed in this invention are in the 5' to 3' orientation unless described otherwise. Techniques in molecular biology were typically performed as described in Ausubel, F. M. et al. (In *Current Protocols in Molecular Biology*; John Wiley and Sons: New York, (1990)) or Sambrook, J. et al. (In *Molecular Cloning: A Laboratory Manual;* $2^{nd}$ ed.; Cold Spring Harbor Laboratory Press: Cold Spring Harbor, N.Y., (1989)) (hereinafter "Sambrook et al., 1989").

Example 1

Identification of Terminator Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. For those EST sequences representing the same gene that are found more frequently in one tissue-specific cDNA library than in another, there is a possibility that the represented gene could be a tissue-preferred gene candidate. For example, EST sequences representing the same gene that are found more frequently in a flower library than in a leaf library may indicate a flower-preferred gene candidate. Alternatively, if similar numbers of ESTs for the same gene are found in various libraries constructed from different tissues, the represented gene could be a constitutively expressed gene. Multiple EST sequences representing the same soybean gene were compiled electronically, based on their overlapping sequence homology, into a full length sequence representing that unique gene. The assembled unique gene sequences were collected, and the information was stored in searchable databases.

To identify strong constitutively expressed genes, database searches were performed to detect gene sequences found at similar frequencies across multiple tissue-specific libraries, such as leaf, root, flower, embryos, pod, etc. To identify tissue-specific genes, e.g. seed-specific genes, searches were performed to look for gene sequences found at high frequency in one tissue-specific library, such as a seed-specific library, and at little to no frequency in other tissue-specific libraries. Several constitutive and tissue-specific genes were identified as candidates for the cloning of novel promoters and/or terminators.

A more sensitive gene expression profiling methodology MPSS (Mass Parallel Signature Sequence) transcript profiling technique (Brenner et al., *Proc. Natl. Acad. Sci. USA* 97:1665-70 (2000)) was used to confirm the gene expression profiles of the candidate genes. The MPSS technology involves the generation of 17 base signature tags from mRNA samples that have been reverse transcribed from poly A+ RNA isolated using standard molecular biology techniques (Sambrook et al., 1989). The tags are simultaneously sequenced and assigned to genes or ESTs. The abundance of these tags is given a number value that is normalized to parts per million (PPM), which then allows the tag expression, or tag abundance, to be compared across different tissues. Thus, the MPSS platform can be used to determine the expression pattern of a particular gene and its expression levels in different tissues.

MPSS gene expression profiles were generated from different soybean tissues over time, and the profiles were accumulated in a searchable database. Each candidate gene sequence was first used to search the MPSS database to identify an MPSS tag that was identical to a 17 base pair region in the 3' end of the corresponding cDNA sequence. The tag sequence was then used to search the MPSS database again to reveal its abundance in different tissues. As illustrated in Table 1, the PSO323364 gene was confirmed to be flower-specific; the PSO400362 gene was confirmed to be seed-specific; and PSO332986 and PSO333268 were confirmed to be constitutively expressed. No sequence-specific tag was identified for PSO333209.

TABLE 1

Abundances of four gene-specific MPSS tags in soybean tissues

| Gene ID | | | |
|---|---|---|---|
| PSO323364 | PSO400362 | PSO332986 | PSO333268 |
| SEQ ID NO: | | | |
| 16 | 17 | 18 | 19 |

| | | | | |
|---|---|---|---|---|
| Anther | 0 | 0 | 200 | 2245 |
| Flower | 1720 | 0 | 3325 | 2715 |
| Leaf | 0 | 0 | 2105 | 4810 |
| Pod | 0 | 0 | 3327 | 5848 |
| Root | 0 | 0 | 6046 | 4422 |
| Seed | 0 | 82124 | 4338 | 7171 |
| Stem | 0 | 0 | 3827 | 3275 |

The MPSS profiles of the candidate genes were confirmed and extended by analyzing 14 different soybean tissues using the relative quantitative RT-PCR (qRT-PCR) technique with an AB17500 real time PCR system (Applied Biosystems, Foster City, Calif.).

Fourteen soybean tissues (somatic embryo, somatic embryo grown one week on charcoal plate, leaf, leaf petiole, root, flower bud, open flower, R3 pod, R4 seed, R4 pod coat, R5 seed, R5 pod coat, R6 seed, R6 pod coat) were collected from cultivar 'Jack' and flash frozen in liquid nitrogen. The seed and pod development stages were defined according to descriptions in Fehr and Caviness, *IWSRBC* 80:1-12 (1977). Total RNA was extracted with Trizol reagents (Invitrogen, Carlsbad, Calif.) and treated with DNase I to remove any trace amount of genomic DNA contamination. The first strand cDNA was synthesized using the Superscript III reverse transcriptase (Invitrogen).

PCR analysis was performed to confirm that the cDNA was free of genomic DNA, using primers SAMS-L and SAMS-L2 (SEQ ID NO:53 and SEQ ID NO:54, respectively). The primers are specific to the 5'UTR intron/exon junction region of a soybean S-adenosylmethionine synthetase gene promoter SAMS (PCT Publication No. WO00/37662). PCR using this primer set amplifies a 967 bp DNA fragment from soybean genomic DNA template and a 376 bp DNA fragment from the cDNA template.

The cDNA aliquots were used in the quantitative RT-PCR analysis, using the Power Sybr® Green real time PCR master mix (Applied Biosystems). An endogenous soybean ATP sulfurylase gene was used as an internal control, and wild type soybean genomic DNA was used as the calibrator for relative quantification. The data was captured and analyzed using the sequence detection software provided with the AB17500 real time PCR system. The gene-specific primers used for the endogenous control ATPS gene were ATPS-87F and ATPS-161R (SEQ ID NO:20 and SEQ ID NO:21, respectively). The primers used for the five other target genes were: PSO323364F and PSO323364R (SEQ ID NO:22 and SEQ ID NO:23, respectively) for PSO323364, PSO400362F and PSO400362R (SEQ ID NO:24 and SEQ ID NO:25, respectively) for PSO400362, PSO332986F and PSO332986R (SEQ ID NO:26 and SEQ ID NO:27, respectively) for PSO332986, PSO333268F and PSO333268R (SEQ ID NO:28 and SEQ ID NO:29, respectively) for PSO333268, and PSO333209F and PSO333209R (SEQ ID NO:30 and SEQ ID NO:31, respectively) for PSO333209. For each of the five genes, the qRT-PCR profile, as illustrated in FIG. 1, was consistent with its respective MPSS expression profile.

The putatively translated polypeptide sequences of the five candidate genes were used to search the databases of the National Center for Biotechnology Information (http://www.ncbi.nlm.nih.gov/) to identify homologous sequences. The putative polypeptide encoded by the PSO323364 gene (the nucleotide and amino acid sequences are set forth in SEQ ID NO:6 and SEQ ID NO:11, respectively) has significant homology to MYB transcription factors (Uimari and Strommer, *Plant J.* 12:1273-1284 (1997)) and is referred to herein as MYB2. The putative polypeptide encoded by the PSO400362 gene (the nucleotide and amino acid sequences of which are set forth in SEQ ID NO:7 and SEQ ID NO:12, respectively) has significant homology to Kunitz trypsin inhibitors (Jofuko and Goldberg, *Plant Cell* 1:1079-1093 (1989)) and is referred to herein as KTI1. The putative polypeptide encoded by the PSO332986 gene (the nucleotide and amino acid sequences of which are set forth in SEQ ID NO:8 and SEQ ID NO:13, respectively) has significant homology to plasma membrane intrinsic proteins (Uehlein et al., *Phytochemistry* 68:122-129 (2007)) and is referred to herein as PIP1. The putative polypeptide encoded by the PSO333268 gene (the nucleotide and amino acid sequences of which are set forth in SEQ ID NO:9 and SEQ ID NO:14, respectively) has significant homology to translation elongation factor EF-1α genes (Aguilar et al., *Plant Mol. Biol.* 17:351-360 (1991)) and is referred to herein as EF1A2. The putative polypeptide encoded by the PSO333209 gene (the nucleotide and amino acid sequences of which are set forth in SEQ ID NO:10 and SEQ ID NO:15, respectively) has significant homology to metallothionein-like proteins (Munoz et al., *Physiol. Plantarum* 104:273-279 (1998)) and is referred to herein as MTH1.

Example 2

Cloning of Novel Terminators

Soybean BAC (bacterial artificial chromosome) clones that contain the selected genes were identified by PCR analysis. PSO323364 was found on BAC clone SBH145N17; PSO400362 was found on BAC clone SBH136J24; PSO332986 was found on BAC clone SBH172F4; PSO333268 was found on BAC clone SBH123F11; and PSO333209 was found on BAC clone SBH85K11. Approximately 1 kb of 3' end sequence for each of the selected cDNAs was sequenced from each respective BAC clone, in order to amplify terminator sequences via PCR. For each PCR, a SacI site (GAGCTC) was introduced by the 5' end sense primer and an EcoRI site (GAATTC) was introduced by the 3' antisense primer. Hence, primers PSO323364Sac and PSO323364Eco (SEQ ID NO:40 and SEQ ID NO:41, respectively) were used to amplify the MYB2 terminator; primers PSO400362Sac and PSO400362Eco (SEQ ID NO:42 and SEQ ID NO:43, respectively) were used to amplify the KTI1 terminator; primers PSO332986Sac and PSO332986Eco (SEQ ID NO:44 and SEQ ID NO:45, respectively) were used to amplify the PIP1 terminator; primers PSO333268Sac and PSO333268Eco (SEQ ID NO:46 and SEQ ID NO:47, respectively) were used to amplify the EF1A2 terminator; and primers PSO333209Sac and PSO333209Eco (SEQ ID NO:48 and SEQ ID NO:49, respectively) were used to amplify the MTH1 terminator. PCR cycle conditions were 94° C. for 4 minutes; 35 cycles of 94° C. for 30 seconds, 60° C. for 1 minute, and 68° C. for 1 minute; and a final 68° C. for 5 minutes before holding at 4° C. using the Platinum high fidelity Taq DNA polymerase (Invitrogen). PCR reactions were resolved using agarose gel electrophoresis to identify DNA bands representing the ~0.5 Kb terminators.

Figure 2A:
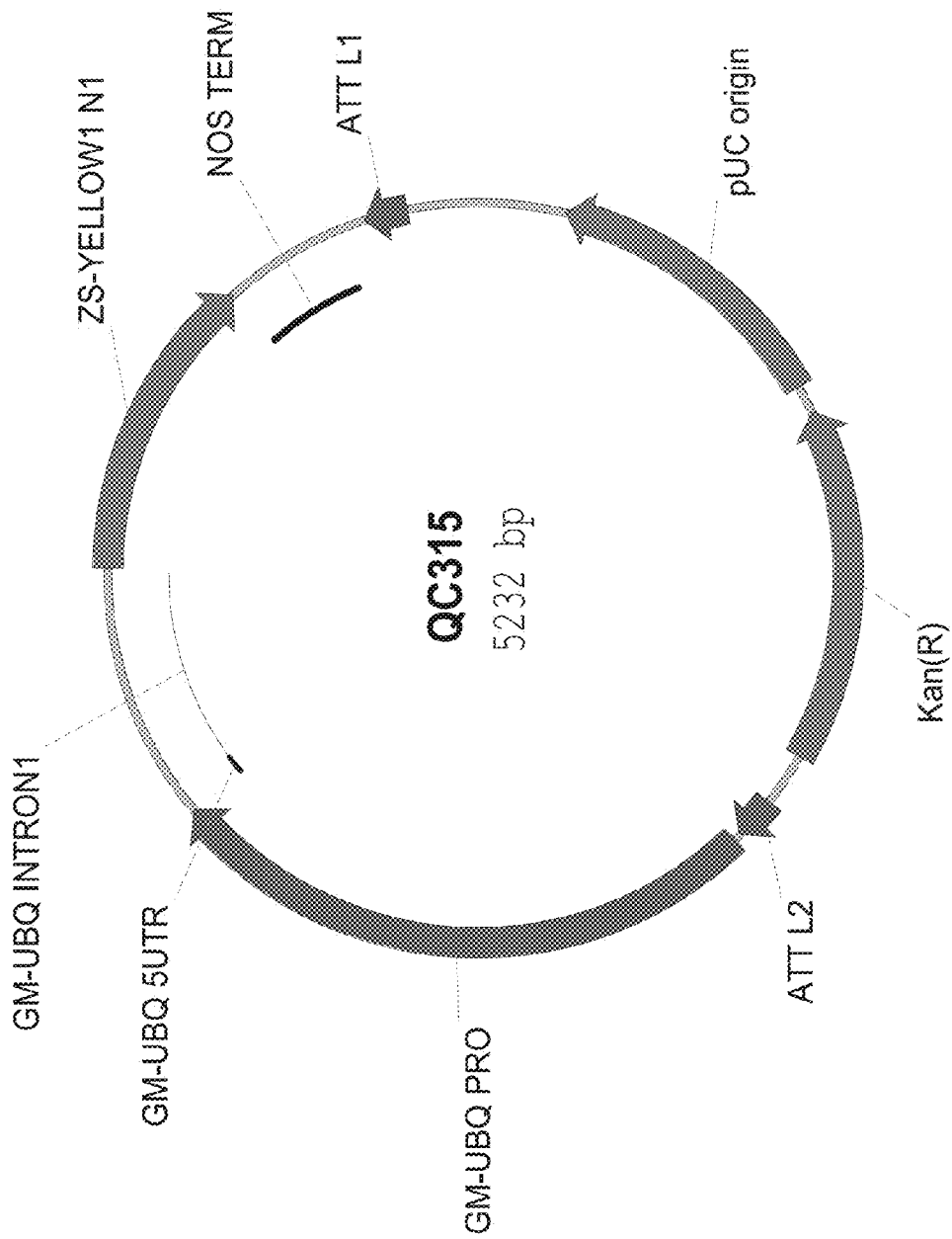
Figure 2B:
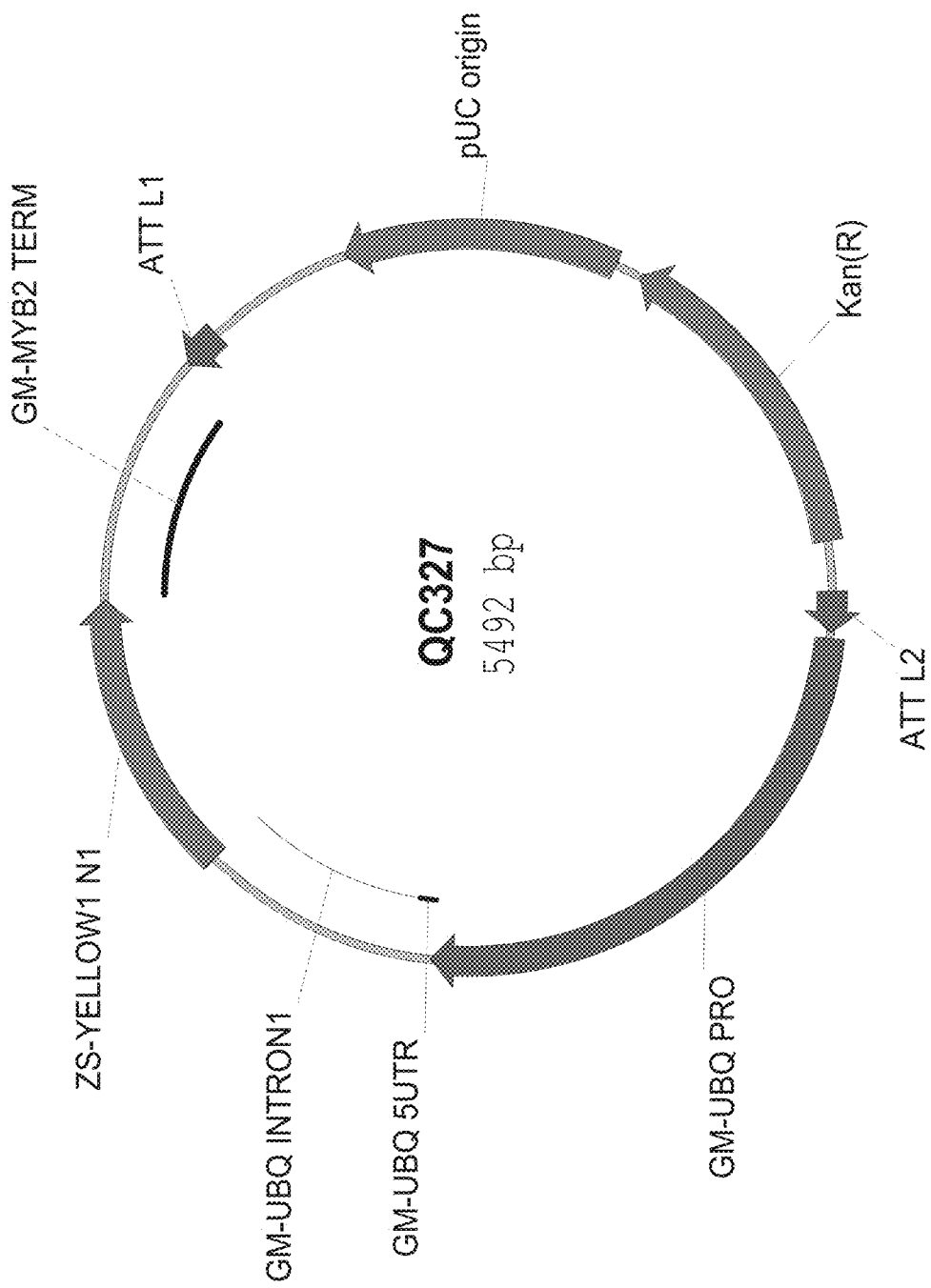
Figure 2C:
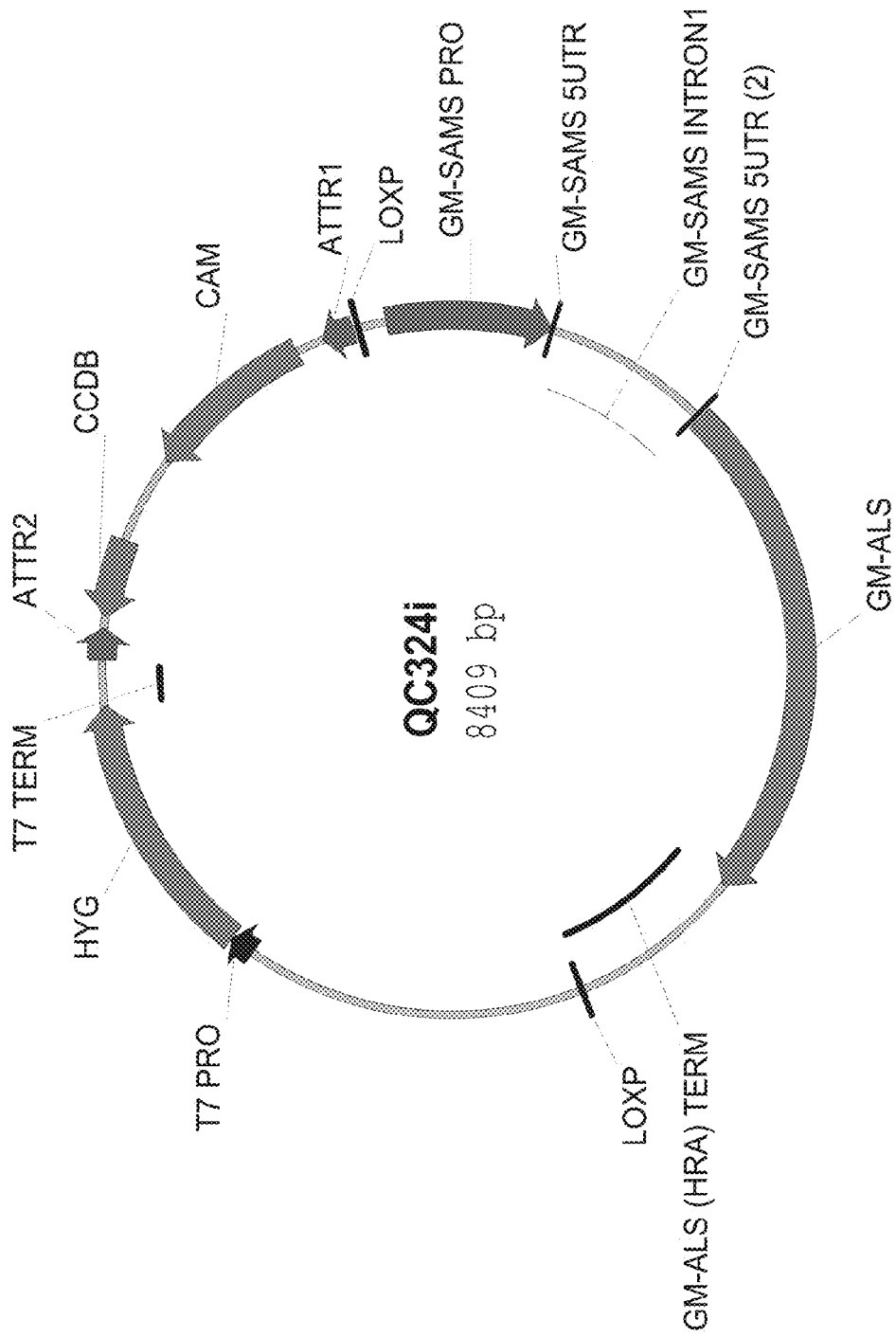
Figure 2D:
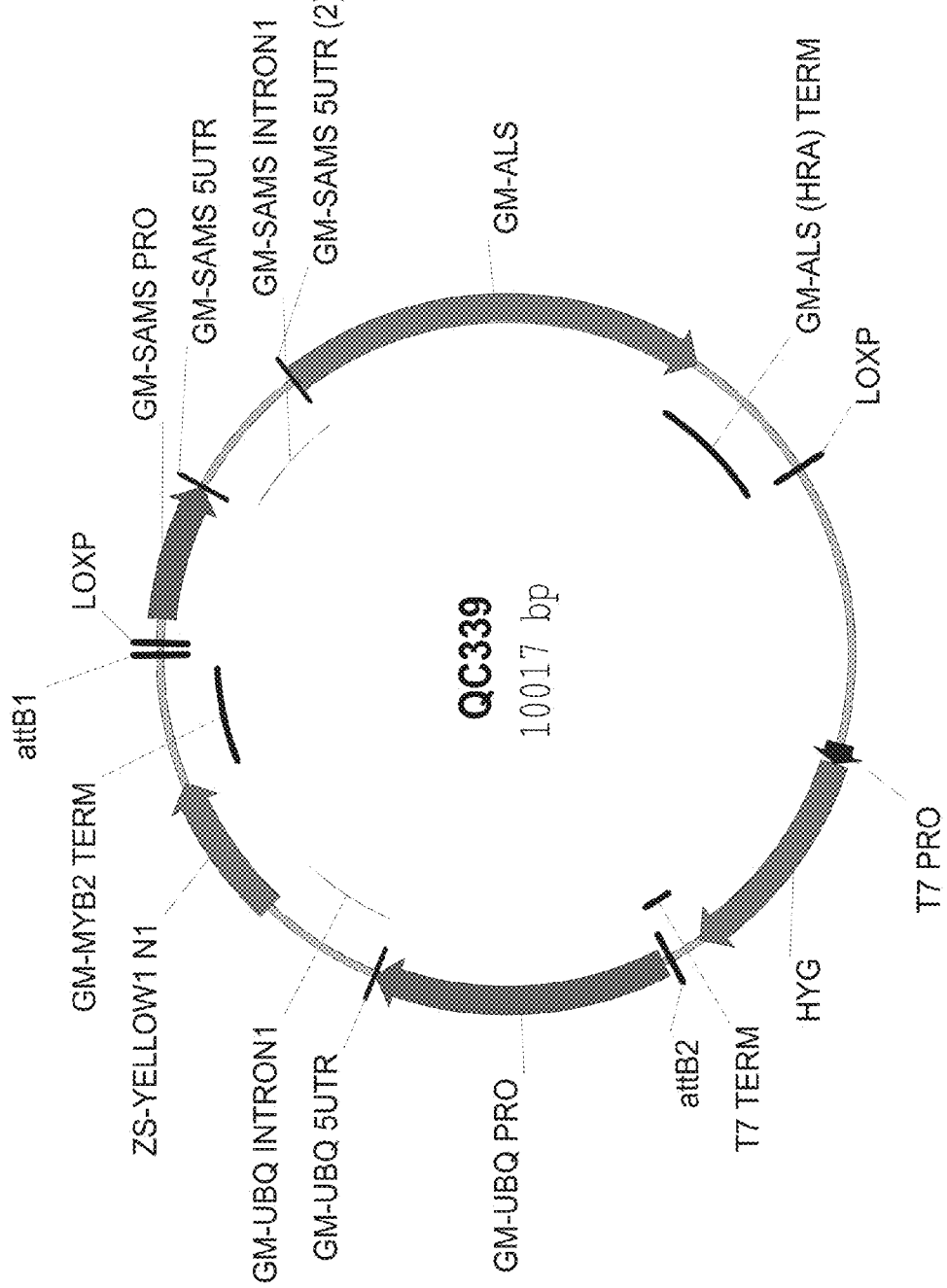
Figure 3A:
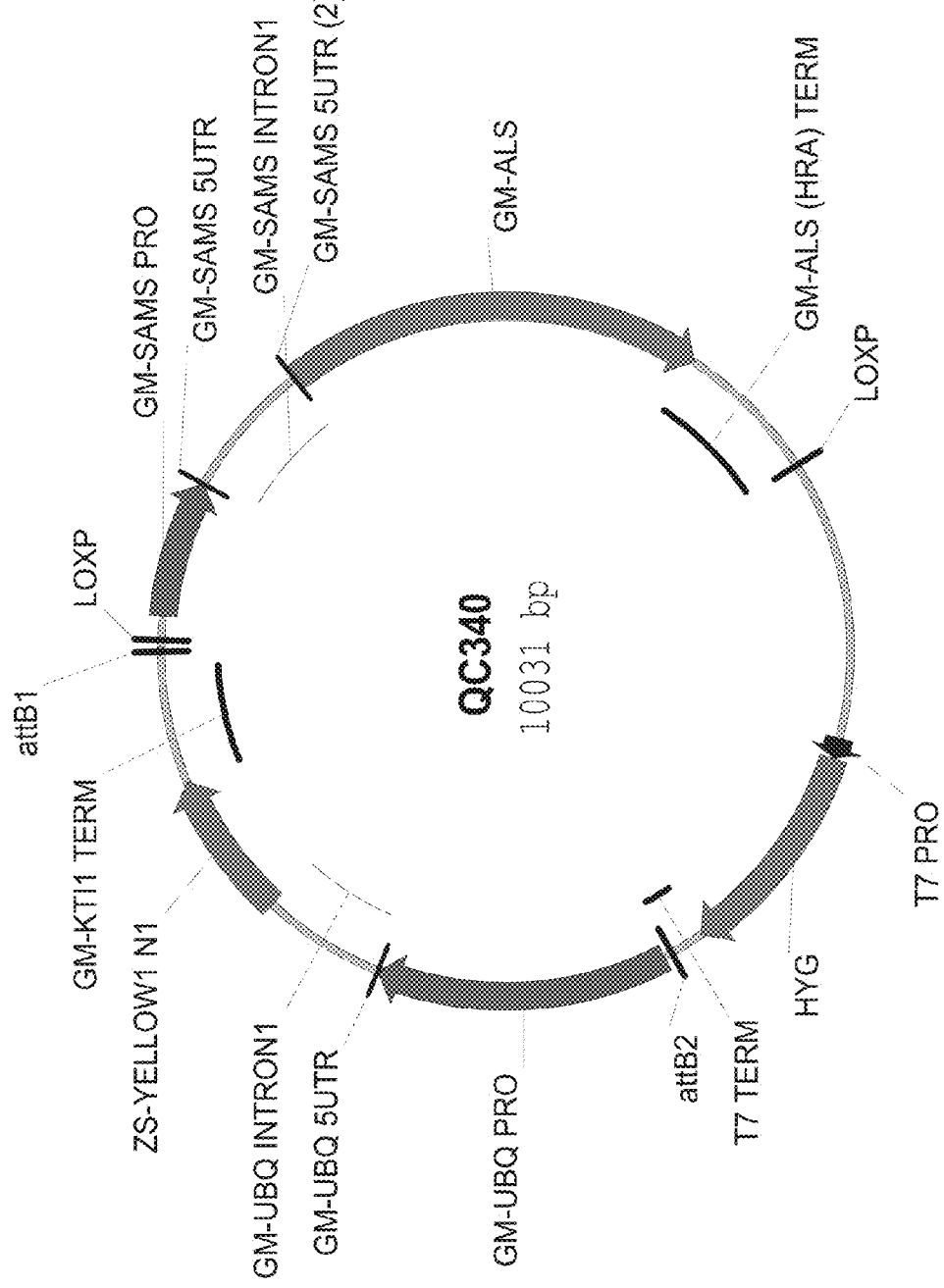
Figure 3C:
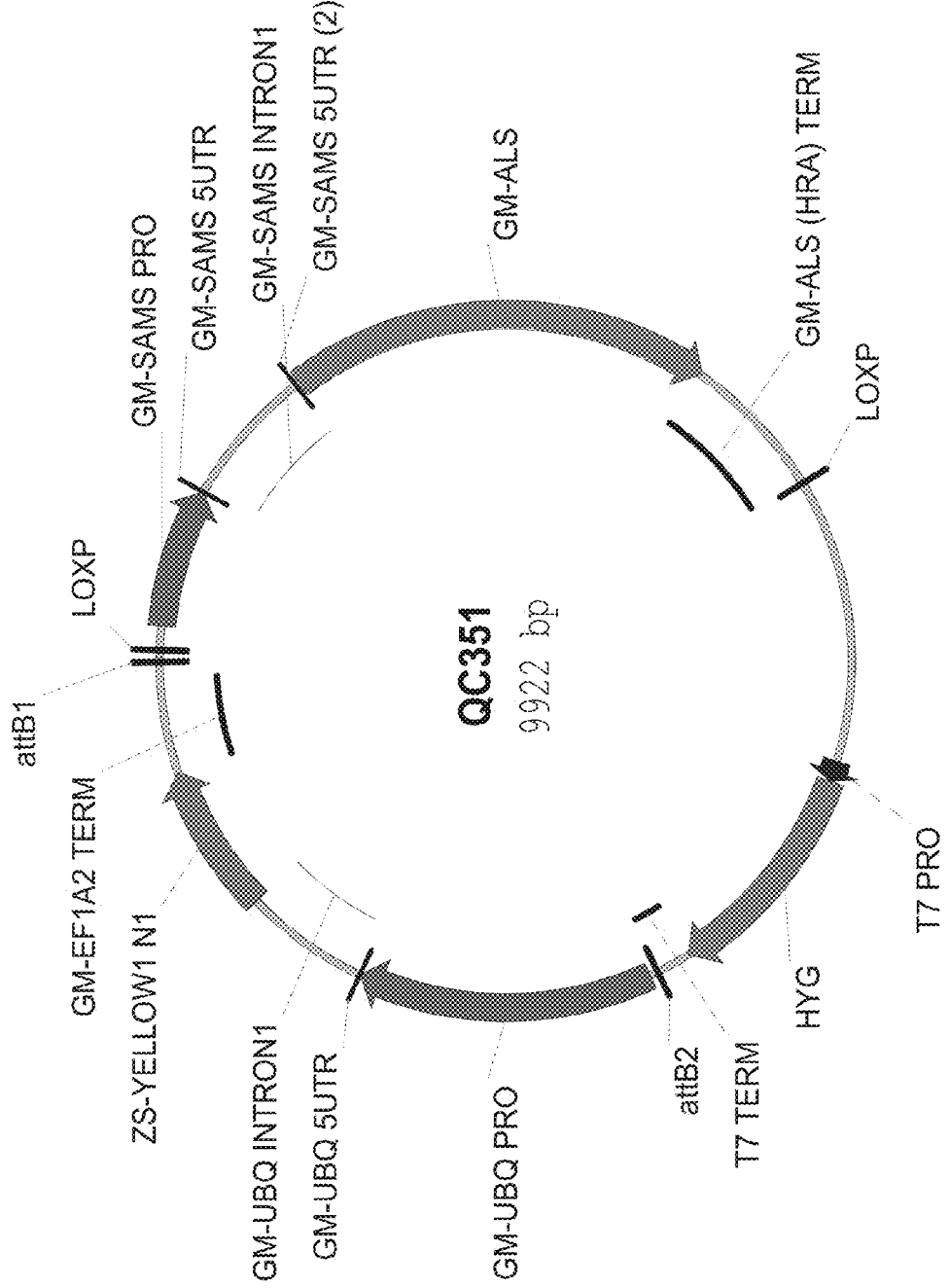
Figure 3D:
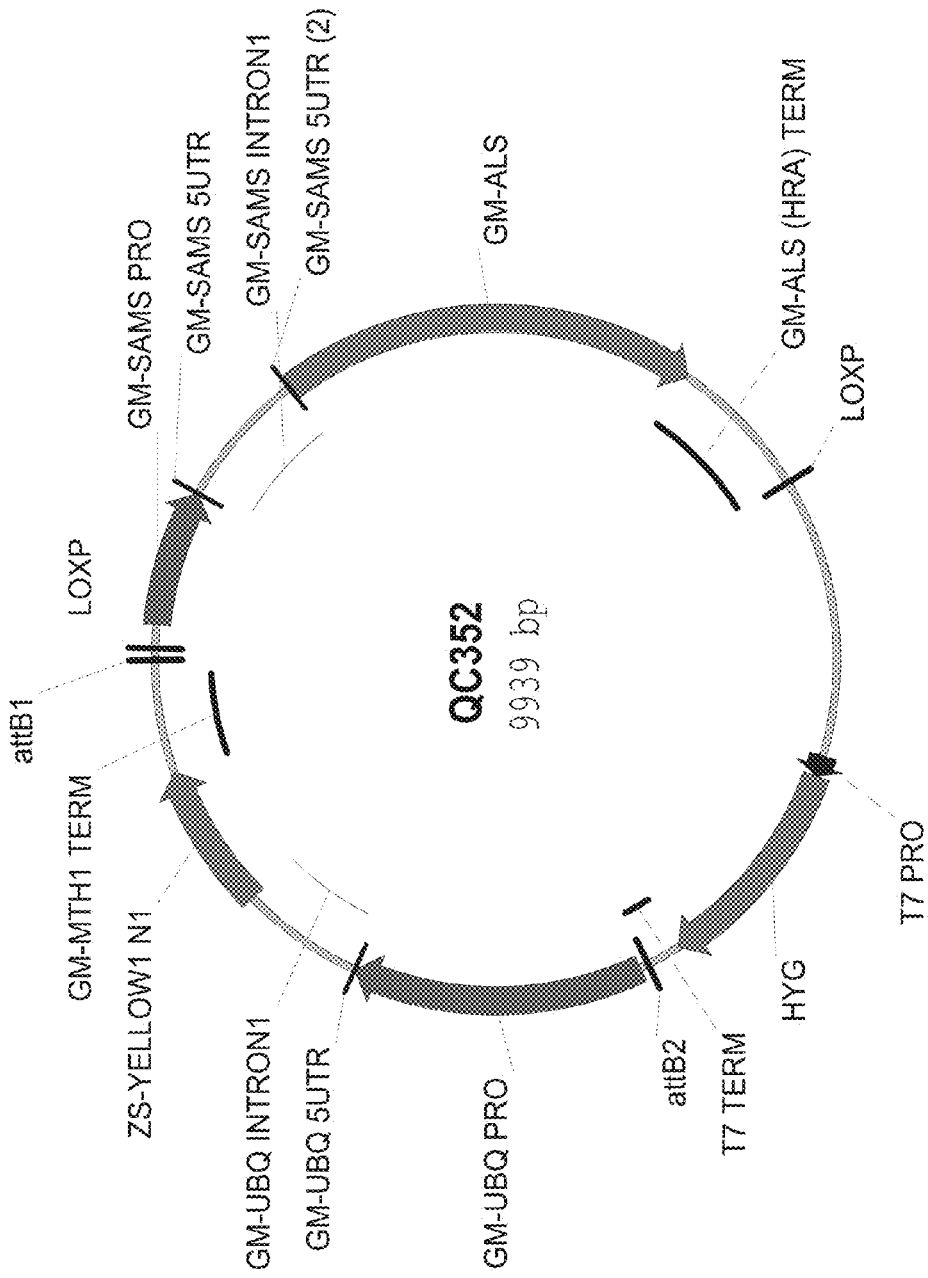

Each PCR amplified a terminator DNA fragment. The MYB2 terminator fragment was digested with SacI and EcoRI and then ligated to the corresponding SacI and EcoRI sites of Gateway entry vector QC315 (FIG. 2A and SEQ ID NO:32), to create an intermediate construct QC327 (FIG. 2B and SEQ ID NO:33). Several clones of QC327 were sequenced, and the clone with the correct MYB2 terminator sequence (SEQ ID NO:1) was selected. In construct QC327, the MYB2 terminator was placed downstream of the fluorescent reporter gene ZS-YELLOW N1 (YFP), which was under the control of a soybean ubiquitin promoter GM-UBQ. The YFP expression cassette was then linked to a soybean transformation selectable marker gene cassette SAMS:HRA in construct QC324i (FIG. 2C and SEQ ID NO:34) by LR clonase-mediated DNA recombination between the attL1 and attL2 recombination sites (SEQ ID NO:87 and SEQ ID NO:88, respectively) in QC327 and the attR1 and attR2 recombination sites (SEQ ID NO:89 and SEQ ID NO:90, respectively) in QC324i (Invitrogen), to create the final transformation ready construct QC339 (FIG. 2D and SEQ ID NO:35). Two 21 bp recombination sites attB1 and attB2 (SEQ ID NO:91 and SEQ ID NO:92, respectively) were created, resulting from DNA recombination between attL1 and attR2 and from DNA recombination between attL2 and attR2, respectively. Similarly, the other four terminators, KTI1 (SEQ ID NO:2), PIP1 (SEQ ID NO:3), EF1A2 (SEQ ID NO:4), and MTH1 (SEQ ID NO:5), were cloned into the final transformation ready constructs, QC340, QC350, QC351, and QC352, respectively (FIG. 3A, 3B, 3C, 3D). Complete sequences of constructs QC339, QC340, QC350, QC351, and QC352 are listed as SEQ ID NO:35, SEQ ID NO:36, SEQ ID NO:37, SEQ ID NO:38, and SEQ ID NO:39, respectively.

Example 3

Transformation of Soybean with the Terminator Constructs

Each of the terminator constructs, QC339, QC340, QC350, QC351, and QC352, contained a DNA fragment that included the respective UBQ:YFP:terminator cassette linked to a SAMS:HRA expression cassette. For each construct, the DNA fragment was isolated by digestion with AscI, separated from the vector backbone by agarose gel electrophoresis, and gel-purified using a DNA gel extraction kit (Qiagen, Valencia, Calif.). Each of the purified DNA fragments was transformed into the soybean cultivar "Jack" by particle gun bombardment (Klein et al., Nature 327:70-73 (1987); U.S. Pat. No. 4,945,050), as described in detail below, to study the functions of each terminator in stably transformed soybean plants.

The same methodology as outlined above for the UBQ:YFP:terminator-SAMS:HRA expression cassette construction and transformation can be used with other heterologous nucleic acid sequences encoding for example a reporter protein, a selection marker, a protein conferring disease resistance, a protein conferring herbicide resistance, a protein conferring insect resistance, a protein involved in carbohydrate metabolism, a protein involved in fatty acid metabolism, a protein involved in amino acid metabolism, a protein involved in plant development, a protein involved in plant growth regulation, a protein involved in yield improvement, a protein involved in drought resistance, a protein involved in cold resistance, a protein involved in heat resistance, and a protein involved in salt resistance, all in plants.

Soybean somatic embryos from the Jack cultivar were induced as follows. Cotyledons (~3 mm in length) were dissected from surface sterilized, immature seeds and were cultured for 6-10 weeks in the light at 26° C. on Murashige and Skoog (MS) media containing 0.7% agar and supplemented with 10 mg/ml 2,4-D. Globular stage somatic embryos, which produced secondary embryos, were excised, placed into flasks containing liquid MS medium supplemented with 2,4-D (10 mg/ml), and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (helium retrofit) (Bio-Rad Laboratories, Hercules, Calif.). To 50 µl of a 60 mg/ml 1.0 mm gold particle suspension were added (in order): 30 µl of 10 ng/µl QC339 DNA fragment UBQ:YFP:MYB2-SAMS:HRA, QC340 DNA fragment UBQ:YFP:KTI1-SAMS-HRA, QC350 DNA fragment UBQ:YFP:PIP1-SAMS-HRA, QC351 DNA fragment UBQ:YFP:EF1A2-SAMS-HRA, or QC352 DNA fragment UBQ:YFP:MTH1-SAMS-HRA; 20 µl of 0.1 M spermidine; and 25 µl of 5 M CaCl$_2$. The particle preparation was then agitated for 3 minutes and spun in a centrifuge for 10 seconds, and the supernatant was removed. The DNA-coated particles were then washed once in 400 µl 100% ethanol and resuspended in 45 µl of 100% ethanol. The DNA/particle suspension was sonicated three times for one second each. 5 µl of the DNA-coated gold particles was then loaded on each macro carrier disk.

Approximately 300-400 mg of a two-week-old suspension culture was placed in an empty 60×15 mm Petri dish, and the residual liquid removed from the tissue with a pipette. For each transformation experiment, approximately 5 to 10 plates of tissue were bombarded. Membrane rupture pressure was set at 1100 psi, and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron, the selection agent. The selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to solid agar MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media, and transgenic soybean plantlets were regenerated. The transgenic plants were then transferred to soil and maintained in growth chambers for seed production.

During the transformation, genomic DNA was extracted from somatic embryo samples and analyzed by quantitative PCR using the 7500 real time PCR system (Applied Biosystems) with gene-specific primers and FAM-labeled fluorescence probes to check copy numbers of both the UBQ:YFP:terminator expression cassette and the SAMS:HRA expression cassette. The qPCR analysis was done in duplex reactions with a heat shock protein (HSP) gene as the endogenous control and a transgenic DNA sample with a known single copy of SAMS:HRA or YFP transgene as the calibrator using the relative quantification methodology (Applied Biosystems). The endogenous control HSP probe (SEQ ID NO:69) was labeled with VIC, and the YFP and SAMS probes (SEQ ID NO:66 and SEQ ID NO:63, respectively) were labeled with FAM for the simultaneous detection of both fluorescent probes (Applied Biosystems). Gene cassette-specific primers used in the qPCR were: SAMS48-F and SAMS-134R (SEQ ID NO:62 and SEQ ID NO:64, respectively) for SAMS:HRA, YFP-67F and YFP-130R (SEQ ID NO:65 and SEQ ID NO:67, respectively) for YFP, and HSP-F1 and HSP-R1 (SEQ ID NO:68 and SEQ ID NO:70, respectively) for the endogenous control gene HSP.

Only transgenic soybean events containing 1 or 2 copies of both the SAMS:HRA expression cassette and the UBQ:YFP expression cassette were selected for further gene expression evaluation and seed production (see Table 2). Events negative for YFP qPCR or with more than 2 copies for the SAMS:HRA qPCR were not advanced. Four events from each terminator construct were selected for RT-PCR analysis of gene expression, mRNA polyadenylation, and transcription termination, as described in EXAMPLES 5, 6, and 7. YFP expressions are described in detail in EXAMPLE 4 and are also summarized in Table 2.

TABLE 2

Relative transgene copy numbers and YFP expression of terminator constructs in transgenic soybeans

| Terminator | Event ID | YFP | YFP qPCR | SAMS qPCR |
|---|---|---|---|---|
| MYB2 | 4906.1.1 | + | 0.0 | 0.0 |
| MYB2 | 4906.1.2 | + | 1.1 | 0.5 |
| MYB2 | 4906.1.3 | + | 0.4 | 0.2 |
| MYB2 | 4906.1.4 | + | 0.6 | 0.4 |
| MYB2 | 4906.1.8 | + | 0.1 | 0.1 |
| MYB2 | 4906.1.9 | + | 0.7 | 1.0 |
| MYB2 | 4906.2.1 | + | 0.5 | 0.5 |
| MYB2 | 4906.2.2 | + | 0.8 | 0.3 |
| MYB2 | 4906.2.4 | + | 0.1 | 0.1 |
| MYB2 | 4906.2.5 | + | 0.2 | 0.1 |
| MYB2 | 4906.6.2 | + | 1.6 | 1.5 |
| MYB2 | 4906.7.1 | + | 1.1 | 0.5 |
| MYB2 | 4906.8.1 | + | 1.5 | 1.6 |
| MYB2 | 4906.8.2 | + | 0.8 | 0.6 |
| MYB2 | 4906.8.5 | + | 0.1 | 0.0 |
| MYB2 | 4906.8.7 | + | 1.7 | 1.6 |
| KTI1 | 4909.1.1 | + | 1.3 | 1.4 |
| KTI1 | 4909.1.2 | + | 1.2 | 1.7 |
| KTI1 | 4909.2.1 | + | 1.2 | 1.7 |
| KTI1 | 4909.2.2 | + | 0.9 | 1.1 |
| KTI1 | 4909.2.4 | + | 1.0 | 1.5 |
| KTI1 | 4909.4.2 | + | 1.0 | 1.3 |
| KTI1 | 4909.5.1 | + | 1.1 | 1.0 |
| KTI1 | 4909.7.1 | + | 1.3 | 1.4 |
| KTI1 | 4909.7.2 | + | 1.2 | 1.9 |
| KTI1 | 4909.8.1 | + | 1.4 | 1.8 |
| KTI1 | 4909.8.2 | + | 1.2 | 1.3 |
| KTI1 | 4909.8.3 | + | 1.1 | 1.0 |
| KTI1 | 4909.8.4 | + | 1.0 | 1.1 |
| KTI1 | 4909.8.5 | + | 0.8 | 1.2 |
| PIP1 | 4952.1.2 | + | 1.6 | 1.1 |
| PIP1 | 4952.2.1 | + | 1.6 | 1.3 |
| PIP1 | 4952.3.1 | + | 3.3 | 1.6 |
| PIP1 | 4952.4.2 | + | 2.2 | 2.2 |
| PIP1 | 4952.4.4 | + | 1.0 | 0.8 |
| PIP1 | 4952.7.1 | + | 1.2 | 1.7 |
| PIP1 | 4952.7.2 | + | 1.3 | 1.0 |
| PIP1 | 4952.3.3 | + | 1.2 | 1.6 |
| PIP1 | 4952.3.5 | + | 1.6 | 0.7 |
| PIP1 | 4952.4.5 | + | 2.9 | 2.0 |
| PIP1 | 4952.4.6 | + | 3.5 | 0.6 |
| PIP1 | 4952.4.7 | + | 3.7 | 1.5 |
| PIP1 | 4952.4.10 | + | 0.9 | 0.7 |
| PIP1 | 4952.7.3 | + | 3.0 | 1.2 |
| PIP1 | 4952.7.4 | + | 2.9 | 1.5 |
| PIP1 | 4952.7.5 | + | 1.0 | 0.7 |
| EF1A2 | 4953.1.2 | + | 1.0 | 1.0 |
| EF1A2 | 4953.1.5 | + | 1.1 | 0.6 |
| EF1A2 | 4953.2.2 | + | 1.0 | 1.0 |
| EF1A2 | 4953.4.7 | + | 1.0 | 1.4 |
| EF1A2 | 4953.4.9 | + | 0.9 | 0.9 |
| EF1A2 | 4953.5.3 | + | 1.0 | 0.7 |
| EF1A2 | 4953.5.4 | + | 0.9 | 0.6 |
| EF1A2 | 4953.5.5 | + | 0.9 | 0.9 |
| EF1A2 | 4953.5.6 | + | 0.9 | 1.4 |
| EF1A2 | 4953.6.1 | + | 1.0 | 1.3 |
| EF1A2 | 4953.6.2 | + | 0.8 | 0.9 |
| EF1A2 | 4953.6.6 | + | 0.9 | 1.0 |
| EF1A2 | 4953.6.10 | + | 0.9 | 1.0 |
| EF1A2 | 4953.7.1 | + | 0.9 | 0.7 |
| EF1A2 | 4953.7.3 | + | 0.9 | 0.8 |
| EF1A2 | 4953.8.1 | + | 1.1 | 1.0 |
| EF1A2 | 4953.8.2 | + | 1.1 | 0.9 |
| MTH1 | 5238.8.1 | + | 0.9 | 0.5 |
| MTH1 | 5238.8.2 | + | 1.7 | 0.5 |
| MTH1 | 5238.8.4 | + | 1.1 | 0.9 |
| MTH1 | 5238.2.1 | + | 1.1 | 1.4 |
| MTH1 | 5238.2.4 | + | 2.0 | 1.1 |
| MTH1 | 5238.2.5 | + | 1.2 | 0.5 |
| MTH1 | 5238.2.6 | + | 1.0 | 0.8 |
| MTH1 | 5238.2.8 | + | 1.0 | 0.7 |
| MTH1 | 5238.3.2 | + | 1.3 | 1.3 |
| MTH1 | 5238.3.3 | + | 1.0 | 0.9 |
| MTH1 | 5238.7.1 | + | 1.3 | 0.8 |

TABLE 2-continued

Relative transgene copy numbers and YFP expression of terminator constructs in transgenic soybeans

| Terminator | Event ID | YFP | YFP qPCR | SAMS qPCR |
|---|---|---|---|---|
| MTH1 | 5238.8.6 | + | 1.3 | 0.7 |
| MTH1 | 5238.8.7 | + | 1.0 | 0.9 |
| MTH1 | 5238.7.10 | + | 1.6 | 0.7 |
| MTH1 | 5238.7.12 | + | 0.6 | 0.9 |
| MTH1 | 5238.7.13 | + | 1.3 | 0.6 |

Example 4

YFP Expression in Stable Transgenic Soybeans

Figure 4:
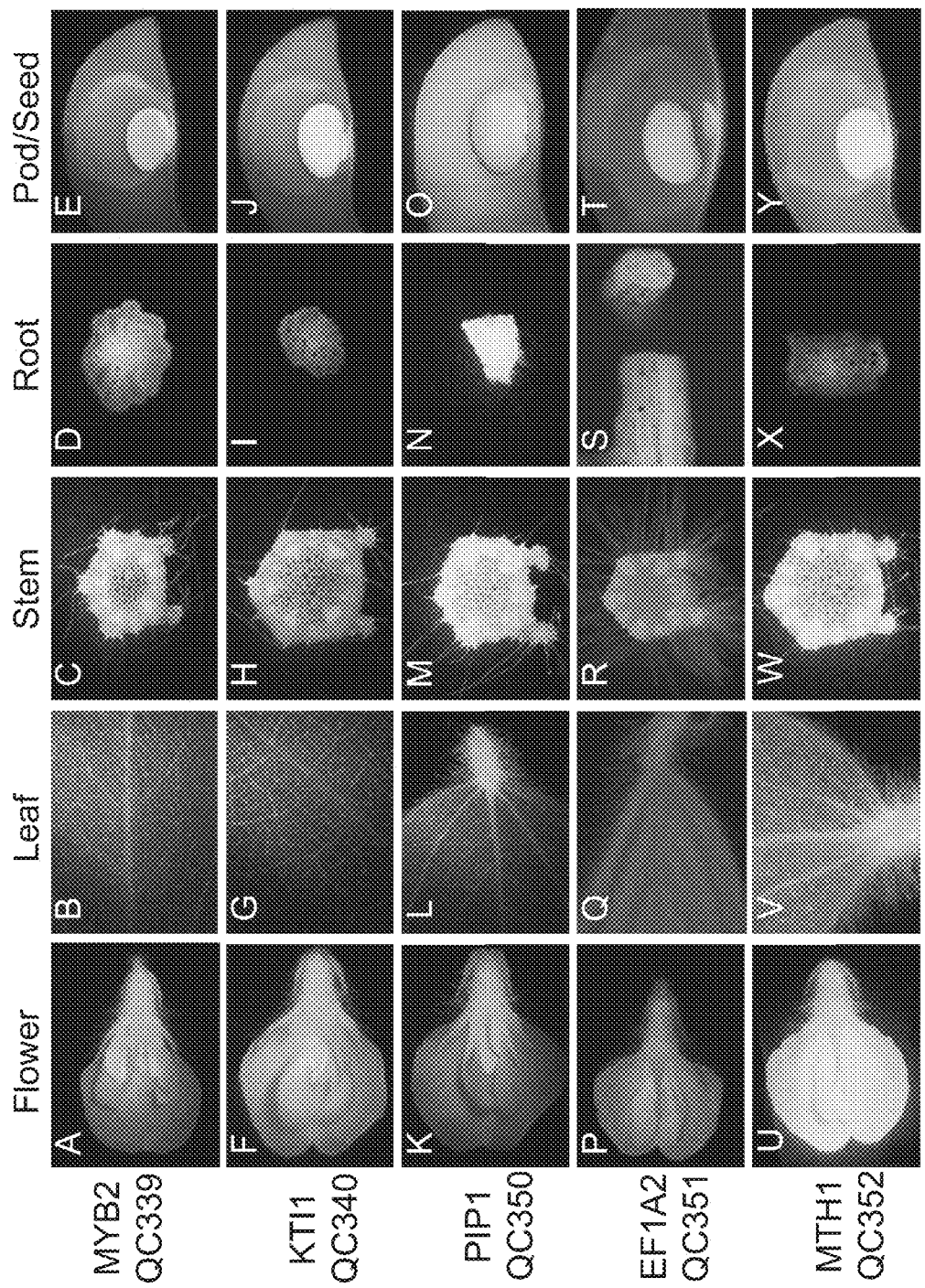
FIG. 4 shows the expression of YFP (yellow fluorescent protein) in representative flower, leaf, stem, root, and pod/seed tissues of transgenic plants derived from the terminator constructs QC339 (MYB2), QC340 (KTI1), QC350 (PIP1), QC351 (EF1A2), and QC352 (MTH1).

YFP gene expression was tested at different stages of transgenic plant development for yellow fluorescence emission under a Leica MZFLIII stereo microscope equipped with appropriate fluorescent light filters. Yellow fluorescence was detected early on during somatic embryo development and throughout all stages of transgenic plant development in all tissues tested (including somatic embryos, leaf, stem, root, flower, pod, and seed) for all five terminator constructs, QC339, QC340, QC350, QC351, and QC352. Since all five terminators were tested in the context of the same soybean ubiquitin promoter GM-UBQ, the reporter expression patterns and strengths were similar among the five constructs suggesting that the terminators did not change the overall expression of the promoter. The five terminators could not be distinguished from each other in terms of reporter gene expression. Examples of YFP expression in flower, leaf, stem, root, and pod/seed are described below and shown in FIG. 4 (for the MYB2 terminator construct QC339, FIG. 4A-E; for the KTI1 terminator construct QC340, FIG. 4F-J; for the PIP1 terminator construct QC350, FIG. 4K-O; for the EF1A2 terminator construct QC351, FIG. 4P-T; and for the MTH1 terminator construct QC352, FIG. 4U-Y).

During the tissue culture stages of transgenic plant regeneration, YFP expression was detected in globular, torpedo, fully developed, and dried down somatic embryos. Negative control embryos emitted weak red color, as did the negative sectors of positive embryo clusters, due to autofluorescence from the chlorophyll contained in green tissues, including somatic embryos. Negative controls for other green tissues, such as leaf or stem, were also red, and negative controls for white tissues, such as root and flower petal, were dark yellowish under the YFP light filter. When transgenic plantlets were regenerated, YFP expression was detected in leaf, stem, and root, and the expression was retained to mature plants. Fluorescence in leaflets collected from plantlets seemed stronger than in leaves collected from mature plants, probably due in part to the weak masking effect of less chlorophyll on yellow fluorescence in young leaves. Fluorescence was concentrated in the vascular bundles in stems and roots. Strong yellow fluorescence was unanimously detected in reproductive organs such as flowers and developing pods and seeds, including seed coats and embryos, at all stages. In conclusion, each of the five novel terminators gave constitutive YFP expression under the control of the soybean ubiquitin promoter.

Example 5

Gene Expression Evaluation by RT-PCR

To evaluate the functions of the terminators, total RNA was extracted from selected transgenic plantlets using the Trizol reagent following the protocol recommended by the manufacturer (Invitrogen). RNA samples were treated with RNase-free DNase I (Invitrogen) to get rid of any potential genomic DNA contamination and checked by RT-PCR with primers SAMS-L (SEQ ID NO:53) and SAMS-L2 (SEQ ID NO:54), which are specific to an endogenous S-adenosylmethionine synthetase gene. Since the SAMS-L primer is specific to the upstream of a 5'UTR intron of the SAMS gene and the SAMS-L2 primer is specific to the coding region downstream of the same intron, any SAMS genomic DNA will produce a 967 bp PCR band, while the SAMS cDNA will produce a 376 bp RT-PCR band.

A typical 25 µl RT-PCR reaction was set up with 100 ng total RNA, 200 nM sense primer, 200 nM antisense primer, and 12.5 µl 2× one-step RT-PCR reaction mix (Invitrogen). The RT-PCR program included 30 minutes at 50° C. for the first strand cDNA synthesis; 3 minutes at 94° C. for the initial denaturing; and 35 cycles of 30 seconds at 94° C., 1 minute at 60° C., and 1 minute at 72° C. A final incubation at 72° C. for 5 minutes was included before holding at 4° C. RT-PCR products were resolved in 1% agarose gels by electrophoresis. All RNA samples were checked by this assay and were determined to be genomic DNA-free as shown in FIG. 6A, where no 967 bp band, specific to genomic DNA, was amplified from any of the RNA samples. Since the SAMS-L primer is at the far 5' end of the SAMS gene, the successful amplification of the 376 bp RT-PCR band from all the RNA samples also confirmed that each of the RNA sequences was full-length. A similar check was also done with primers UBQ-S2 (SEQ ID NO:61) and YFP-A (SEQ ID NO:60), which were specific to the UBQ:YFP transgene, to further confirm that the RNAs were full-length and free of genomic DNA contamination.

Figure 5:
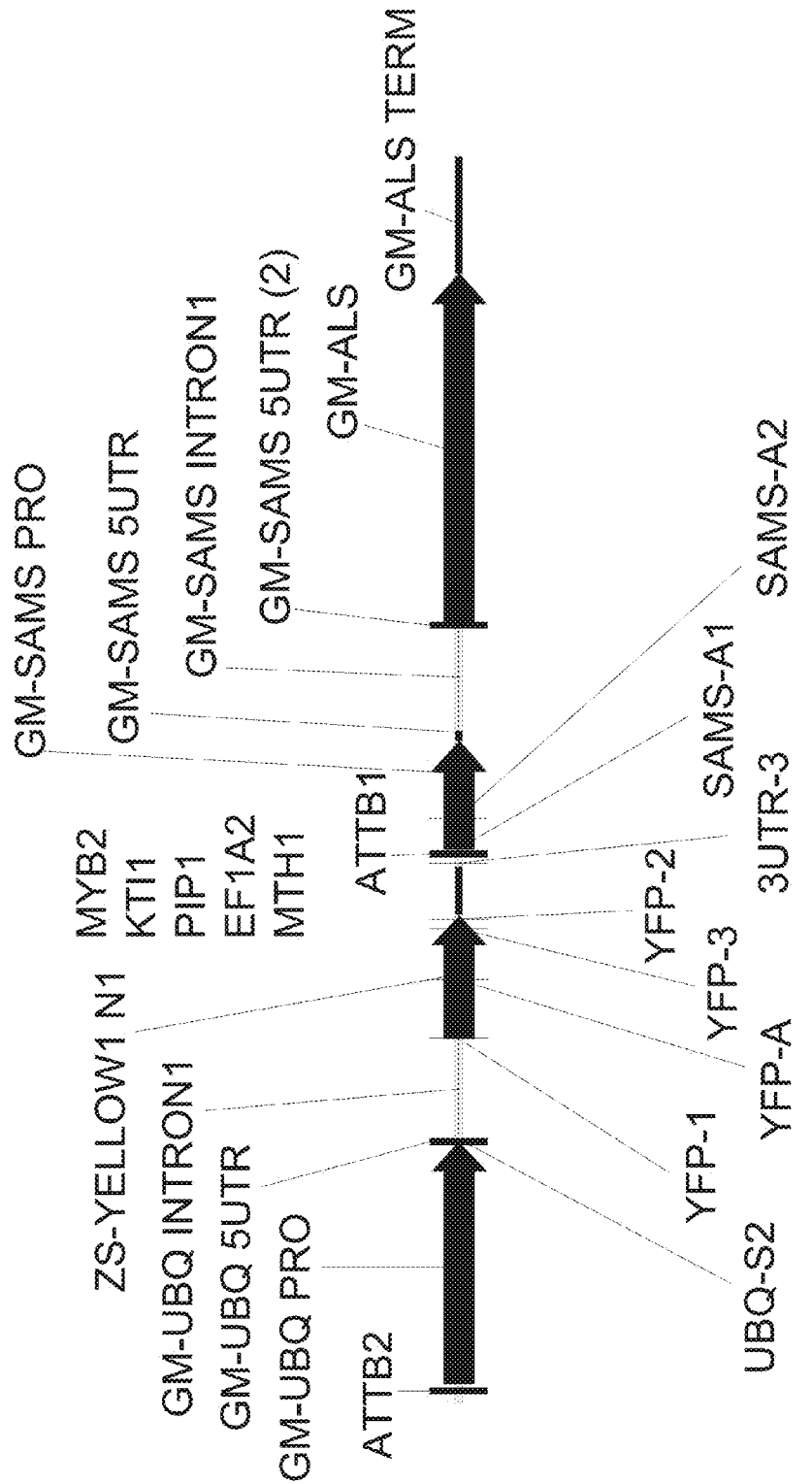
FIG. 5 shows the map of predicted terminator transgenes in plants and the positions of primers used in RT-PCR and PCR analyses of transgene expression and RNA transcription termination.

In addition to the UBQ-S2/YFP-A primers used to check the transgene transcripts, other transgene-specific primers were designed for different analytical purposes (FIG. 5). To check the UBQ:YFP transgene expression, four independent events selected from each of the five terminator transformations were analyzed by RT-PCR, as described above, with primers YFP-1 (SEQ ID NO:57) and YFP-2 (SEQ ID NO:58). For each terminator transformation, all four samples produced the expected YFP band with the same intensity, indicating that all of the tested transgenic events expressed the YFP transgene similarly (FIG. 6B).

Example 6

Evaluation of Transgene Transcription Termination

The ability of the terminators to terminate RNA transcription was analyzed by RT-PCR using the sense primer YFP-3 (SEQ ID NO:59), which is specific to the YFP gene, and an antisense primer specific to a region downstream from and beyond the terminator in the transgene construct. Since all five terminator constructs have the same configuration, the same antisense primers, 3UTR-3 (SEQ ID NO:52), SAMS-A1 (SEQ ID NO:55), and SAMS-A2 (SEQ ID NO:56), could be used to analyze the progressive termination of transcripts for all five terminators, MYB2, KTI1, PIP1, EF1A2, and MTH1 (FIG. 5). If RNA transcription was terminated 100% by the terminator, no RT-PCR band would be detected with any of the primer set. If the transcription termination was not 100% effective and some RNA transcripts read through and beyond the terminator region, a band of expected size would be amplified by the RT-PCR with each respective primer set.

Most of the transgenic events showed RNA transcription read through bands with all three primer sets, YFP-3/3UTR-3, YFP-3/SAMS-A1, and YFP-3/SAMS-A2 (FIG. 7). The RT-PCR with primers YFP-3/3UTR-3 also amplified an approximately 400 bp non-specific band from wild type RNA in addition to the specific RT-PCR bands from the transgenic RNA templates (FIG. 7A). The larger transgene transcript-specific bands were amplified from each of the four samples of all five terminators MYB2, KTI1, PIP1, EF1A2, and MTH1, except for the first MYB2 sample. An intense smaller band was amplified for this sample suggesting that the transgene probably contained a deletion in the terminator region in this MYB2 event. Indeed, a 3' UTR sequence recovered from this event contained a 362 bp deletion in the middle of the MYB2 terminator (EXAMPLE 8). A transgene read through-specific band slightly larger than the wild type non-specific band was also amplified from the four transgenic events carrying a control transgene operably linked to the potato PIN2 terminator. Expected sizes of the transgene-specific bands are given in FIG. 7 adjacent to the terminator names. The results indicated that none of the terminators, including the commonly used PIN2, stopped RNA transcription completely. Instead, transcription read-through beyond the 3' end of the terminators occurred frequently, though at various levels, as indicated by the different intensities of the bands.

Since the 3UTR-3 antisense primer is only 38 bp (including the 23 bp 3UTR-3 primer sequence) from the EcoRI site at the 3' end of all the terminators, the extent of transcription read-through could be further evaluated using two more sets of primers further downstream of the terminator. The antisense primer SAMS-A1 used in the second RT-PCR is 248 bp downstream of the 3UTR-3 primer used in the first RT-PCR, or 286 bp downstream of the 3' end (the EcoRI cloning site) of all the terminators. The antisense primer SAMS-A2 used in the third RT-PCR is 174 bp downstream of the SAMS-A1 primer, or 422 bp downstream of the 3UTR-3 primer, or 460 bp downstream of the terminator's 3' end. The second set of primers, YFP-3/SAMS-A1, amplified RT-PCR bands from all the KTI1, PIP1, and EF1A2 samples, although the second EF1A2 sample had a very faint band. The number 4 MYB2 sample, the number 2 MTH1 sample, and all four PIN2 samples produced faint bands of the expected sizes. The first MYB2 samples again produced an intense but smaller band. (FIG. 7B). The third set of primers, YFP-3/SAMS-A2, amplified similar bands, although there were slight changes in intensity for some of the bands, as compared to the second RT-PCR (FIG. 7C). Some bands became weaker and some bands became stronger, presumably due to PCR variations. The results indicated that RNA transcription did not terminate at one site, with some RNA transcripts extending as far as 460 bp or longer downstream of the 3' end of the tested terminator. Transcription read-through was less severe in terminators MYB2, MTH1, and PIN2, as compared to terminators PIP1, KTI1, and EF1A2.

To check the percentage of transcription read through, the relative quantity of the YFP transcripts estimated by qRT-PCR was compared to that of the SAMS promoter (FIG. 5). The sense primer YFP-139F (SEQ ID NO:74), probe YFP-160T (SEQ ID NO:75), and antisense primer YFP-195R (SEQ ID NO:76), all of which are specific to the 3' end of the YFP coding region, were used for YFP-specific qRT-PCR. The qRT-PCR specific to the SAMS promoter designed to locate further downstream of the terminators used sense primer SamsPro-F (SEQ ID NO:71), probe SamsPro-T (SEQ ID NO:72), and antisense primer SamsPro-R (SEQ ID NO:73). The antisense primer SamsPro-R is 553 bp downstream of the 3UTR-3 primer or 591 bp downstream of the 3' end EcoRI site of the terminators. The endogenous ATP sulfurylase gene, detected with sense primer ATPS-87F (SEQ ID NO:20), probe ATPS-117T (SEQ ID NO:93), and antisense primer ATPS-161R (SEQ ID NO:21), was used as the endogenous control for both the YFP and SAMS promoter qRT-PCR. The genomic DNA of a transgenic soybean event containing one copy of both YFP and SAMS promoter was used as a calibrator. The relative quantification (RQ) of YFP or SAMS promoter was calculated using the 7500 system SDS software (Applied Biosystems). RNA transcription read through frequency was expressed as the percentage of the expression of SAMS promoter to that of YFP for each tested sample. Four independent transgenic events were analyzed for each of the five terminators. Transcription read through was detected in all the events though most of them were less than 1% as listed in the last column of Table 3.

TABLE 3

Relative quantification of RNA transcription read through by qRT-PCR

| Terminator | RNA source | Event | YFP-RQ | SamsPro-RQ | SamsPro/YFP |
|---|---|---|---|---|---|
| MYB2 | Embryo | 4906.1.2 | 0.188 | 0.008 | 4.26% |
|  | Embryo | 4906.5.3 | 1.13 | 0.005 | 0.44% |
|  | Embryo | 4906.6.1 | 0.566 | 1.94E−04 | 0.03% |
|  | Embryo | 4906.8.1 | 1.144 | 2.79E−04 | 0.02% |
| KTI1 | Leaf | 4909.2.4.2 | 11.05 | 0.037 | 0.33% |
|  | Leaf | 4909.7.1.2 | 5.25 | 0.025 | 0.48% |
|  | Leaf | 4909.8.2.2 | 7.166 | 1.31 | 18.28% |
|  | Leaf | 4909.8.3.1 | 7.499 | 0.029 | 0.39% |
| PIP1 | Plantlet | 4952.3.1 | 19.873 | 0.081 | 0.41% |
|  | Plantlet | 4952.4.4 | 6.511 | 0.001 | 0.02% |
|  | Plantlet | 4952.4.10 | 4.881 | 0.02 | 0.41% |
|  | Plantlet | 4952.7.3 | 15.528 | 0.038 | 0.24% |
| EF1A2 | Embryo | 4953.1.1 | 0.452 | 0.003 | 0.66% |
|  | Embryo | 4953.2.1 | 0.009 | 2.59E−04 | 2.88% |
|  | Embryo | 4953.4.4 | 0.757 | 0.007 | 0.92% |
|  | Embryo | 4953.5.1 | 0.685 | 0.012 | 1.75% |
| MTH1 | Plantlet | 5238.2.12 | 25.548 | 0.018 | 0.07% |
|  | Plantlet | 5238.6.8 | 13.572 | 0.025 | 0.18% |
|  | Plantlet | 5238.7.11 | 9.022 | 0.023 | 0.25% |
|  | Plantlet | 5238.7.12 | 6.943 | 0.009 | 0.13% |

Example 7

Evaluation of Endogenous Gene Transcription Termination

Though it is believed that transcription termination by bacterial RNA polymerase (RNAP) occurs at sequences coding for a GC-rich RNA hairpin followed by a U-rich tract (Gusarov and Nudler, Mol. Cell 3:495-504 (1999), Larson et al., Cell 132:971-982 (2008)), little is known about transcription termination in plants. To check if transcription read through observed in transgenes is also common for endogenous genes, primers were designed to check RNA transcripts of each of the five endogenous genes corresponding to the five terminators. The first set of primers, specific to normal mature mRNA, consisted of a sense primer specific to the coding region and an antisense primer specific to the 3UTR upstream of the poly (A). An RT-PCR band of a specific size would be expected from soybean wild type total RNA and from genomic DNA positive control. The second set of primers, specific to read through transcripts or precursor mRNA, consisted of the same sense primer specific to the coding region and an antisense primer specific to a region approximately 100-300 bp downstream of the poly (A). If transcription read through did occur, a larger band would be expected from total RNA by RT-PCR and from genomic DNA by PCR. If transcription read through did not occur, only the genomic DNA templates would produce the larger PCR band. The RNA templates would not produce the larger band if RNA transcripts did not extend 100-300 bp beyond the polyadenylation site.

RT-PCR analysis was done on wild type RNA extracted from soybean plantlets for each of the five terminators MYB2, KTI1, PIP1, EF1A2, and MTH1 (FIG. 8A). The RNA used in the assays had been checked to be free of any genomic DNA contamination and the band detected in the RNA samples had to come from RNA by RT-PCR. Genomic DNA was included as positive control, and water was used as a no template control for each set of primers. The RT-PCR-1 used normal mRNA-specific primer sets, and the RT-PCR-2 used transcription read-through specific primer sets (FIG. 8A). The normal mRNA-specific primer sets used in RT-PCR-1 were: PSO323364S1/PSO323364R1 (SEQ ID NO:77/SEQ ID NO:78), PSO400362S1/PSO400362R1 (SEQ ID NO:79/SEQ ID NO:80), PSO332982F/ PSO0332986JK-A (SEQ ID NO:81/SEQ ID NO:82), PSO333268F/PSO333268R (SEQ ID NO:83/SEQ ID NO:84), and PSO333209F/PSO333209JK-A (SEQ ID NO:85/SEQ ID NO:86), respectively, for the MYB2, KTI1, PIP1, EF1A2, and MTH1 terminators. The transcription read-through specific primer sets used in RT-PCR-2 were PSO323364S1/PSO323364Eco (SEQ ID NO:77/SEQ ID NO:41), PSO400362S1/PSO400362Eco (SEQ ID NO:79/ SEQ ID NO:43), PSO332982F/PSO332986Eco (SEQ ID NO:81/SEQ ID NO:45), PSO333268F/PSO333268Eco (SEQ ID NO:83/SEQ ID NO:47), and PSO333209F/ PSO333209Eco (SEQ ID NO:85/SEQ ID NO:49), respectively, for the MYB2, KTI1, PIP1, EF1A2, and MTH1 terminators.

RT-PCR bands were detected with both the mRNA specific RT-PCR-1 and the transcription read-through specific RT-PCR-2 from the RNA samples for PSO333209 (MTH1), PSO333268 (EF1A2), and PSO332986 (PIP1). As expected, the RT-PCR-2 bands are larger than the corresponding RT-PCR-1 bands. Bands of the same sizes were detected in the genomic DNA positive controls for all the primer sets (FIG. 8A). Since PSO323364 (MYB2) is a flower-specific gene and PSO400362 (KTI1) is an embryo-specific gene, no RT-PCR band was amplified with RT-PCR-1 or RT-PCR-2 from the plantlet RNA samples for these two genes, while both amplified specific PCR bands from the genomic DNA positive controls (FIG. 8A). Flower RNA and embryo RNA had to be used accordingly in order to check transcription read-through for these two tissue-specific genes (FIG. 8B). RT-PCR bands were amplified by both RT-PCR-1 and RT-PCR-2 for PSO323364 (MYB2) from the flower RNA but not from the seed RNA, while for gene PSO400362 (KTI1), from the seed RNA but not from the flower RNA (FIG. 8B). Both the flower and seed RNA were also checked by RT-PCR with primers SAMS-L/SAMS-L2 (SEQ ID NO:53/ SEQ ID NO:54) to be free of genomic DNA contamination (FIG. 8B). Since the antisense primer used in each RT-PCR-2 was 222 bp, 296 bp, 194 bp, 87 bp, and 195 bp from the polyadenylation site (see SEQ ID NO:6, 7, 8, 9, and 10), respectively, for genes PSO323364 (MYB2), PSO400362 (KTI1), PSO332986 (PIP1), PSO333268 (EF1A2), and PSO333209 (MTH1), the results confirmed that RNA transcription did not terminate at the corresponding position downstream of the polyadenylation site for each of the five endogenous genes. The terminators behaved similarly in their naturally endogenous genes as when they were in transgenic genes described in EXAMPLE 6.

Example 8

Cloning and Sequencing the 3' UTRs of Transgenes

Transgenic 3' UTRs were cloned by RT-PCR from the same four events for each of the MYB2, KTI1, PIP1, EF1A2, and MTH1 terminators. First strand cDNA was made from each RNA sample with SuperScript III reverse transcriptase (Invitrogen), using the oligo dT primer 3UTR-1 (SEQ ID NO:50). The 3' UTR, plus the 3' part of the YFP coding region of each transgene, was amplified by PCR with primer set YFP-3/3UTR-2 (SEQ ID NO:59/SEQ ID NO:51). A single band was amplified for all but the four MYB2 samples and one EF1A2 sample (FIG. 9). The PCR bands were then cloned into TOPO pCR2.1 vector by TA cloning (Invitrogen). Plasmid DNA was obtained from each clone, using Qiagen plasmid mini kits, and the DNA was sequenced with M13For and M13Rev primers specific to the TOPO pCR2.1 vector. Sequences were analyzed using the ContigExpress and AlignX programs in Vector NTI suites (Invitrogen).

As summarized in Table 4, 19 specific 3' UTR sequences representing 5 different variants were recovered from the MYB2 events. The lengths of the five variants, starting from the 5' SacI site of the MYB2 terminator, are 143 bp, 198 bp, 244 bp, 341 bp, and 348 bp. In total, there were four 143 bp sequences, ten 198 bp sequences, one 244 bp sequence, two 341 bp sequences, and two 348 bp sequences. Two identical 3' UTR sequences (not listed in the table) cloned from the first MYB2 event had the middle 362 bp of the MYB2 terminator deleted and the polyadenylation site was outside the terminator, i.e., 43 bp downstream of the 3UTR-3 primer or 81 bp downstream of the 3' end (the EcoRI site) of the terminator. The observation is consistent with the smaller PCR bands amplified for the first MYB2 event (FIG. 7A, B, C). The middle deletion in the terminator made RNA transcription read through more severe in this event than in the others since this event gave much stronger bands for all three sets of primers used for the transcription read through check, as described in EXAMPLE 6.

Thirteen 3' UTR sequences representing 5 variants were recovered from the KTI1 events; eleven 3' UTR sequences representing only 2 variants were recovered from the PIP1 events; twelve sequences representing 2 variants were recovered from the EF1A2 events, and twenty five sequences representing 13 variants were recovered from the MTH1 events. It was obvious that each terminator could have multiple polyadenylation sites. Since only limited numbers of clones were sequenced for each terminator, it was reasonable to believe that more polyadenylation sites could be identified, especially for the MTH1, KTI1, and MYB2 terminators, since some of their 3' UTR variants were represented by only single sequences in Table 4.

TABLE 4

Summary of transgenic 3' UTR sequence analysis

| | Terminator | | | | |
|---|---|---|---|---|---|
| | MYB2 | KTI1 | PIP1 | EF1A2 | MTH1 |
| Gene | PSO323364 | PSO400362 | PSO332986 | PSO333268 | PSO333209 |
| Native 3' UTR | 305 | 243 | 309 | 345 | 259 |
| Construct | QC339 | QC340 | QC350 | QC351 | QC352 |
| Full length | 540 | 554 | 518 | 445 | 462 |
| Transgene 3' UTR sequence | 19 | 13 | 11 | 12 | 25 |
| Transgene 3' UTR variants | 5 | 5 | 2 | 2 | 13 |
| Transgene 3' UTR variants lengths and frequency | 143(4), 198(10), 244(1), 341(2), 348(2) | 169(1), 179(1), 202(6), 242(3), 250(2), | 319(7), 337(4) | 351(10), 369(2) | 213(1), 219(1), 240(1), 259(8), 263(1), 275(1), 277(1), 298(3), 318(1), 324(3), 329(1), 343(2), 367(1) |

Example 9

Identification and Cloning of Longer Versions of the Terminators

As described in EXAMPLE 7, transcription read through was detected in all five endogenous genes, PSO0323364, PSO0400362, PSO0332986, PSO0333268, and PSO333209, corresponding to terminators MYB2, KTI1, PIP1, EF1A2, and MTH1, respectively (FIG. 8). To check if the observed transcription read through of endogenous genes would stop and at what point, six more progressively downstream reverse primers were designed for each of the five endogenous genes based on their genomic DNA sequences to do more RT-PCR analyses. The relative positions of the single forward primer PSO323364S1 (SEQ ID NO:77) and seven reverse primers PSO323364Eco (SEQ ID NO:41), PSO323364UTR2 (SEQ ID NO:94), PSO323364UTR3 (SEQ ID NO:95), PSO323364UTR4 (SEQ ID NO:96), PSO323364UTR5 (SEQ ID NO:97), PSO323364UTR6 (SEQ ID NO:98), and PSO323364UTR7 (SEQ ID NO:99) specific to the RNA transcript and the genomic DNA of gene PSO323364 are illustrated in FIG. 10 as an example. RT-PCR analyses using the above seven sets of primers were labeled in the same order, as RT-PCR 1, RT-PCR 2, RT-PCR 3, RT-PCR 4, RT-PCR 5, RT-PCR 6, and RT-PCR 7 in FIG. 11.

Similarly, primers were designed and RT-PCR was performed for the other four endogenous genes, PSO400362, PSO332986, PSO333268, and PSO333209. Forward primer PSO400362S1 (SEQ ID NO:79) and seven reverse primers PSO400362Eco (SEQ ID NO:43), PSO400362UTR2 (SEQ ID NO:100), PSO400362UTR3 (SEQ ID NO:101), PSO400362UTR4 (SEQ ID NO:102), PSO400362UTR5 (SEQ ID NO:103), PSO400362UTR6 (SEQ ID NO:104), and PSO400362UTR7 (SEQ ID NO:105) were used for the seven PSO400362-specific RT-PCR analyses (FIG. 11). Forward primer PSO332982F (SEQ ID NO:81) and seven reverse primers PSO332986Eco (SEQ ID NO:45), PSO332986UTR2 (SEQ ID NO:106), PSO332986UTR3 (SEQ ID NO:107), PSO332986UTR4 (SEQ ID NO:108), PSO332986UTR5 (SEQ ID NO:109), PSO332986UTR6 (SEQ ID NO:110), and PSO332986UTR7 (SEQ ID NO:111) were used for the seven PSO332986-specific RT-PCR analyses (FIG. 11). Forward primer PSO333268F (SEQ ID NO:83) and seven reverse primers PSO333268Eco (SEQ ID NO:47), PSO333268UTR2 (SEQ ID NO:112), PSO333268UTR3 (SEQ ID NO:113), PSO333268UTR4 (SEQ ID NO:114), PSO333268UTR5 (SEQ ID NO:115), PSO333268UTR6 (SEQ ID NO:116), and PSO333268UTR7 (SEQ ID NO:117) were used for the seven PSO333268-specific RT-PCR analyses (FIG. 11). Forward primer PSO333209F (SEQ ID NO:85) and seven reverse primers PSO333209Eco (SEQ ID NO:49), PSO333209UTR2 (SEQ ID NO:118), PSO333209UTR3 (SEQ ID NO:119), PSO333209UTR4 (SEQ ID NO:120), PSO333209UTR5 (SEQ ID NO:121), PSO333209UTR6 (SEQ ID NO:122), and PSO333209UTR7 (SEQ ID NO:123) were used for the seven PSO333209-specific RT-PCR analyses (FIG. 11).

RT-PCR analyses were done on the same wild type soybean flower RNA for gene PSO322264 (MYB2), seed RNA for PSO400362 (KTI1), or plantlet RNA for genes PSO332986 (PIP1), PSO333268 (EF1A2), and PSO0333209 (MTH1), as described in EXAMPLE 7. The RNA used in the assays had been checked to be free of any genomic DNA contamination and the band detected in the RNA samples had to come from RNA by RT-PCR. Genomic DNA was included as positive control, and water was used as a no template control for each set of primers. The genomic DNA positive would always give a band as long as the RT-PCR worked. The RNA template would only give the same size band only when there was transcription read through downstream beyond the position of the reverse primer. If transcription read through stopped, only the genomic DNA templates would produce the predicted PCR band. The same size band was detected in both the RNA and genomic DNA template for each of the five endogenous genes until RT-PCR 5 (FIG. 11A, B). RT-PCR 5 reactions were repeated to normalize the RT-PCR reactions in FIG. 11A and in FIG. 11B that were done at different times. Probably due to limited specific targets in the RNA templates, RT-PCR 5 results were not completely consistent between the corresponding reactions in FIG. 11A and in FIG. 11B for genes PIP1 and EF1A2. No specific band was detected in RT-PCR 5 for MTH1 gene while a non-specific band was detected in the same reaction (FIG. 11A). Non-specific bands of different sizes were also detected in RT-PCR 6 for MYB2, PIP1, and EF1A2 genes. The primers failed for PIP1 gene RT-PCR 7 since no band was amplified either from the RNA template or the genomic DNA template (FIG. 11B). No RT-PCR band was amplified in RT-PCR 6 or RT-PCR 7 for any of the five genes indicating that transcription read through did not occur beyond the sixth reverse primer position.

The longer versions of the five terminators were amplified by PCR from wild type soybean "Jack" genomic DNA using the same forward primers described in EXAMPLE 2 and the UTR6 reverse primers. The MYB2L terminator (SEQ ID NO: 124) was amplified with primers PSO323364Sac (SEQ ID NO:40) and PSO323364UTR6 (SEQ ID NO:98). The KTI1L terminator (SEQ ID NO:125) was amplified with primers PSO400362Sac (SEQ ID NO:42) and PSO400362UTR6 (SEQ ID NO:104). The PIP1L terminator (SEQ ID NO:126) was amplified with primers PSO332986Sac (SEQ ID NO:44) and PSO332986UTR6 (SEQ ID NO:110). The EF1A2L terminator (SEQ ID NO:127) was amplified with primers PSO333268Sac (SEQ ID NO:46) and PSO0333268UTR6 (SEQ ID NO:116). The MTH1L terminator (SEQ ID NO:128) was amplified with primers PSO333209Sac (SEQ ID NO:48) and PSO333209UTR6 (SEQ ID NO:122). PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. using the Platinum high fidelity Taq DNA polymerase (Invitrogen). PCR reactions were resolved using agarose gel electrophoresis to identify DNA bands representing the approximately 1.5 Kb terminators. Each longer terminator was then cloned in TOPO TA cloning vector pCR2.1-TOPO (Invitrogen) and confirmed by sequencing multiple clones. The longer terminators are used in constructing transgenic gene cassettes wherever transcription read through needs to be limited.

What is claimed is:

1. A recombinant DNA construct comprising a promoter, at least one heterologous nucleotide sequence, and an isolated polynucleotide comprising:
   a) a nucleotide sequence comprising the sequence set forth in SEQ ID NO:5;
   b) a nucleotide sequence comprising a sequence having at least 95% sequence identity, based on the BLASTN method of alignment, when compared to the nucleotide sequence of (a); or
   c) the nucleotide sequence complementary to (a) or (b); wherein said nucleotide sequence functions as a terminator and wherein the promoter, heterologous nucleotide sequence, and isolated polynucleotide are operably linked.

2. A recombinant DNA construct comprising a promoter, at least one heterologous nucleotide sequence, and an isolated polynucleotide comprising:
   a) a nucleotide sequence comprising a fragment of SEQ ID NO:5;
   b) a nucleotide sequence comprising a sequence having at least 95% sequence identity, based on the BLASTN method of alignment, when compared to the nucleotide sequence of (a); or
   c) the nucleotide sequence complementary to (a) or (b); wherein said nucleotide sequence functions as a terminator and wherein the promoter, heterologous nucleotide sequence, and isolated polynucleotide are operably linked.

3. A vector comprising the recombinant DNA construct of claim 1 or 2.

4. A cell comprising the recombinant DNA construct of claim 1 or 2.

5. The cell of claim 4, wherein the cell is a plant cell.

6. A transgenic plant having stably incorporated into its genome the recombinant DNA construct of claim 1 or 2.

7. The transgenic plant of claim 6 wherein said plant is a dicot.

8. The transgenic plant of claim 7 wherein said plant is soybean.

9. Transgenic seed produced by the transgenic plant of claim 7.

10. A method of expressing a coding sequence or a functional RNA in a plant comprising:
  a) introducing the recombinant DNA construct of claim 1 or 2 into the plant, wherein the at least one heterologous nucleotide sequence comprises the coding sequence or the functional RNA;
  b) growing the plant of step a); and
  c) selecting the plant displaying expression of the coding sequence or the functional RNA of the recombinant DNA construct.

11. A method of transgenically altering a marketable plant trait, comprising:
  a) introducing the recombinant DNA construct of claim 1 or 2 into a plant cell;
  b) growing a fertile, mature plant from the plant cell resulting from step a); and
  c) selecting the plant expressing the at least one heterologous nucleotide sequence in at least one plant tissue based on the altered marketable trait.

12. The method of claim 11 wherein the marketable plant trait is selected from the group consisting of: disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

* * * * *